(12) United States Patent
Tanaka et al.

(10) Patent No.: US 7,902,179 B2
(45) Date of Patent: Mar. 8, 2011

(54) HETEROCYCLIC COMPOUNDS

(75) Inventors: Yasuhiro Tanaka, Kanagawa (JP); Kohichi Fujita, Kanagawa (JP); Yoshitomo Chujoh, Kanagawa (JP); Syunsuke Fukuda, Kanagawa (JP); Yuka Ikenoue, Kanagawa (JP); Tomoyuki Tagami, Kanagawa (JP); Akira Chiba, Kanagawa (JP); Ariko Kodaira, Kanagawa (JP); Hideki Matsumoto, Kanagawa (JP); Tadakiyo Nakagawa, Kanagawa (JP); Tatsuhiro Yamada, Kanagawa (JP); Manabu Suzuki, Kanagawa (JP); Masahiro Murata, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 1542 days.

(21) Appl. No.: 10/475,097

(22) PCT Filed: Apr. 26, 2002

(86) PCT No.: PCT/JP02/04206
§ 371 (c)(1),
(2), (4) Date: Mar. 8, 2004

(87) PCT Pub. No.: WO02/088122
PCT Pub. Date: Nov. 7, 2002

(65) Prior Publication Data
US 2004/0147546 A1  Jul. 29, 2004

(30) Foreign Application Priority Data
Apr. 26, 2001 (JP) .................................. 2001-130438

(51) Int. Cl.
*A61K 31/44* (2006.01)
(52) U.S. Cl. ........................................ 514/183; 514/303
(58) Field of Classification Search .................. None
See application file for complete search history.

(56) References Cited

U.S. PATENT DOCUMENTS

| 4,220,646 A | * | 9/1980 | Cotrel et al. ............. 514/253.04 |
| 5,883,111 A | * | 3/1999 | Naka et al. ................... 514/364 |
| 5,889,032 A | * | 3/1999 | Lohray et al. ................. 514/369 |

FOREIGN PATENT DOCUMENTS

| WO | WO 94/27969 | * 12/1994 |
| WO | 95/01980 | 1/1995 |
| WO | 96/12720 | 5/1996 |

OTHER PUBLICATIONS

Merck Index, 9th Ed., 1976, p. FI-8.*
Souillac, et al., Characterization of Delivery Systems, Differential Scanning Calorimetry, pp. 212-228, in Encyclopedia of Controlled Drug Delivery, 1999, John Wiley & Sons.*
Gibson, "Increased gut permeability on Crohn's disease: is TNF the link?" Gut, 2004: 53, 1724-25.*
Giamarellos-Bourboulis, et al., Effective Immunomodulatory Treatment of *Escherichia coli* Experimental Sepsis with Thalidomide, Antimicrobial Agents and Chemotherapy, Aug. 2003, p. 2445-2449.*
"Access to Anti- TNF-alpha Therapies for Adults with Inflammatory Arthritis," Implementation of NICE Guidance on use of Anti-TNF-alpha Therapies for Adults with Rheumatoid Arthritis, Jun. 2005, pp. 1-8, the NICE Report.*
Waldman, "Targeting the interleukin-15/interleukin-15 receptor system in inflammatory autoimmune diseases," Arthritis Research & Therapy, vol. 6, No. 4, 2004, pp. 174-177.*
Jimenez, "Infliximab in the Treatment of Severe Ulcerative Colitis," Rev. esp. enfirmo Dig., vol. 2004, No. 2, Feb. 2004, 4 pages.*
Odian et al (Schaum's Outline of Theory and Problems of General, Organic, and Biological Chemistry, p. 257, 1994).*
Ask A Scientist (available online at http://www.newton.dep.anl.gov/askasci/chem00/chem00279.htm) accessed online on Feb. 10, 2009.*
Williams et al (Principles of Medicinal Chemistry, 5th Edition, p. 59-61, published Feb. 2002).*
STN Search Notes (Accession No. 1995:406626).*
M. Helmy Elnagdi, "Reactions With β-Cyanoethylhydrazine-I", Tetrahedron, vol. 30, pp. 2791-2796 1974.
Abdou Ahmed El-sayed, et al., "A New Route for the Preparation of Pyrazolo[4,3-c]pyridines", Bulletin of the Chemical Society of Japan, vol. 46, 1801-1803, 1973.
J. Org. Chemi., vol. 24, pp. 963-966, 1959.
Edward C. Taylor, et al., The Reaction of Malononitrile with Substituted Hydrazines: New Routes to a-Aminoyrazolo[3,4-d]pyrimidines[1,2], J. Am. Chem., vol. 81, pp. 2456-2464 1959.
M.D. Nair, et al., "Derivatives of $^2$H-Pyrazolo[4,3-c]pyridines", Indian J. Chem., vol. 5, pp. 464-466 1967.
M. Shimizu, et al., *Drug Metabolism Letters*, vol. 1, pp. 77-79 (2007).
*The Merck Index 12$^{th}$ Ed.*, S. Budavari, et al. Eds., Merck & Co., Inc. Whitehouse Station, NJ 1996, pp. 178, 179, 1247, 1253 and 1677.

* cited by examiner

*Primary Examiner* — Brandon J Fetterolf
*Assistant Examiner* — Craig Ricci
(74) *Attorney, Agent, or Firm* — Oblon, Spivak, McClelland, Maier & Neustadt, L.L.P.

(57) ABSTRACT

A pharmaceutical composition containing a heterocyclic compound of the formula (I)

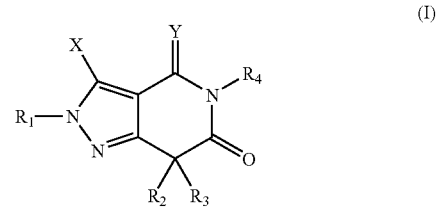

(I)

wherein each symbol is as defined in the specification, an isomer thereof, a solvate thereof or a pharmaceutically acceptable salt thereof as an active ingredient has a superior TNF-α production suppressing action. Accordingly, it is useful for the prophylaxis or treatment of various diseases caused by abnormal production of TNF-α.

15 Claims, 2 Drawing Sheets

HETEROCYCLIC COMPOUNDS

CROSS REFERENCES TO RELATED APPLICATIONS

This application is a 371 of International Patent Application No. PCT/JP02/04206, filed on Apr. 26, 2002, and claims priority to Japanese Patent Application No. 2001-130438, filed on Apr. 26, 2001.

TECHNICAL FIELD

The present invention relates to a novel heterocyclic compound. More particularly, the present invention relates to a heterocyclic compound useful for various inflammatory diseases.

BACKGROUND ART

TNF-α is an inflammatory cytokine produced from macrophage, macrophage-like cells (kupffer's cell and microglia), neutrophile, basophil, acidophil, lymphocyte, NK cell, LAK cell, mast cell, myeloma cell, fibroblast, astrocyte, keratinocyte and the like. Its deep involvement in the onset pathologies of many diseases has been clarified in recent years, and the possibility of establishing a new treatment method based on the regulation of excessive TNF-α has been reported (Black et al., Annual Reports in Medicinal Chemistry, Vol. 32, pp. 241-250 (1997)).

As regards the relationship between TNF-α and pathology, for example, abnormal production of inflammatory-cytokines, such as TNF-α, interleukin 1β, interleukin 6 and the like, is considered to be the cause of systemic inflammatory response syndromes including sepsis, septic shock and multiple organ dysfunction syndrome (MODS), where neutralization of TNF-α can suppress increase in interleukin 1β and interleukin 6 in blood (Tracey et al., Nature, vol. 0.330, pp. 662-664 (1987)).

Moreover, there is a report stating that insulin resistance induced by obesity is improved in TNF-α deficient animals, suggesting the relationship between TNF-α and non-insulin dependent diabetes mellitus (NIDDM) (Uysal et al., Nature, vol. 389, pp. 610-614 (1997)).

Incidentally, it has been clarified in the field of autoimmune diseases that TNF-α causes disorders of neurocyte and oligodendrocyte, and that TNF-α plays a role of an effecter of neurodegeneration and demyelination (Suzumura, *IGAKU NO AYUMI*, vol. 185, pp. 931-935 (1998)).

Moreover, detection of a large amount of TNF-α in the synovial fluid of chronic articular rheumatism patients has been also reported (Saxne et al., Arthritis Rheumatism, vol. 31, pp. 1041-1045 (1998)).

Other than the above, involvement of TNF-α has been pointed out as a causative factor of Crohn's disease, fulminant hepatitis, cachexia, bone resorption disorder, cardiac infarction, allergic disease and adult respiratory distress syndrome.

TNF-α is closely related to the onset and aggravation of various diseases, and therefore, suppression of the action of TNF-α is considered to afford treatment of such diseases.

At present, steroidal hormone preparations and non-steroidal anti-inflammatory drugs have been applied to some of the inflammatory diseases. However, harmful side effects may be induced, because the sites of action thereof range widely and the TNF-α suppressive action is not a specific one. Particularly, the side effects of steroids pose medical problems. In addition, there is an in vitro experiment report indicating that pharmaceutical agents having a phosphodiesterase inhibitory action suppress TNF-α production. However, the effect thereof in the body is very weak and clinical application is considered to be difficult (Suzumura, mentioned above (1998)). Furthermore, a treatment using a TNF-α antibody or soluble TNF-α receptor, which is a peptidic polymer compound, shows fine clinical results in chronic articular rheumatism, Crohn's disease and the like, but the treatment effect is not long-lasting except in some patients.

In view of the present situation, the development of a pharmaceutical agent for the prophylaxis or treatment of various diseases considered to be caused by abnormal production of TNF-α, which specifically suppresses TNF-α production and which shows a superior treatment effect in the body has been demanded.

However, as heterocyclic compounds represented by the formula (I) to be mentioned later, for example, J. Am. Chem. Soc., 81, pp. 2456-2464 (1959) and J. Org. Chem. 24, pp. 963-964 (1959) describe compounds of the following formulas

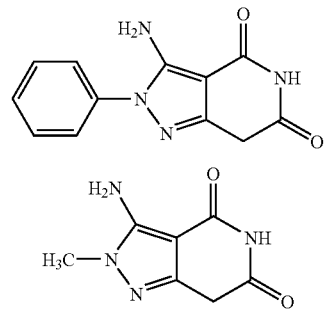

but do not describe bioactivity. In addition, Tetrahedron 30(16), pp. 2791-2796 (1974) describes compounds of the following formulas

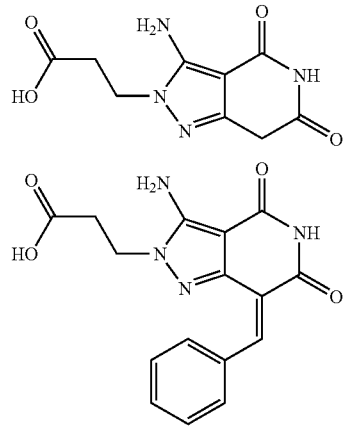

but does not describe bioactivity. Moreover, Indian J. Chem, 5(10), pp. 464-466 (1967) describes compounds of the following formulas

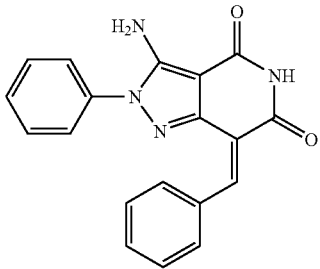

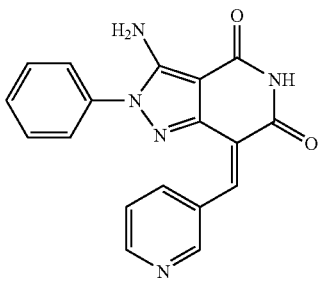

and a compound of the following formula

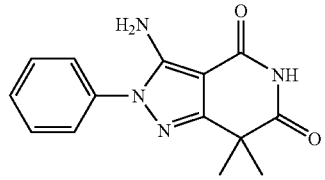

but does not describe bioactivity.

In addition, Bull. Chem. Soc. Jpn., 46, pp. 1801-1803 (1973) describes compounds of the following formulas

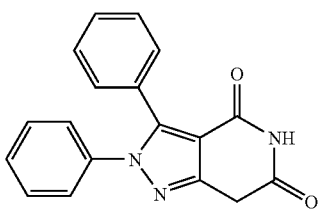

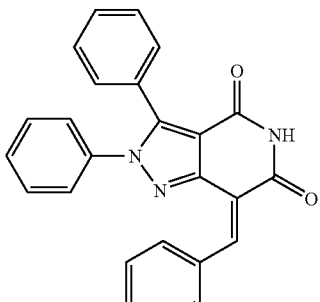

R = H, Cl

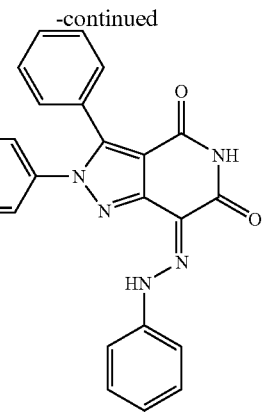

but again, does not describe bioactivity. In other words, use of a heterocyclic compound represented by the formula (I) as a pharmaceutical agent is not reported.

DISCLOSURE OF THE INVENTION

An object of the present invention is to provide a novel compound having an inhibitory activity on TNF-α production, a novel TNF-α production inhibitor and pharmaceutical use of a compound having a particular structure, which includes said novel compound.

The present inventors have conducted intensive studies with the aim of achieving the above-mentioned object, and succeeded in obtaining a compound having a TNF-α production inhibitory action, and also found that some of known compounds also have such action. They have further found that these compounds have a superior TNF-α production inhibitory ability in living organisms, or a treatment effect in an inflammatory disease model, which resulted in the completion of the present invention. Accordingly, the present invention provides the following.

(1) A pharmaceutical composition containing a heterocyclic compound represented by the formula (I)

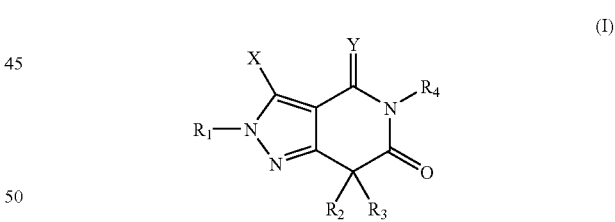

(I)

wherein $R_1$ is an alkyl group optionally having substituent(s), a cycloalkyl group optionally having substituent(s), a cycloalkylalkyl group optionally having substituent(s), an aralkyl group optionally having substituent(s), an aryl group optionally having substituent(s), a heteroaryl group optionally having substituent(s), a heteroarylalkyl group optionally having substituent(s), a cycloalkyl group containing hetero atom(s) in its ring optionally having substituent(s) or a cycloalkylalkyl group containing hetero atom(s) in its ring, $R_2$ and $R_3$ are the same or different and each is a hydrogen atom, a hydroxyl group, an alkyl group optionally having substituent(s) or an aralkyl group optionally having substituent(s), or may in combination form a cycloalkyl group, a cycloalkyl group containing hetero atom(s) in its ring, or

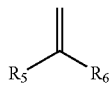

wherein $R_5$ and $R_6$ are the same or different and each is a hydrogen atom, an alkoxy group, an alkoxycarbonyl group, an alkyl group optionally having substituent(s), a cycloalkyl group optionally having substituent(s), a cycloalkyl group containing hetero atom(s) in its ring, an aralkyl group optionally having substituent(s), an aryl group optionally having substituent(s) or a heteroaryl group optionally having substituent(s), or may be linked to form a cycloalkyl group or a cycloalkyl group containing hetero atom(s) in its ring,

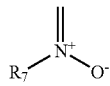

wherein $R_7$ is an aryl group optionally having substituent (s), =N—$R_8$ wherein $R_8$ is a hydroxyl group, an alkoxy group, an aryl group optionally having substituent(s) or a heteroaryl group optionally having substituent(s), =N—NH—$R_9$ wherein $R_9$ is an aryl group optionally having substituent(s), a heteroaryl group optionally having substituent(s), an acyl group or a carbamoyl group, or =O, $R_4$ is a hydrogen atom, an alkyl group optionally having substituent(s) or an aralkyl group optionally having substituent(s), X is a hydrogen atom, a halogen atom, a hydroxyl group, an alkyl group optionally having substituent(s), an aralkyl group optionally having substituent(s), an alkoxy group optionally having substituent(s), an aryl group optionally having substituent(s), a heteroaryl group optionally having substituent(s), an amino group optionally having substituent(s), an alkylthio group optionally having substituent(s), an aralkylthio group optionally having substituent(s), an arylthio group optionally having substituent(s), a heteroarylthio group optionally having substituent(s), an alkylsulfonyl group optionally having substituent(s), an aralkylsulfonyl group optionally having substituent(s), an arylsulfonyl group optionally having substituent(s), a heteroarylsulfonyl group optionally having substituent(s), —N=CH—O-Alk wherein Alk is an alkyl group, or an alkoxycarbonylthio group, and Y is an oxygen atom or a sulfur atom,
an isomer thereof, a solvate thereof or a pharmaceutically acceptable salt thereof as an active ingredient.

(2) The pharmaceutical composition of the above-mentioned (1), wherein, in the formula (I), $R_1$ is an alkyl group optionally having substituent(s), a cycloalkyl group optionally having substituent(s), a cycloalkylalkyl group optionally having substituent(s), an aralkyl group optionally having substituent(s), an aryl group optionally having substituent(s) or a heteroaryl group optionally having substituent(s).

(3) The pharmaceutical composition of the above-mentioned (1) or (2), wherein, in the formula (I);

$R_4$ is a hydrogen atom,

X is a halogen atom, an amino group optionally having substituent(s), an alkylthio group optionally having substituent(s), an aralkylthio group optionally having substituent(s), an arylthio group optionally having substituent(s) or a heteroarylthio group optionally having substituent(s), and Y is an oxygen atom.

(4) The pharmaceutical composition of the above-mentioned (3), wherein, in the formula (I), $R_1$ is an aryl group optionally having substituent(s) or a heteroaryl group optionally having substituent(s), $R_2$ and $R_3$ may together represent

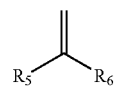

wherein $R_5$ and $R_6$ are the same or different and each is a hydrogen atom, an alkoxy group, an alkoxycarbonyl group, an alkyl group optionally having substituent(s), a cycloalkyl group optionally having substituent(s), a cycloalkyl group containing hetero atom(s) in its ring, an aralkyl group optionally having substituent(s), an aryl group optionally having substituent(s) or a heteroaryl group optionally having substituent(s), or may be linked to form a cycloalkyl group or a cycloalkyl group containing hetero atom(s) in its ring, and X is a halogen atom or an amino group optionally having substituent(s).

(5) The pharmaceutical composition of the above-mentioned (4), wherein $R_1$ is a phenyl group optionally having substituent(s), and X is an amino group.

(6) The pharmaceutical composition of the above-mentioned (1), wherein, in the formula (I), $R_2$ and $R_3$ are each a hydrogen atom, $R_4$ is a hydrogen atom, X is a halogen atom or an amino group optionally having substituent(s), and Y is an oxygen atom.

(7) The pharmaceutical composition of the above-mentioned (6), wherein X is an amino group.

(8) The pharmaceutical composition of the above-mentioned (1), wherein, in the formula (I), $R_1$ is an alkyl group optionally having substituent(s), a cycloalkyl group optionally having substituent(s), a cycloalkylalkyl group, an aralkyl group optionally having substituent(s), an aryl group optionally having substituent(s), a heteroaryl group, a heteroarylalkyl group or a cycloalkyl group containing hetero atom(s) in its ring optionally having substituent(s), $R_2$ and $R_3$ are the same or different and each is a hydrogen atom, a hydroxyl group, an alkyl group optionally having substituent(s) or an aralkyl group optionally having substituent(s), or may be linked to form a cycloalkyl group,

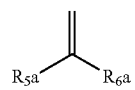

wherein $R_5a$ and $R_6a$ are the same or different and each is a hydrogen atom, an alkoxycarbonyl group, an alkyl group optionally having substituent(s), a cycloalkyl group, an aryl group optionally having substituent(s) or a heteroaryl group optionally having substituent(s), or may be linked to form a cycloalkyl group or a cycloalkyl group containing hetero atom(s) in its ring,

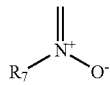

wherein $R_7$ is an aryl group optionally having substituent(s), =N—$R_8$a wherein $R_8$a is a hydroxyl group, an alkoxy group or an aryl group optionally having substituent(s), =N—NH—$R_9$a wherein $R_9$a is an aryl group optionally having substituent(s), an acyl group or a carbamoyl group, or =O, $R_4$ is a hydrogen atom, an alkyl group or an aralkyl group, and X is a hydrogen atom, a halogen atom, a hydroxyl group, an aryl group optionally having substituent(s), a heteroaryl group optionally having substituent(s), an amino group optionally having substituent(s), an alkylthio group optionally having substituent(s), an aralkylthio group, an arylthio group optionally having substituent(s), an alkylsulfonyl group, an arylsulfonyl group optionally having substituent(s), —N=CH—O-Alk wherein Alk is an alkyl group, or an alkoxycarbonylthio group.

(9) The pharmaceutical composition of the above-mentioned (1), wherein the heterocyclic compound represented by the formula (I), an isomer thereof, a solvate thereof or a pharmaceutically acceptable salt thereof is a heterocyclic compound represented by the following formula

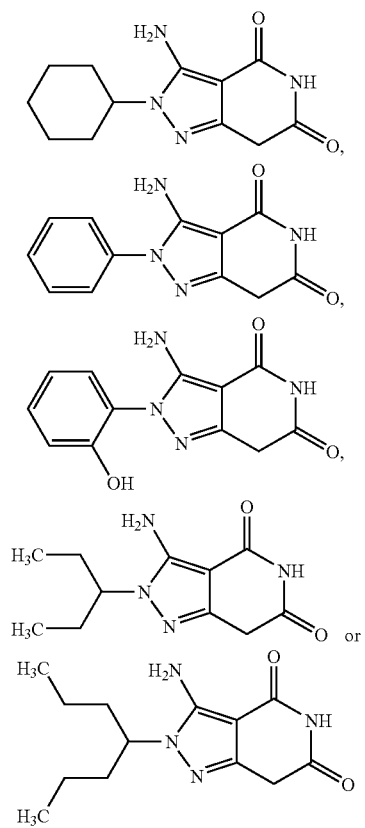

an isomer thereof, a solvate thereof or a pharmaceutically acceptable salt thereof.

(10) The pharmaceutical composition of any of the above-mentioned (1)-(9), which is a TNF-α production inhibitor.

(11) The pharmaceutical composition of any of the above-mentioned (1)-(9), which is used for the prophylaxis or treatment of a disease wherein inhibition of TNF-α production is effective.

(12) The pharmaceutical composition of any of the above-mentioned (1)-(11), which is used for the prophylaxis or treatment of at least one kind selected from the group consisting of Crohn's disease, ulcerative colitis, sepsis, chronic articular rheumatism and an autoimmune disease.

(13) A heterocyclic compound represented by the formula (I')

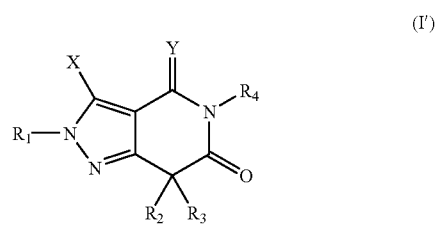

wherein $R_1$ is an alkyl group optionally having substituent(s), a cycloalkyl group optionally having substituent(s), a cycloalkylalkyl group optionally having substituent(s), an aralkyl group optionally having substituent(s), an aryl group optionally having substituent(s), a heteroaryl group optionally having substituent(s), a heteroarylalkyl group optionally having substituent(s), a cycloalkyl group containing hetero atom(s) in its ring optionally having substituent(s) or a cycloalkylalkyl group containing hetero atom(s) in its ring, $R_2$ and $R_3$ are the same or different and each is a hydrogen atom, a hydroxyl group, an alkyl group optionally having substituent(s) or an aralkyl group optionally having substituent(s), or may be linked to form a cycloalkyl group, a cycloalkyl group containing hetero atom(s) in its ring,

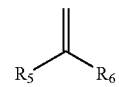

wherein $R_5$ and $R_6$ are the same or different and each is a hydrogen atom, an alkoxy group, an alkoxycarbonyl group, an alkyl group optionally having substituent(s), a cycloalkyl group optionally having substituent(s), a cycloalkyl group containing hetero atom(s) in its ring, an aralkyl group optionally having substituent(s), an aryl group optionally having substituent(s) or a heteroaryl group optionally having substituent(s), or may be linked to form a cycloalkyl group or a cycloalkyl group containing hetero atom(s) in its ring,

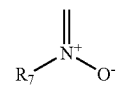

wherein $R_7$ is an aryl group optionally having substituent(s), =N—$R_8$ wherein $R_8$ is a hydroxyl group, an alkoxy group, an aryl group optionally having substituent(s) or a heteroaryl group optionally having substituent(s), =N—NH—$R_9$ wherein $R_9$ is an aryl group optionally having substituent(s), a heteroaryl group optionally having substituent(s), an acyl group or a carbamoyl group, or =O, $R_4$ is a hydrogen atom, an alkyl group optionally having substituent(s) or an aralkyl group optionally having substituent(s), X is a hydrogen atom, a halogen atom, a hydroxyl group, an alkyl group optionally having substituent(s), an aralkyl group optionally having substituent(s), an alkoxy group optionally having substituent(s), an aryl group optionally having substituent(s), a heteroaryl group optionally having substituent(s), an amino group optionally having substituent(s), an alkylthio group optionally having substituent(s), an aralkylthio group optionally having substituent(s), an arylthio group optionally having substituent(s), a heteroarylthio group optionally having substituent(s), an alkylsulfonyl group optionally having substituent(s), an aralkylsulfonyl group optionally having substituent(s), an arylsulfonyl group optionally having substituent(s), a heteroarylsulfonyl group optionally having substituent(s), —N=CH—O-Alk wherein Alk is an alkyl group, or an alkoxycarbonylthio group, and Y is an oxygen atom or a sulfur atom, provided that, when Y is an oxygen atom, $R_1$ is a phenyl group or a 2-carboxyethyl group or a methyl group, and X is an amino group, then all of $R_2$, $R_3$ and $R_4$ are not hydrogen atoms at the same time;

when Y is an oxygen atom, $R_1$ is a phenyl group, X is an amino group and $R_4$ is a hydrogen atom, then both $R_2$ and $R_3$ are not methyl groups at the same time;

when Y is an oxygen atom, $R_1$ is a phenyl group, X is an amino group, $R_4$ is a hydrogen atom and one of $R_5$ and $R_6$ is a hydrogen atom, then the other of $R_5$ and $R_6$ is not a phenyl group or a 3-pyridyl group;

when Y is an oxygen atom, $R_1$ is a phenyl group, X is a phenyl group and $R_4$ is a hydrogen atom, then both $R_2$ and $R_3$ are not hydrogen atoms at the same time or are not linked to form =N—NH—$R_9'$ (wherein $R_9'$ is a phenyl group);

when Y is an oxygen atom, $R_1$ is a phenyl group, X is a phenyl group, $R_4$ is a hydrogen atom and one of $R_5$ and $R_6$ is a hydrogen atom, then the other of $R_5$ and $R_6$ is not a phenyl group or a 4-chlorophenyl group; and when Y is an oxygen atom, $R_1$ is a 2-carboxyethyl group, X is an amino group, $R_4$ is a hydrogen atom and one of $R_5$ and $R_6$ is a hydrogen atom, then the other of $R_5$ and $R_6$ is not a phenyl group, an isomer thereof, a solvate thereof or a pharmaceutically acceptable salt thereof.

(14) The heterocyclic compound of the above-mentioned (13), wherein, in the formula (I'),
$R_1$ is an alkyl group optionally having substituent(s), a cycloalkyl group optionally having substituent(s), a cycloalkylalkyl group optionally having substituent(s), an aralkyl group optionally having substituent(s), an aryl group optionally having substituent(s) or a heteroaryl group optionally having substituent(s), an isomer thereof, a solvate thereof or a pharmaceutically acceptable salt thereof.

(15) The heterocyclic compound of the above-mentioned (13) or (14), wherein, in the formula (I'),
$R_4$ is a hydrogen atom,
X is a halogen atom, an amino group optionally having substituent(s), an alkylthio group optionally having substituent(s), an aralkylthio group optionally having substituent(s), an arylthio group optionally having substituent(s) or a heteroarylthio group optionally having substituent(s), and
Y is an oxygen atom,
an isomer thereof, a solvate thereof or a pharmaceutically acceptable salt thereof.

(16) The heterocyclic compound of the above-mentioned (15), wherein, in the formula (I'), $R_1$ is an aryl group optionally having substituent(s) or a heteroaryl group optionally having substituent(s),
$R_2$ and $R_3$ may, in combination, form

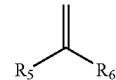

wherein $R_5$ and $R_6$ are the same or different and each is a hydrogen atom, an alkoxy group, an alkoxycarbonyl group, an alkyl group optionally having substituent(s), a cycloalkyl group optionally having substituent(s), a cycloalkyl group containing hetero atom(s) in its ring, an aralkyl group optionally having substituent(s), an aryl group optionally having substituent(s) or a heteroaryl group optionally having substituent(s), or may be linked to form a cycloalkyl group or a cycloalkyl group containing hetero atom(s) in its ring, and X is a halogen atom or an amino group optionally having substituent(s), an isomer thereof, a solvate thereof or a pharmaceutically acceptable salt thereof.

(17) The heterocyclic compound of the above-mentioned (16), wherein $R_1$ is a phenyl group optionally having substituent(s), and X is an amino group, an isomer thereof, a solvate thereof or a pharmaceutically acceptable salt thereof.

(18) The heterocyclic compound of the above-mentioned (13), wherein, in the formula (I'),
$R_2$ and $R_3$ are hydrogen atoms,
$R_4$ is a hydrogen atom,
X is a halogen atom or an amino group optionally having substituent(s), and
Y is an oxygen atom,
an isomer thereof, a solvate thereof or a pharmaceutically acceptable salt thereof.

(19) The heterocyclic compound of the above-mentioned (18), wherein X is an amino group,
an isomer thereof, a solvate thereof or a pharmaceutically acceptable salt thereof.

(20) The heterocyclic compound of the above-mentioned (13), wherein, in the formula (I'),
$R_1$ is an alkyl group optionally having substituent(s), a cycloalkyl group optionally having substituent(s), a cycloalkylalkyl group, an aralkyl group optionally having substituent(s), an aryl group optionally having substituent(s), a heteroaryl group, a heteroarylalkyl group or a cycloalkyl group containing hetero atom(s) in its ring optionally having substituent(s),
$R_2$ and $R_3$ are the same or different and each is a hydrogen atom, a hydroxyl group, an alkyl group optionally having substituent(s) or an aralkyl group optionally having substituent(s), or may, in combination, form a cycloalkyl group,

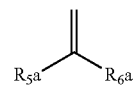

wherein $R_5a$ and $R_6a$ are the same or different and each is a hydrogen atom, an alkoxycarbonyl group, an alkyl group optionally having substituent(s), a cycloalkyl group, an aryl group optionally having substituent(s) or a heteroaryl group optionally having substituent(s), or may be linked to form a cycloalkyl group or a cycloalkyl group containing hetero atom(s) in its ring,

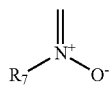

wherein $R_7$ is an aryl group optionally having substituent(s), =N—$R_8$a wherein $R_8$a is a hydroxyl group, an alkoxy group or an aryl group optionally having substituent(s)), =N—NH—$R_9$a wherein $R_9$a is an aryl group optionally having substituent(s), an acyl group or a carbamoyl group, or =O, $R_4$ is a hydrogen atom, an alkyl group or an aralkyl group, and X is a hydrogen atom, a halogen atom, a hydroxyl group, an aryl group optionally having substituent(s), a heteroaryl group optionally having substituent(s), an amino group optionally having substituent(s), an alkylthio group optionally having substituent(s), aralkylthio group, an arylthio group optionally having substituent(s), an alkylsulfonyl group, an arylsulfonyl group optionally having substituent(s), —N=CH—O-Alk wherein Alk is an alkyl group or an alkoxycarbonylthio group, an isomer thereof, a solvate thereof or a pharmaceutically acceptable salt thereof.

(21) A heterocyclic compound represented by the formula

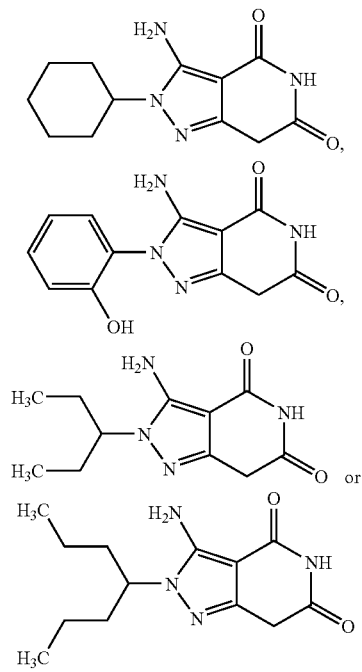

an isomer thereof, a solvate thereof or a pharmaceutically acceptable salt thereof.

(22) A pharmaceutical composition containing the heterocyclic compound of any of the above-mentioned (13)-(21), an isomer thereof, a solvate thereof or a pharmaceutically acceptable salt thereof, as an active ingredient.

The present invention further relates to a method for the prophylaxis or treatment of a disease in which inhibition of TNF-α production is effective, which comprises administering an effective amount of a compound of the formula (I) or the formula (I') to a patient, and use of a compound of the formula (I) or the formula (I') for the production of a pharmaceutical agent for the prophylaxis or treatment of a disease in which inhibition of TNF-α production is effective. Moreover, the present invention provides a commercial package comprising a compound of the formula (I) or the formula (I') and a written matter associated therewith, the written matter stating that said compound can or should be used for the prophylaxis or treatment of a disease in which inhibition of TNF-α production is effective.

The amount of TNF-α induced by lipopolysaccharide (LPS) stimulation is shown in the concentration in serum. The administration of the compound of the present invention remarkably decreased the concentration of TNF-α in serum.

Figure 2:
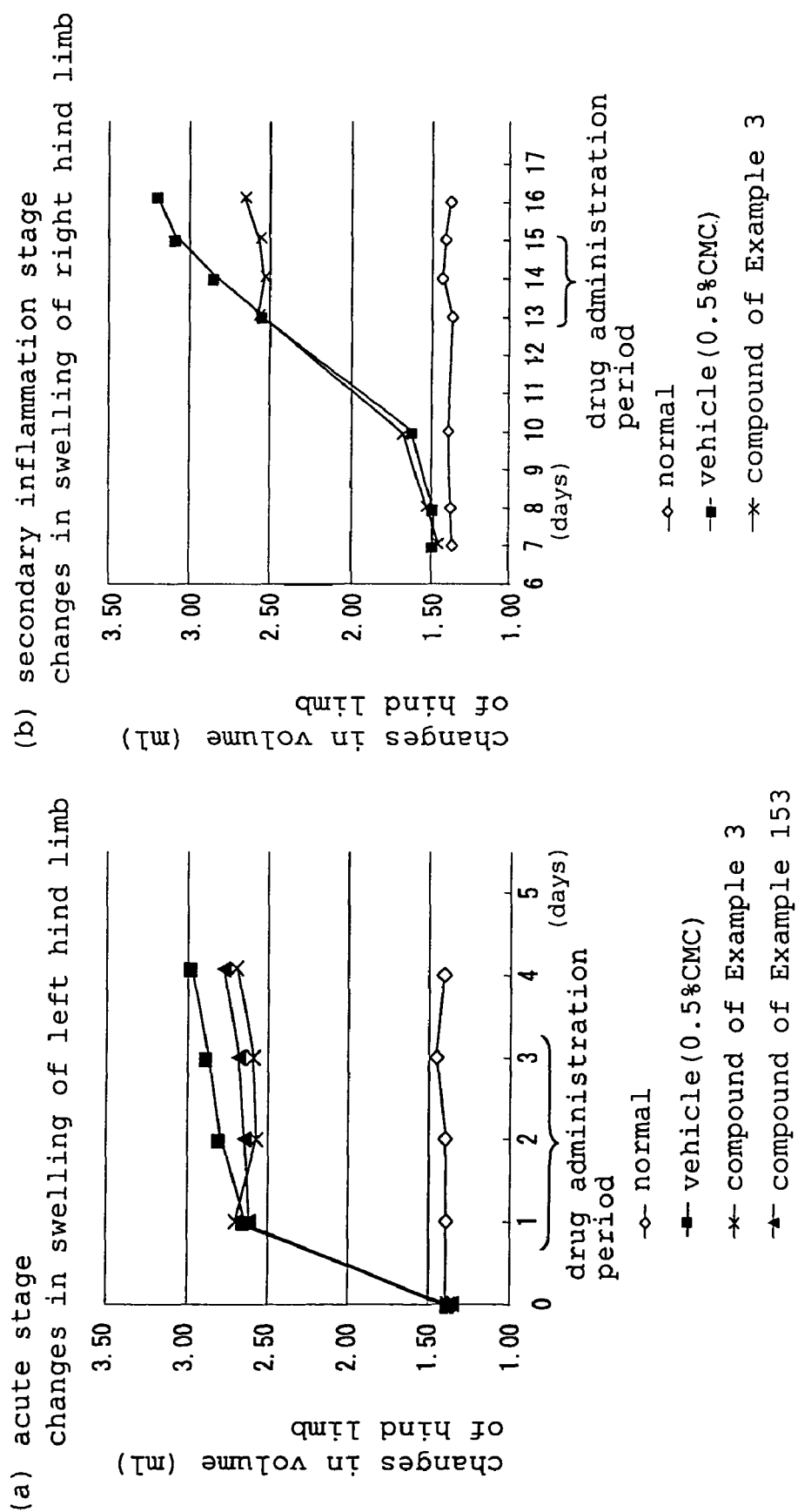

FIG. 2 is a graph showing the results of the efficacy (suppression of swelling of joint) test in rat adjuvant arthritis models.

The changes in the volume of left hind limb where an adjuvant was injected was measured as an index of acute inflammation in the joint (FIG. 2-a). As an index of secondary inflammation, the changes in the volume of right hind limb (opposite limb) was measured (FIG. 2-b). The administration of the compound of the present invention remarkably suppressed the swelling of joint in the acute stage and secondary inflammation stage.

DETAILED DESCRIPTION OF THE INVENTION

In the present invention, by "a disease wherein inhibition of TNF-α production is effective" is meant a disease for which TNF-α activity is inconvenient, and inhibition of the TNF-α activity is expected to alleviate the symptoms and/or progress of the disease. To be precise, it is a disease where the presence of TNF-α in patients suffering from the disease has been elucidated to be the pathology of the physiological condition of the disease or a factor contributing to the aggravation of the disease, or suspected to be such factor. As such disease, septic shock, sepsis, endotoxic shock, hemodynamic shock, post ischemic reperfusion injury, meningitis, psoriasis, congestive cardiomyopathy, fibrosis, hepatitis, non-insulin dependent diabetes mellitus (NIDDM), graft rejection, graft versus host disease, cancer, cachexia, autoimmune disease (systemic lupus erythematosus, rheumatic disease, allergy, multiple sclerosis, autoimmune uveitis, nephrotic syndrome, type I diabetes (IDDM) etc.), arthritis (chronic articular rheumatism, rheumatoid spondylitis, osteoarthritis and other arthritises), inflammatory bone disease, bone resorption disorder, Behcet's syndrome, infectious disease (opportunistic infectious disease in AIDS, cerebral malaria, mycobacteria infectious disease and the like), Crohn's disease, ulcerative colitis, erythema nodosum leprosy (ENL in leprosy), disorders by radiation (radiation damage), and damage on alveolar due to hyperoxidation and the like, particularly, Crohn's disease, ulcerative colitis, sepsis, chronic articular rheumatism, autoimmune disease and the like, can be mentioned, but not limited to them.

In the present invention, with regard to the "inhibition of TNF-α production", the action mechanism thereof is not particularly limited as long as the secretion of TNF-α from TNF-α producing cells such as macrophage, macrophage-like cells (kupffer's cell and microglia), neutrophile, basophil, acidophil, lymphocyte, NK cell, LAK cell, mast cell, myeloma cell, fibroblast, astrocyte, keratinocyte and the like is suppressed, wherein the expression may be suppressed at the gene level, or the expression may be suppressed at the protein level. The inhibition of the TNF-α production can be confirmed by a known means such as an assay by sandwich ELISA (*Men-eki Jikken Sousahou* I•II Shunsuke Migita, Susumu Konda, Tasuku Honjyo, Toshiyuki Hamaoka Ed., Nankodo Co., Ltd, 1995) of cell culture supernatant or serum, and the like.

The present invention provides novel use of heterocyclic compound represented by the formula (I), particularly use as a pharmaceutical agent. More particularly, it provides novel use as a TNF-α production inhibitor or a pharmaceutical composition for the prophylaxis or treatment of various diseases considered to be caused by abnormal production and activity of TNF-α.

In the present invention, the compound of the formula (I) encompasses known compounds. Of the compounds represented by the formula (I), the compound represented by the formula (I') is a novel compound. Accordingly, a simple reference by a compound of the formula (I) in the present specification encompasses compounds represented by the formula (I').

Each functional group of the compound of the present invention is explained in detail in the following.

The "halogen atom" means fluorine atom, chlorine atom, bromine atom, iodine atom and the like.

The "hetero atom" means oxygen atom, nitrogen atom, sulfur atom and the like.

The "alkyl group" means a straight chain or branched alkyl group having 1 to 10 carbon atoms, which is specifically exemplified by methyl group, ethyl group, n-propyl group, isopropyl group, n-butyl group, isobutyl group, sec-butyl group, tert-butyl group, n-pentyl group, isopentyl group, tert-pentyl group, neopentyl group, 2-pentyl group, 3-pentyl group, n-hexyl group, 2-hexyl group, n-heptyl group, 2-heptyl group, n-octyl group, 2-octyl group, n-nonanyl group, 2-nonanyl group, n-decanyl group, 2-decanyl group and the like.

The "alkyl group optionally having substituent(s)" means an alkyl group (defined above) optionally substituted by one or more substituents, wherein the "substituent" is exemplified by halogen atom, alkoxy group, hydroxyl group, carboxyl group, alkoxycarbonyl group, aralkyloxycarbonyl group, amino group optionally having substituent(s), aminocarbonyl group, aralkylaminocarbonyl group, alkylthio group and the like. The detail of each substituent is as defined separately in the present specification.

The "cycloalkyl group" means a cyclic alkyl group having 3 to 7 carbon atoms, which is specifically exemplified by cyclopropyl group, cyclobutyl group, cyclopentyl group, cyclohexyl group, cycloheptyl group and the like.

The "cycloalkyl group optionally having substituent(s)" means a cycloalkyl group (as defined above) optionally substituted by one or more substituents, wherein the "substituent" is exemplified by halogen atom, alkyl group, alkoxy group, aralkyloxycarbonyl group, hydroxyl group, carboxyl group, alkoxycarbonyl group, amino group optionally having substituent(s), aminocarbonyl group, aralkylaminocarbonyl group, alkylthio group and the like. The detail of each substituent is as defined separately in the present specification.

The "cycloalkylalkyl group" is that wherein the alkyl group is substituted by cycloalkyl group. Specific examples thereof include cyclopropylmethyl group, cyclobutylmethyl group, cyclopentylmethyl group, cyclohexylmethyl group, cycloheptylmethyl group and the like.

The "cycloalkylalkyl group optionally having substituent(s)" means a cycloalkylalkyl group (as defined above) optionally substituted by one or more substituents, wherein the "substituent" is exemplified by halogen atom, alkoxy group, aralkyloxycarbonyl group, hydroxyl group, carboxyl group, alkoxycarbonyl group, amino group optionally having substituent(s), aminocarbonyl group, aralkylaminocarbonyl group, alkylthio group and the like. The detail of each substituent is as defined separately in the present specification.

The "cycloalkyl group containing hetero atom(s) in its ring" means a cyclic alkyl group having 3 to 7 carbon atoms, which contains at least one hetero atom. Specific examples thereof include pyrrolizinyl group, pyrrolinyl group, piperidinyl group, piperazinyl group, morpholinyl group, tetrahydrofuranyl group, tetrahydropyranyl group, thiazolidinyl group, imidazolidinyl group and the like.

The "cycloalkyl group containing hetero atom(s) in its ring optionally having substituent(s)" means a cycloalkyl group containing hetero atom(s) in its ring (as defined above), which is optionally substituted by one or more substituents, wherein the "substituent" is exemplified by alkyl group, halogen atom, hydroxyl group, alkoxy group, amino group optionally having substituent(s) (amino group, substituted amino group), carboxyl group and the like. In the cycloalkyl group containing hetero atom(s) in its ring, two or more substituents may be linked and form a ring, together with the adjacent hetero atom or carbon atom. Examples thereof include fused rings of carbon ring and hetero ring, such as indolinyl group, isoindolinyl group, chromanyl group, isochromanyl group and the like.

The "cycloalkylalkyl group containing hetero atom(s) in its ring" means an alkyl group (as defined above) substituted by cycloalkyl group containing hetero atom(s) in its ring (as defined above). Specific examples thereof include piperidinomethyl group, piperazinomethyl group, morpholinomethyl group, tetrahydropyranylmethyl group, tetrahydrofuranylmethyl group and the like.

The "aryl group" means a monocycle-tricyclic aryl group having 6 to 14 carbon atoms. Specific examples thereof include phenyl group, naphthyl group, anthryl group, phenanthryl group, biphenyl group and the like.

The "aryl group optionally having substituent(s)" means an aryl group (as defined above) optionally substituted by one or more substituents, wherein the "substituent" is exemplified by halogen atom, alkyl group, alkoxy group, haloalkoxy group, hydroxyl group, nitro group, carboxyl group, aralkylaminocarbonyl group, haloaralkylaminocarbonyl group, aralkyloxycarbonyl group, alkylaminocarbonyl group, alkoxycarbonyl group, amino group optionally having substituent(s) and the like. The detail of each substituent is as defined separately in the present specification.

The "aralkyl group" means an alkyl group (as defined above) substituted by aryl group (as defined above). Specific examples thereof include benzyl group, trityl group, phenethyl group, 3-phenylpropyl group, 2-phenylpropyl group, 4-phenylbutyl group, biphenylmethyl group and the like.

The "aralkyl group optionally having substituent(s)" means an aralkyl group (as defined above) optionally substituted by one or more substituents, wherein the "substituent" is exemplified by halogen atom, hydroxyl group, alkyl group, carboxyl group, alkoxy group, nitro group, alkoxycarbonyl group, sulfo group, cyano group and the like. The detail of each substituent is as defined separately in the present specification.

The "heteroaryl group" means an aromatic heterocyclic group having 1 to 13 carbon atoms, which has one or more hetero atoms selected from oxygen atom, nitrogen atom and sulfur atom and which may form a fused ring. Specific examples thereof include aromatic heterocyclic groups such as pyridyl group, pyrrolyl group, furyl group, thienyl group, pyrazolyl group, imidazolyl group, indolyl group, quinolyl group, oxadiazolyl group, thiadiazolyl group, triazolyl group, oxazolyl group, thiazolyl group, triazinyl group, pyrazinyl group, pyridazinyl group, pyrimidinyl group and the like.

The "heteroaryl group optionally having substituent(s)" means a heteroaryl group optionally substituted by one or more substituents, wherein the "substituent" is exemplified by halogen atom, alkyl group, hydroxyl group, alkoxy group, haloalkoxy group, nitro group, carboxyl group, aralkylaminocarbonyl group, haloaralkylaminocarbonyl group, alkylaminocarbonyl group, an alkoxycarbonyl group, an amino group optionally having substituent(s) and the like. The detail of each substituent is as defined separately in the present specification.

The "heteroarylalkyl group" means an alkyl group substituted by heteroaryl group (as defined above). Specific examples thereof include 2-picolyl group, 3-picolyl group, 4-picolyl group and the like.

The "heteroarylalkyl group optionally having substituent(s)" means a heteroarylalkyl group (as defined above) optionally substituted by one or more substituents, wherein the "substituent" is exemplified by alkyl group, halogen atom, hydroxyl group, alkoxy group, amino group optionally having substituent(s) (amino group, substituted amino group), carboxyl group, nitro group and the like. The detail of each substituent is as defined separately in the present specification.

The "alkoxy group" means a straight chain or branched alkoxy group having 1 to 6 carbon atoms. Specific examples thereof include methoxy group, ethoxy group, n-propoxy group, isopropoxy group, n-butoxy group, isobutoxy group, sec-butoxy group, tert-butoxy group, n-pentyloxy group, isopentyloxy group, tert-pentyloxy group, neopentyloxy group, 2-pentyloxy group, 3-pentyloxy group, n-hexyloxy group, 2-hexyloxy group and the like.

The "alkoxy group optionally having substituent(s)" means an alkoxy group (as defined above) optionally substituted by one or more substituents, wherein the "substituent" is exemplified by alkoxy group, hydroxyl group, carboxyl group, alkoxycarbonyl group, amino group optionally having substituent(s), aminocarbonyl group, aralkylaminocarbonyl group, alkylthio group and the like. The detail of each substituent is as defined separately in the present specification.

The "haloalkoxy group" means the above-mentioned alkoxy group substituted by one or more halogen atoms (as defined above). Specific examples thereof include fluoromethoxy group, chloromethoxy group, bromomethoxy group, difluoromethoxy group, dichloromethoxy group, trichloromethoxy group, trifluoromethoxy group, fluoroethoxy group, chloroethoxy group, bromoethoxy group, difluoroethoxy group, dichloroethoxy group, dibromoethoxy group, trifluoroethoxy group, trichloroethoxy group, trifluoroethoxy group and the like.

The "alkoxycarbonyl group" means a straight chain or branched alkoxycarbonyl group having 2 to 5 carbon atoms. Specific examples thereof include methoxycarbonyl group, ethoxycarbonyl group, propoxycarbonyl group, isopropoxycarbonyl group, butoxycarbonyl group, isobutoxycarbonyl group, sec-butoxycarbonyl-group, tert-butoxycarbonyl group and the like.

The "aralkyloxycarbonyl group" means an alkoxycarbonyl group substituted by aryl group, where the aryl group and the alkoxycarbonyl group are each exemplified by those mentioned above. Specific examples thereof include benzyloxycarbonyl group, trityloxycarbonyl group, phenethyloxycarbonyl group, 3-phenylpropyloxycarbonyl group, 2-phenylpropyloxycarbonyl group, 4-phenylbutyloxycarbonyl group, biphenylmethyloxycarbonyl group and the like.

The "acyl group" means an acyl group having a straight chain or branched alkyl group having 1 to 6 carbon atoms or cycloalkyl group, or an aryl group. As the straight chain or branched alkyl group having 1 to 6 carbon atoms, those having 6 or less carbon atoms, from among those mentioned for the aforementioned "alkyl group", can be mentioned. The cycloalkyl group and aryl group are each exemplified by those mentioned above. The alkyl moiety, cycloalkyl moiety and aryl moiety in the acyl group may each have a substituent, where the substituent is exemplified by those mentioned above. Specific examples of the acyl group include formyl group, acetyl group, propionyl group, butyroyl group, isobutyroyl group, valeroyl group, isovaleroyl group, pivaloyl group, hexanoyl group, acryloyl group, methacryloyl group, crotonoyl group, isocrotonoyl group, benzoyl group, naphthoyl group and the like.

The "amino group optionally having substituent(s)" means an amino group optionally substituted by one or more substituents, wherein the "substituent" is exemplified by alkyl group, aralkyl group optionally having substituent(s), acyl group, cycloalkyl group, cycloalkylalkyl group, alkoxycarbonyl group, aralkyloxycarbonyl group and the like. The detail of each substituent is as defined separately in the present specification. These substituents may form a ring together with the nitrogen atom they are attached to. When a ring is formed, 1-piperidyl group, 1-piperazyl group, morpholin-4-yl group and the like can be mentioned.

The "alkylthio group" means a thio group substituted by a straight chain or branched alkyl group having 1 to 6 carbon atoms. Specific examples thereof include methylthio group, ethylthio group, propylthio group, isopropylthio group, n-butylthio group, isobutylthio group, sec-butylthio group, tert-butylthio group, n-pentylthio group, isopentylthio group, tert-pentylthio group, neopentylthio group, 2-pentylthio group, 3-pentylthio group, n-hexylthio group, 2-hexylthio group and the like.

The "alkylthio group optionally having substituent(s)" means an alkylthio group (as defined above) optionally substituted by one or more substituents, wherein the "substituent" is exemplified by carboxyl group, halogen atom, alkoxy group, hydroxyl group, amino group and the like. The detail of each substituent is as defined separately in the present specification.

The "arylthio group" means a thio group substituted by an aryl group (as defined above). Specific examples thereof include phenylthio group, naphthylthio group, anthrylthio group, phenanthrylthio group, biphenylthio group and the like.

The "arylthio group optionally having substituent(s)" means an arylthio group (as defined above) optionally substituted by one or more substituents, wherein the "substituent" is exemplified by carboxyl group, alkyl group, halogen atom, alkoxy group, hydroxyl group, amino group and the like. The detail of each substituent is as defined separately in the present specification.

The "heteroarylthio group" means a thio group substituted by heteroaryl group (as defined above). Specific examples thereof include pyridylthio group, pyrrolylthio group, furylthio group, thienylthio group, pyrazolylthio group, imidazolylthio group, indolylthio group, quinolylthio group, oxadiazolylthio group, thiadiazolylthio group, triazolylthio group, oxazolylthio group, thiazolylthio group, triazinylthio group, pyrazinylthio group, pyridazinylthio group, pyrimidinylthio group and the like.

The "heteroarylthio group optionally having substituent(s)" means a heteroarylthio group (as defined above) optionally substituted by one or more substituents, wherein the "substituent" is exemplified by carboxyl group, alkyl group, halogen atom, alkoxy group, hydroxyl group, amino group and the like. The detail of each substituent is as defined separately in the present specification.

The "aralkylthio group" means a thio group substituted by aralkyl group (as defined above). Specific examples thereof include benzylthio group, tritylthio group, phenethylthio group, 3-phenylpropylthio group, 2-phenylpropylthio group, 4-phenylbutylthio group, biphenylmethylthio group and the like.

The "aralkylthio group optionally having substituent(s)" means an aralkylthio group (as defined above) optionally substituted by one or more substituents, wherein the "substituent" is exemplified by carboxyl group, alkyl group, halogen atom, alkoxy group, hydroxyl group, amino group and the like. The detail of each substituent is as defined separately in the present specification.

The "alkylsulfonyl group" means a sulfonyl group substituted by straight chain or branched alkyl group having 1 to 6 carbon-atoms. Specific examples thereof include methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, tert-pentylsulfonyl group, neopentylsulfonyl group, 2-pentylsulfonyl group, 3-pentylsulfonyl group, n-hexylsulfonyl group, 2-hexylsulfonyl group and the like.

The "alkylsulfonyl group optionally having substituent(s)" means an alkylsulfonyl group (as defined above) optionally substituted by one or more substituents, wherein the "substituent" is exemplified by carboxyl group, halogen atom, alkoxy group, hydroxyl group, amino group and the like. The detail of each substituent is as defined separately in the present specification.

The "aralkylsulfonyl group" means a sulfonyl group substituted by aralkyl group (as defined above). Specific examples thereof include benzylsulfonyl group, tritylsulfonyl group, phenethylsulfonyl group, 3-phenylpropylsulfonyl group, 2-phenylpropylsulfonyl group, 4-phenylbutylsulfonyl group, biphenylmethylsulfonyl group and the like.

The "aralkylsulfonyl group optionally having substituent(s)" means an aralkylsulfonyl group (as defined above) optionally substituted by one or more substituents, wherein the "substituent" is exemplified by carboxyl group, halogen atom, alkoxy group, hydroxyl group, amino group and the like. The detail of each substituent is as defined separately in the present specification.

The "arylsulfonyl group" means a sulfonyl group substituted by aryl group (as defined above). Specific examples thereof include phenylsulfonyl group, naphthylsulfonyl group, anthrylsulfonyl group, phenanthrylsulfonyl group, biphenylsulfonyl group and the like.

The "arylsulfonyl group optionally having substituent(s)" means an arylsulfonyl group (as defined above) optionally substituted by one or more substituents, wherein the "substituent" is exemplified by carboxyl group, alkyl group, halogen atom, alkoxy group, hydroxyl group, amino group and the like. The detail of each substituent is as defined separately in the present specification.

The "heteroarylsulfonyl group" means a sulfonyl group substituted by heteroaryl group (as defined above). Specific examples thereof include pyridylsulfonyl group, pyrrolylsulfonyl group, furylsulfonyl group, thienylsulfonyl group, pyrazolylsulfonyl group, imidazolylsulfonyl group, indolylsulfonyl group, quinolylsulfonyl group, oxadiazolylsulfonyl group, thiadiazolylsulfonyl group, triazolylsulfonyl group, oxazolylsulfonyl group, thiazolylsulfonyl group, triazinylsulfonyl group, pyrazinylsulfonyl group, pyridazinylsulfonyl group, pyrimidinylsulfonyl group and the like.

The "heteroarylsulfonyl group optionally having substituent(s)" means a heteroarylsulfonyl group (as defined above) optionally substituted by one or more substituents, wherein the "substituent" is exemplified by carboxyl group, alkyl group, halogen atom, alkoxy group, hydroxyl group, amino group and the like. The detail of each substituent is as defined separately in the present specification.

The "alkoxycarbonylthio group" means a thio group substituted by alkoxycarbonyl group (as defined above). Specific examples thereof include methoxycarbonylthio group, ethoxycarbonylthio group, propoxycarbonylthio group, isopropoxycarbonylthio group, butoxycarbonylthio group, isobutoxycarbonylthio group, sec-butoxycarbonylthio group, tert-butoxycarbonylthio group and the like.

The "alkylaminocarbonyl group" means an aminocarbonyl group substituted by alkyl group (as defined above). Specific examples thereof include methylaminocarbonyl group, ethylaminocarbonyl group, propylaminocarbonyl group, butylaminocarbonyl group, pentylaminocarbonyl group, hexylaminocarbonyl group, heptylaminocarbonyl group, octylaminocarbonyl group, nonylaminocarbonyl group, decylaminocarbonyl group and the like.

The "aralkylaminocarbonyl group" means an aminocarbonyl group substituted by aralkyl group (as defined above). Specific examples thereof include benzylaminocarbonyl group, tritylaminocarbonyl group, phenethylaminocarbonyl group, 3-phenylpropylaminocarbonyl group, 2-phenylpropylaminocarbonyl group, 4-phenylbutylaminocarbonyl group, biphenylmethylaminocarbonyl group and the like.

The "haloaralkylaminocarbonyl group" means an aralkylaminocarbonyl group substituted by halogen atom (as defined above). Specific examples thereof include chlorobenzylaminocarbonyl group, fluorobenzylaminocarbonyl group, bromobenzylaminocarbonyl group and the like.

Preferable examples of $R_1$ include alkyl group optionally having substituent(s) (particularly, carboxyl group, halogen atom, alkoxycarbonyl group, aminocarbonyl group, aralkylaminocarbonyl group, alkoxy group), cycloalkyl group optionally having substituent(s) (particularly alkyl group), cycloalkylalkyl group, aralkyl group optionally having substituent(s) (particularly halogen atom, carboxyl group, alkyl group, hydroxyl group, nitro group, alkoxy group), aryl group optionally having substituent(s) (particularly halogen atom, alkyl group, alkoxy group, haloalkoxy group, nitro group, carboxyl group, hydroxyl group, alkylaminocarbonyl group, amino group optionally having substituent(s) (aralkyloxycarbonylamino, alkyloxycarbonylamino)), heteroaryl group, heteroarylalkyl group, and cycloalkyl group containing hetero atom(s) in its ring, which may have substituent (particularly alkyl group).

Preferable examples of $R_2$ and $R_3$ include hydrogen atom, hydroxyl group, alkyl group optionally having substituent(s) (particularly alkoxycarbonyl group) or aralkyl group optionally having substituent(s) (particularly hydroxyl group, sulfo group), and when $R_2$ and $R_3$, in combination, form a cycloalkyl group,

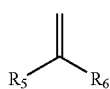

wherein $R_5$ and $R_6$ are as defined above, preferably $R_5$ and $R_6$ are the same or different and each is hydrogen atom (more preferably one of $R_5$ and $R_6$ is not hydrogen atom), an alkoxycarbonyl group, alkyl group optionally having substituent(s) (particularly alkylthio group), cycloalkyl group, aryl group optionally having substituent(s) (particularly halogen atom, alkoxy group, hydroxyl group, alkyl group, haloalkoxy group, alkoxycarbonyl group, carboxyl group, amino group optionally having substituent(s) (amino, alkyl-substituted amino, alkoxy-substituted amino)) or heteroaryl group optionally having substituent(s) (particularly alkyl group, hydroxyl group), or $R_5$ and $R_6$ are linked to form a cycloalkyl group or a cycloalkyl group containing hetero atom(s) in its ring],

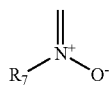

wherein $R_7$ is as defined above, preferably aryl group optionally having substituent(s) (particularly, amino optionally having substituent(s), such as alkylamino),

wherein $R_8$ is as defined above, preferably hydroxyl group, alkoxy group or aryl group optionally having substituent(s) (particularly alkyl group),

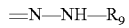

wherein $R_9$ is as defined above, preferably aryl group optionally having substituent(s) (particularly alkyl group), acyl group or carbamoyl group, and

can be mentioned.

Preferable examples of $R_4$ include hydrogen atom, alkyl group and aralkyl group.

Preferable examples of X include hydrogen atom, halogen atom, hydroxyl group, aryl group optionally having substituent(s) (particularly alkoxy group), heteroaryl group optionally having substituent(s) (particularly hydroxyl group), amino group optionally having substituent(s) (particularly alkyl group optionally having substituent(s) (particularly hydroxyalkyl), cycloalkylalkyl group, acyl group, aralkyl group optionally having substituent(s) (haloaralkyl, cyanoaralkyl, alkyloxycarbonylaralkyl, hydroxyaralkyl, carboxyaralkyl), hydroxyl group, cycloalkyl group), alkylthio group optionally having substituent(s) (particularly carboxyl group), aralkylthio group, arylthio group optionally having substituent(s) (particularly alkyl group), alkylsulfonyl group, arylsulfonyl group optionally having substituent(s) (particularly alkyl group), —N═CH—O-Alk wherein Alk is alkyl group) and alkoxycarbonylthio group.

The "pharmaceutically acceptable salt" may be any as long as it is a non-toxic salt formed together with the compound represented by the aforementioned formula (I). Examples thereof include addition salt with inorganic acid such as hydrofluoride, hydrochloride, hydrobromide, hydroiodide, sulfate, nitrate, phosphate, carbonate, hydrogencarbonate, perchlorate and the like; addition salt with organic acid such as formate, acetate, trifluoroacetate, propionate, oxalate, glycolate, succinate, lactate, maleate, hydroxymaleate, methylmaleate, fumarate, adipate, tartrate, malate, citrate benzoate, cinnamate, ascorbate, salicylate, 2-acetoxybenzoate, nicotinate, isonicotinate and the like; addition salt with organic sulfonic acid such as methanesulfonate, ethanesulfonate, isethionate, benzenesulfonate, p-toluenesulfonate, naphthalenesulfonate, hydroxybenzenesulfonate, dihydroxybenzenesulfonate and the like; addition salt with acidic amino acid such as aspartate, glutamate and the like; alkali metal salt such as sodium salt, potassium salt and the like; alkaline earth metal salt such as magnesium salt, calcium salt and the like; ammonium salt; addition salt with organic base such as trimethylamine salt, triethylamine salt, pyridine salt, picoline salt, dicyclohexylamine salt, N,N'-dibenzylethylenediamine salt and the like; addition salt with basic amino acid such as lysine salt, arginine salt and the like and the like. Besides the crystal form, the salt may be a solvate (including hydrate) with water, alcohol and the like in some cases.

The compound represented by the formula (I) may be present as various isomers. That is, a compound represented by the formula (I) may have one or plural asymmetric centers, and encompasses pure optical isomers, partially purified optical isomers, racemic mixtures and pure diastereomers, partially purified diastereomers, mixtures thereof and the like. In addition, a compound represented by the formula (I) may have structural isomers such as tautomer and the like, and such structural isomers are within the scope of the present invention.

The compound represented by the formula (I) of the present invention has a superior TNF-α production inhibitory action on mammals including human, bovine, horse, dog, mouse, rat and the like, and therefore, is expected to be a therapeutic agent of various diseases where inhibition of TNF-α production is effective, such as septic shock, sepsis, endotoxic shock, hemodynamic shock, post ischemic reperfusion injury, meningitis, psoriasis, congestive heart failure (congestive cardiomyopathy), fibrosis, hepatitis, non-insulin dependent diabetes mellitus (NIDDM), graft rejection, graft versus host disease, cancer, cachexia, autoimmune disease (systemic lupus erythematosus, rheumatic disease, allergy, multiple sclerosis, autoimmune uveitis, nephrotic syndrome, type I diabetes (IDDM) etc.), arthritis (chronic articular rheumatism, rheumatoid spondylitis, osteoarthritis, other arthritis), inflammatory bone disease, bone resorption disorder, Behcet's syndrome, infectious disease (opportunistic infectious disease in AIDS, cerebral malaria, mycobacteria infectious disease and the like), Crohn's disease, ulcerative colitis, ENL in leprosy, radiation damage, and damage of alveolus due to hyperoxia and the like, particularly, Crohn's disease, ulcerative colitis, sepsis, chronic articular rheumatism, autoimmune disease and the like. Even when a reference is simply made to a therapeutic agent in the present invention, such treatment includes any management such as prophylaxis, alleviation of symptoms, diminution of symptoms, arresting of disease and the like.

The compound represented by the formula (I) of the present invention, an isomer thereof, a solvate thereof or a pharmaceutically acceptable salt thereof is generally admixed with a pharmacologically acceptable carrier, an excipient, a diluent, an extender, a disintegrant, a stabilizer, a preservative, a buffer, an emulsifier, a flavoring agent, a coloring agent, a sweetening agent, a thickener, a corrigent, a solubilizer, other additives and the like, which are known per se, to give tablet, pill, powder, granule, suppository, injection, eye drop, liquid, capsule, troche, aerosol, elixir, suspension, emulsion, syrup and the like, which can be administered orally or parenterally.

When a solid preparation is to be prepared, additives such as sucrose, lactose, cellulose sugar, D-mannitol, multitol, dextran, starches, agar, alginates, chitins, chitosans, pectins, tragacanth gums, gum arabics, gelatins, collagens, casein, albumin, calcium phosphate, sorbitol, glycine, carboxymethyl cellulose, polyvinylpyrrolidone, hydroxypropyl cellulose, hydroxypropylmethyl cellulose, glycerine, polyethylene glycol, sodium hydrogencarbonate, magnesium stearate, talc and the like are used. Moreover, tablets can be made into typical tablets having a coating as necessary, such as sugar-coated tablets, enteric coated tablets, film-coated tablets or bilayer tablets and multilayer tablets.

When a semisolid preparation is to be prepared, animal or vegetable oil and fat (olive oil, corn oil, castor oil and the like), mineral oil and fat (petrolatum, white petrolatum, solid paraffin and the like), waxes (jojoba oil, Carnauba wax, beeswax and the like), partially synthesized or totally synthesized glycerine fatty acid ester (lauric acid, myristic acid, palmitic acid and the like) and the like are used.

When a liquid preparation is to be prepared, additives, such as sodium chloride, glucose, sorbitol, glycerine, olive oil, propylene glycol, ethyl alcohol and the like are mentioned. Particularly, when an injection is to be prepared, sterile aqueous solution, such as physiological saline, isotonic solution, oily solution, such as sesame oil and soya bean oil are used. Where necessary, suitable suspending agents, such as carboxymethyl cellulose sodium, nonionic surfactant, dissolution aids, such as benzyl benzoate, benzyl alcohol and the like, may be used concurrently. Furthermore, when an eye drop is to be prepared, aqueous liquid or aqueous solution is used, and particularly, sterile aqueous solution for injection can be mentioned. This eye liquid may contain various additives such as buffer, isotonicity agent, dissolution aids, preservative, thickener, chelating agent, pH adjuster and flavoring agent.

In addition, the compound of the present invention can be used as a pharmaceutical agent for animals, not to mention a pharmaceutical agent for human.

The dose is appropriately set depending on the kind and severity of disease, compound to be administered and administration route, age, sex, body weight and the like of patients (administration subject).

The compound represented by the formula (I) of the present invention can be produced according to but not limited to, for example, the following Synthetic Methods or a combination thereof, which may be modified as appropriate when desired. Such modification includes alkylation, acylation, amination, imination, halogenation, reduction, oxidization and the like, for which the reaction or method generally used in this field can be utilized.

Furthermore, the solvent to be used for each reaction is not particularly limited as long as it does not exert an disadvantageous influence on the reaction, and those generally used in this field can be used. Moreover, the reaction time and reaction temperature in each reaction are also determined as appropriate for the reaction.

Synthetic Method 1: when, in the formula (I), X is an unsubstituted amino group, Y is an oxygen atom, and $R_2$, $R_3$ and $R_4$ are each a hydrogen atom The compound can be synthesized according to the method described in J. Am. Chem. Soc., 81, pp. 2456-2464 (1959). For example, a compound of the formula (II) can be synthesized as in the following.

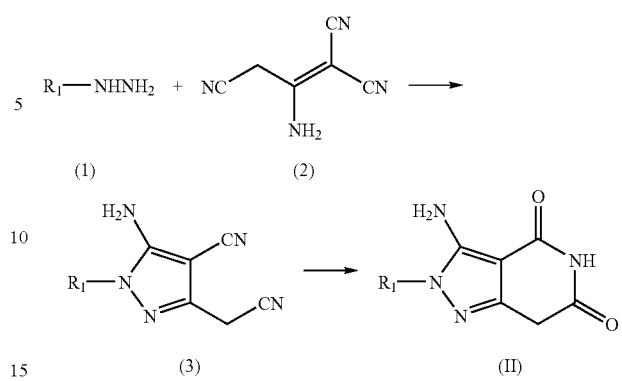

wherein $R_1$ is as defined above.

The object compound (II) is obtained by reacting the corresponding hydrazine compound (1) with 2-amino-1,1,3-tricyano-1-propene (2) and then cyclization in conc. hydrochloric acid.

When $R_1$ is a phenyl group, this compound is a known compound represented by the formula

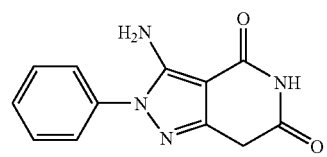

This compound can be synthesized according to the method described in J. Am. Chem. Soc., 81, pp. 2456-2464 (1959).

Synthetic Method 2: when, in the formula (I), X is a substituted amino group, Y is an oxygen atom, and $R_2$, $R_3$ and $R_4$ are each a hydrogen atom

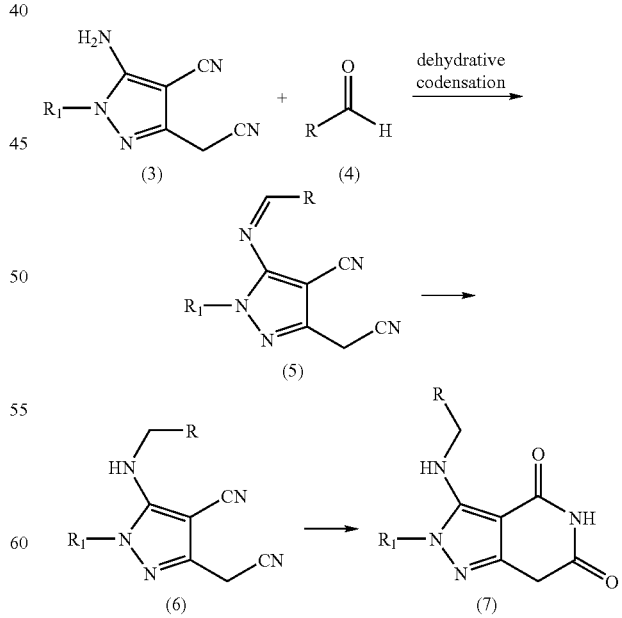

wherein $R_1$ is as defined above and R is an optionally substituted alkyl group, optionally substituted aryl group, optionally substituted heteroaryl group and the like.

The object compound (7) is obtained by subjecting the compound (3) to dehydrative condensation with the corresponding aldehyde (4) to give imine compound (5), reducing the compound to give an amine compound (6), then cyclizing the compound in conc. hydrochloric acid.

Synthetic Method 3: when, in the formula (I), X is a hydrogen atom or a halogen atom, Y is an oxygen atom, and $R_2$, $R_3$ and $R_4$ are each a hydrogen atom

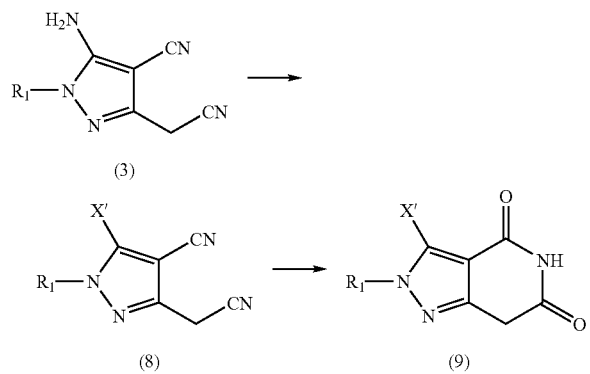

wherein $R_1$ is as defined above and X' is a hydrogen atom or a halogen atom.

Particularly, when, in the formula (I), X is a halogen atom, compound (3) is converted to a diazonium salt, halogenated to give compound (8: X'=halogen atom) and the compound is cyclized in conc. hydrochloric acid to give the object compound (9: X'=halogen atom). When X is a hydrogen atom, compound (3) is converted to a diazonium salt, the salt is reduced to give compound (8:X'=hydrogen atom), and the compound is cyclized in conc. hydrochloric acid to give the object compound (9:X'=hydrogen atom).

Synthetic Method 4: when, in the formula (I), X is an alkylthio group optionally having substituent(s), an aralkylthio group optionally having substituent(s), an arylthio group optionally having substituent(s), a heteroarylthio group optionally having substituent(s), an alkylsulfonyl group optionally having substituent(s), an aralkylsulfonyl group optionally having substituent(s), an arylsulfonyl group optionally having substituent(s) or a heteroarylsulfonyl group optionally having substituent(s), Y is an oxygen atom and $R_2$, $R_3$ and $R_4$ are each a hydrogen atom

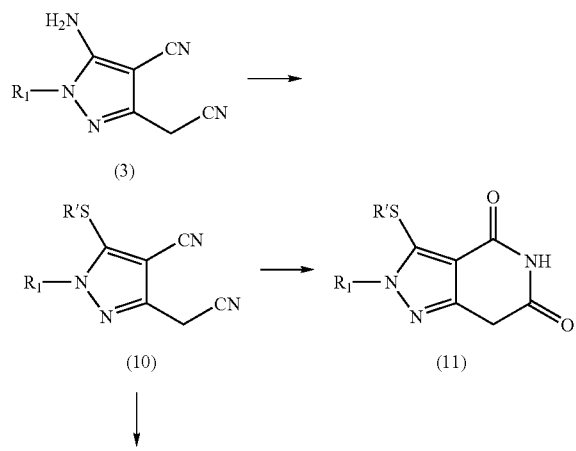

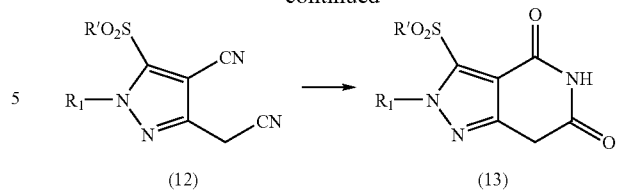

wherein $R_1$ is as defined above and R' is an alkyl group optionally having substituent(s), an aralkyl group optionally having substituent(s), an aryl group optionally having substituent(s) or a heteroaryl group optionally having substituent(s).

The object compound (11) is obtained by reacting the compound (3) with the corresponding disulfide to give compound (10), and further cyclizing the compound in conc. hydrochloric acid. When this compound (10) is oxidized to give compound (12) and further cyclized in conc. hydrochloric acid in the same manner, the object compound (13) is obtained.

Synthetic Method 5: when, in the formula (I), X is an unsubstituted amino group, Y is an oxygen atom, $R_4$ is a hydrogen atom, and $R_2$ and $R_3$ are linked to show $=CR_5R_6$

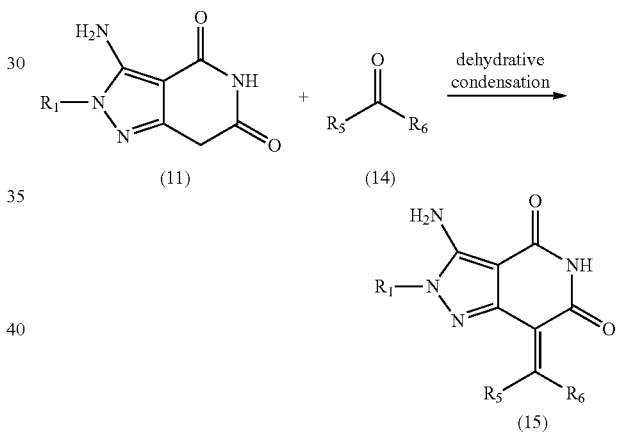

wherein $R_1$, $R_5$ and $R_6$ are each as defined above.

The compound (II) synthesized according to Synthetic Method 1 is subjected to dehydrative condensation with carbonyl compound (14) in the presence of an acid or a base to give the object compound (15).

Synthetic Method 6: when, in the formula (I), X is an unsubstituted amino group, Y is an oxygen atom, $R_4$ is a hydrogen atom, and $R_2$ and $R_3$ are linked to show a cycloalkyl group Particularly, the case where the cycloalkyl group formed by $R_2$ and $R_3$ in combination is cyclopropyl group is explained as an example.

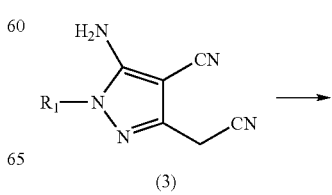

-continued

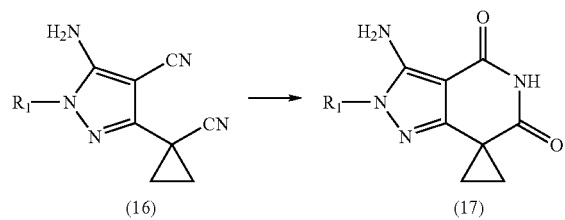

wherein $R_1$ is as defined above.

The compound (3) is reacted with 1,2-dibromoethane under basic conditions to give a cyclopropane compound (16). This is cyclized in conc. hydrochloric acid to give object compound (17).

Synthetic Method 7: when, in the formula (I), X is an unsubstituted amino group, Y is an oxygen atom, $R_4$ is a hydrogen atom, and $R_2$ and $R_3$ are linked to show $=N(O)R_7$

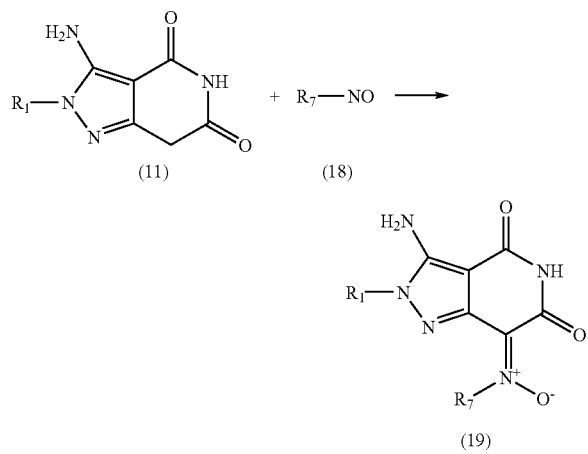

wherein $R_1$, $R_7$ are each as defined above.

The compound (II) synthesized according to Synthetic Method 1 is reacted with nitroso compound (18) to give the object compound (19).

Synthetic Method 8: when, in the formula (I), X is an unsubstituted amino group, Y is an oxygen atom, $R_4$ is a hydrogen atom, one of $R_2$ and $R_3$ is a hydrogen atom and the other is a hydroxyl group, or when $R_2$ and $R_3$ are linked to show $=O$, $=N-R_8$ or $=N-NHR_9$

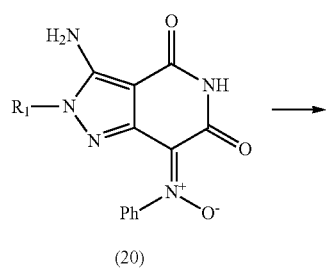

-continued

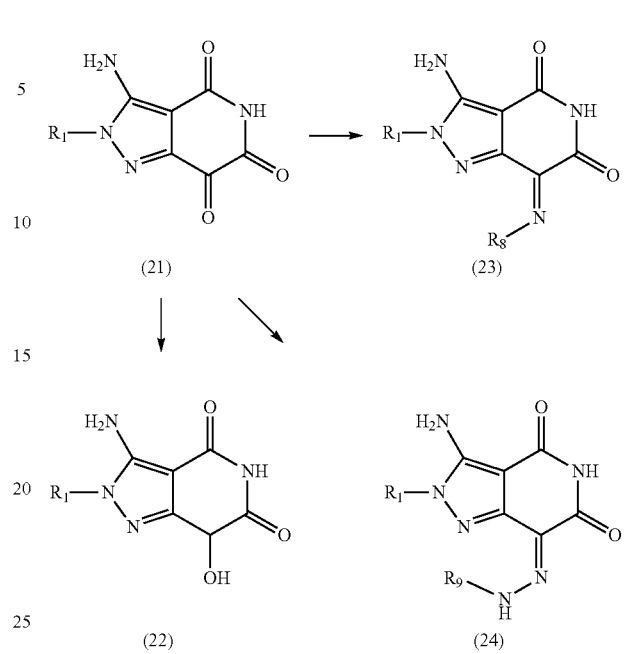

wherein $R_1$, $R_8$ and $R_9$ are as defined above, and Ph is a phenyl group.

The compound (21) is obtained from compound (20) synthesized according to Synthetic Method 7 and this compound is reduced to give the object compound (22). The compound (21) is reacted with an amine compound or a hydrazine compound to give the object compound (23) or (24).

Synthetic Method 9: when, in the formula (I), X is a hydroxyl group, $R_2$ and $R_3$ are hydrogen atoms, and $R_4$ is an alkyl group optionally having substituent(s) or an aralkyl group optionally having substituent(s)

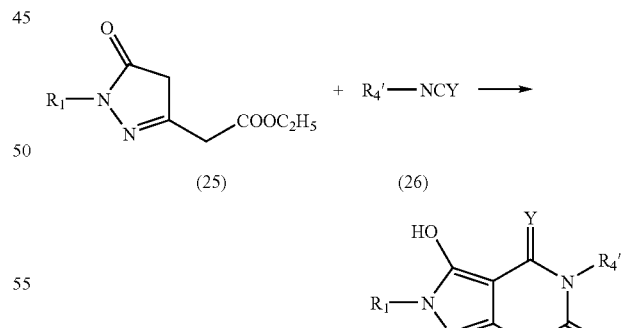

wherein $R_1$ and Y are as defined above and $R_4'$ is an alkyl group optionally having substituent(s) or an aralkyl group optionally having substituent(s).

The compound (25) is reacted with an isocyanate compound (26, Y=oxygen atom) or an isothiocyanate compound (26, Y=sulfur atom) to give the object compound (27).

Synthetic Method 10: when, in the formula (I), X is a substituted amino group, and $R_2$, $R_3$ and $R_4$ are hydrogen atoms wherein Ra and Rb are the same or different and each is an alkyl group, an aralkyl group optionally having substituent(s) an acyl group optionally having substituent(s), a cycloalkyl group optionally having substituent(s), a cycloalkylalkyl group optionally having substituent(s), an alkoxycarbonyl group optionally having substituent(s), an aralkyloxycarbonyl group optionally having substituent(s) and the like, X" is a halogen atom, and $R_1$ is as defined above.

The compound (8': corresponds to the aforementioned compound (8) wherein X' is a halogen atom) is reacted with various amines in the presence of a base to give compound (28) and the compound is cyclized in conc. hydrochloric acid to give the object compound (29).

Synthetic Method 11: when, in the formula (I), X is an aryl group optionally having substituent(s) or a heteroaryl group optionally having substituent(s), and $R_2$, $R_3$ and $R_4$ are hydrogen atoms wherein Ar is an aryl group optionally having substituent(s) or a heteroaryl group optionally having substituent(s), X" is a halogen atom and $R_1$ is as defined above.

The compound (8': corresponds to the aforementioned compound (8) wherein X' is a halogen atom) is reacted with aryl boronic acid or heteroaryl boronic acid by Suzuki coupling reaction to give compound (30), and the compound is cyclized in conc. hydrochloric acid to give the object compound (31).

The present invention is explained in detail by referring to Examples, which are not to be construed as limitative. The structure of the compounds produced in respective Examples are shown later in Table 1-Table 18.

Example 1

Step 1

2,4,6-Trichlorophenylhydrazine (4.67 g, 22.1 mmol) and 2-amino-1,1,3-tricyano-1-propene (2.65 g, 20.1 mmol) were heated under reflux in ethanol (60 ml) for 4 days. The reaction mixture was diluted with ethyl acetate and 1M hydrochloric acid solution and the ethyl acetate layer was separated. The layer was washed, dried and concentrated according to a conventional method, and purified by silica gel column chromatography (ethyl acetate-hexane mixture) to give the object nitrile intermediate (intermediate 3 of Synthetic Method 1 wherein $R_1$ is 2,4,6-trichlorophenyl group) (1.11 g, 17%).

Step 2

The nitrile intermediate (1.11 g, 3.41 mmol) obtained in Step 1 was reacted in conc. hydrochloric acid (20 ml) at 70° C. for 2 hrs, and the solvent was evaporated. The residue was purified by silica gel chromatography (dichloromethane-methanol mixture) to give a compound (0.917 g, 78%) of Example 1.
MS (ESI) m/z 343 (M−H)−

Example 2

In the same manner as in Example 1, a compound of Example 2 was synthesized using methylhydrazine and 2-amino-1,1,3-tricyano-1-propene as starting materials.
MS (ESI) m/z 179 (M−H)−

Example 3

Step 1

A solution (2.5 ml) of cyclohexylhydrazine hydrochloride (166 mg, 1.10 mmol), 2-amino-1,1,3-tricyano-1-propene (136 mg, 1.03 mmol) and triethylamine (0.3 ml) in ethanol was stirred with heating at 70° C. for 8 hrs, and the solvent was evaporated. After evaporation, the residue was partitioned between ethyl acetate and saturated brine, which was followed by washing, drying and concentration according to a conventional method and then purification by silica gel column chromatography (ethyl acetate-hexane mixture) to give a nitrile intermediate (intermediate 3 of Synthetic Method 1 wherein $R_1$ is cyclohexyl group) (172 mg, 68%).

Step 2

In the same manner as in Step 2 of Example 1, a compound of Example 3 was synthesized using the nitrile intermediate obtained in Step 1.
MS (ESI) m/z 247 (M−H)−

Example 4

In the same manner as in Example 3, a compound of Example 4 was synthesized using benzylhydrazine hydrochloride and 2-amino-1,1,13-tricyano-1-propene as starting materials.
MS (ESI) m/z 255 (M−H)−

Example 5

In the same manner as in Example 3, a compound of Example 0.5 was synthesized using p-tolylhydrazine hydrochloride and 2-amino-1,1,13-tricyano-1-propene as starting materials.
MS (ESI) m/z 255 (M−H)−

Example 6

In the same manner as in Example 3, a compound of Example 6 was synthesized using 4-isopropylphenylhydrazine hydrochloride and 2-amino-1,1,3-tricyano-1-propene as starting materials.

MS (ESI) m/z 285 (M+H)+

Example 7

In the same manner as in Example 3, a compound of Example 7 was synthesized using 4-methoxyphenylhydrazine hydrochloride and 2-amino-1,1,3-tricyano-1-propene as starting materials.

1H-NMR (300 MHz, DMSO-d6) δ 3.75 (2H, s), 3.81 (3H, s), 6.31 (2H, s), 7.07 (2H, d, J=9 Hz), 7.42 (2H, d, J=9 Hz), 10.58 (1H, s).

Example 8

In the same manner as in Example 3, a compound of Example 8 was synthesized using 4-(trifluoromethoxy)phenylhydrazine hydrochloride and 2-amino-1,1,3-tricyano-1-propene as starting materials.

MS (ESI) m/z 325 (M–H)–

Example 9

In the same manner as in Example 3, a compound of Example 9 was synthesized using 3-fluorobenzenehydrazine hydrochloride and 2-amino-1,1,3-tricyano-1-propene as starting materials.

MS (ESI) m/z 259 (M–H)–

Example 10

In the same manner as in Example 3, a compound of Example 10 was synthesized using 4-nitrophenylhydrazine hydrochloride and 2-amino-1,1,3-tricyano-1-propene as starting materials.

MS (FAB, glycerol) m/z 288 (M+H)+

Example 11

In the same manner as in Example 3, a compound of Example 11 was synthesized using 3-chlorophenylhydrazine hydrochloride and 2-amino-1,1,3-tricyano-1-propene as starting materials.

MS (FAB, NBA) m/z 277 (M+H)+

Example 12

In the same manner as in Example 3, a compound of Example 12 was synthesized using 4-chlorophenylhydrazine hydrochloride and 2-amino-1,1,3-tricyano-1-propene as starting materials.

MS (FAB) m/z 277 (M+H)+

Example 13

In the same manner as in Example 1, a compound of Example 13 was synthesized using 2-hydrazinopyridine and 2-amino-1,1,3-tricyano-1-propene as starting materials.

MS (FAB, NBA) m/z 244 (M+H)+

Example 14

In the same manner as in Example 3, a compound of Example 14 was synthesized using m-tolylhydrazine hydrochloride and 2-amino-1,1,3-tricyano-1-propene as starting materials.

1H-NMR (300 MHz, DMSO-d6) δ 2.38 (3H, s), 3.76 (2H, s), 6.44 (2H, s), 7.22 (1H, d, J=7 Hz), 7.33 (2H, m), 7.39 (1H, t, J=8 Hz), 10.59 (1H, s).

Example 15

In the same manner as in Example 3, a compound of Example 15 was synthesized using o-tolylhydrazine hydrochloride and 2-amino-1,1,13-tricyano-1-propene as starting materials.

MS (ESI) m/z 255 (M–H)–

Example 16

In the same manner as in Example 3, a compound of Example 16 was synthesized using 3-methoxyphenylhydrazine hydrochloride and 2-amino-1,1,3-tricyano-1-propene as starting materials.

1H-NMR (300 MHz, DMSO-d6) δ 3.76 (2H, s), 3.81 (3H, s), 6.48 (2H, s), 6.97 (1H, dd, J=8, 3 Hz), 7.07 (1H, t, J=3 Hz), 7.10 (1H, d, J=8 Hz), 7.43 (1H, t, J=8 Hz), 10.60 (1H, s).

Example 17

In the same manner as in Example 3, a compound of Example 17 was synthesized using 2-methoxyphenylhydrazine hydrochloride and 2-amino-1,1,3-tricyano-1-propene as starting materials.

MS (ESI) m/z 273 (M+H)+

Example 18

In the same manner as in Example 3, a compound of Example 18 was synthesized using 2-chlorophenylhydrazine hydrochloride and 2-amino-1,1,3-tricyano-1-propene as starting materials.

1H-NMR (300 MHz, DMSO-d6) δ 3.75 (2H, s), 6.47 (2H, s), 7.53 (3H, m), 7.68 (1H, d, J=7 Hz), 10.54 (1H, s).

Example 19

In the same manner as in Example 3, a compound of Example 19 was synthesized using 2,6-dichlorophenylhydrazine hydrochloride and 2-amino-1,1,3-tricyano-1-propene as starting materials.

1H-NMR (300 MHz, DMSO-d6) δ 3.76 (2H, s), 6.70 (2H, s), 7.57 (1H, dd, J=9, 7 Hz), 7.67 (d, 1H, J=7 Hz), 7.67 (d, 1H, J=9 Hz), 10.54 (1H, s).

Example 20

In the same manner as in Example 3, a compound of Example 20 was synthesized using 3,4-dichlorophenylhydrazine hydrochloride and 2-amino-1,1,3-tricyano-1-propene as starting materials.

1H-NMR (300 MHz, DMSO-d6) δ 3.76 (2H, s), 6.72 (2H, s), 7.55 (1H, dd, J=8, 2 Hz), 7.78 (1H, d, J=8 Hz), 7.88 (1H, d, J=2 Hz), 10.54 (1H, s).

Example 21

5-Amino-4-cyano-3-cyanomethyl-1-phenylpyrazole (4.0 g, 17.9 mmol) was dissolved in conc. hydrochloric acid (50 ml), and the mixture was stirred overnight at 70° C. with heating. The reaction mixture was allowed to cool to room temperature and water was added. The precipitated crystals were collected by filtration and dried to give a compound of Example 21 (3.85 g, 15.9 mmol, 89%) as yellow-white crystals.

Example 22 and Example 23

The compound (133 mg, 0.55 mmol) obtained in Example 21 and sodium hydride (49.5 mg, 1.24 mmol, 60% oil susp.) were suspended in THF (2 ml) at 0° C. and methyl iodide (1 ml, 1.61 mmol) was added. After 4 hours, the reaction was quenched with 1N aqueous hydrochloric acid solution. The reaction mixture was extracted with ethyl acetate, and after washing, drying and concentration according to conventional methods, purified by silica gel column chromatography (ethyl acetate-hexane mixture) to give a compound of Example 22 (13.0 mg, 8%) and a compound of Example 23 (37.1 mg, 25%).

compound of Example 22:MS (ESI) m/z 285 (M+H)+, m/z 283 (M−H)− compound of Example 23:MS (ESI) m/z 269 (M−H)−

Example 24

Step 1

5-Amino-4-cyano-3-cyanomethyl-1-phenylpyrazole (114 mg, 0.51 mmol) was dissolved in conc. hydrochloric acid (0.4 ml) at 0° C. and an aqueous solution (2 ml) of sodium nitrite (46.5 mg, 0.67 mmol) was slowly added dropwise. A solution (0.8 ml) of urea (9.0 mg, 0.15 mmol) and copper chloride (I) (48.3 mg, 0.49 mmol) in carbon tetrachloride was added and the mixture was stirred at room temperature. After 4 hours, water was added and the mixture was extracted with dichloromethane. The extract was washed, dried and concentrated according to conventional methods, then purified by thin-layer silica gel column chromatography (ethyl acetate-hexane mixture) to give a chlorine substituted compound (intermediate 8 of Synthetic Method 3 wherein X' is chlorine atom and $R_1$ is phenyl group) (41.1 mg, 33%).

Step 2

The chlorine-substituted compound (41.1 mg, 1.69 mmol) obtained in Step 1 was dissolved in conc. hydrochloric acid (0.4 ml) and 1,4-dioxane (0.4 ml), and the mixture was heated to 70° C. After 2 hrs, the solvent was evaporated and the residue was purified by silica gel chromatography (ethyl acetate-hexane mixture) to give a compound of Example 24 (41.4 mg, 93%)

1H-NMR (300 MHz, DMSO-d6) δ 3.98 (2H, s), 7.62 (5H, m), 11.13 (1H, s).

Example 25

Step 1

5-Amino-4-cyano-3-cyanomethyl-1-phenylpyrazole (114 mg, 0.51 mmol) and 50% aqueous hypophosphorous acid solution (0.1 ml) were dissolved in a mixed solution of water (1 ml) and 1,4-dioxane (0.2 ml) and the mixture was cooled to 0° C. An aqueous solution (1 ml) of sodium nitrite (78.4 mg, 1.14 mmol) was slowly added dropwise to the reaction mixture and the mixture was stirred at room temperature. After 17 hrs, the reaction mixture was extracted with ethyl acetate, and the ethyl acetate layer was washed with 1M aqueous sodium hydroxide solution, dried, concentrated and purified by silica gel column chromatography (ethyl acetate-hexane mixture) to give a hydrogen-substituted compound (intermediate 8 of Synthetic Method 3 wherein X' is a hydrogen atom and $R_1$ is phenyl group) (37.7 mg, 35%).

Step 2

In the same manner as in Step 2 of Example 24, a compound of Example 25 was synthesized using the hydrogen-substituted compound obtained in Step 1.

1H-NMR (300 MHz, DMSO-d6) δ 3.97 (2H, s), 7.38 (1H, t, J=7 Hz), 7.52 (1H, t, J=7 Hz), 7.91 (1H, d, J=7 Hz), 9.20 (1H, s), 11.02 (1H, s).

Example 26

Step 1

5-Amino-4-cyano-3-cyanomethyl-1-phenylpyrazole (113 mg, 0.51 mmol) was dissolved in 1,4-dioxane (0.2 ml) and the mixture was cooled to 0° C. Then 40% aqueous hydrobromic acid solution (0.3 ml, 2.21 mmol) was added. An aqueous solution (1 ml) of sodium nitrite (39.6 mg, 0.57 mmol) was slowly added dropwise to the mixed solution. Copper (3.3 mg) was further added and the mixture was stirred at room temperature for 17 hrs and extracted with ethyl acetate. The ethyl acetate layer was washed with saturated aqueous sodium hydrogen carbonate solution, dried, concentrated and purified by thin-layer silica gel column chromatography (dichloromethane) to give a bromine-substituted compound (intermediate 8 of Synthetic Method 3 wherein X' is bromine atom and $R_1$ is phenyl group) (27.6 mg, 19%).

Step 2

In the same manner as in Step 2 of Example 24, a compound of Example 26 was synthesized using the bromine-substituted compound obtained in Step 1.

MS (ESI) m/z 304 (M−H)−

Example 27

Step 1

5-Amino-4-cyano-3-cyanomethyl-1-phenylpyrazole (115 mg, 0.51 mmol) was dissolved in acetic acid (1.35 ml) and cooled to 0° C. Sodium nitrite (47.9 mg, 0.69 mmol) was gradually added to conc. sulfuric acid (0.3 ml) separately cooled with ice water, once heated to 70° C. for dissolution and then cooled. This sodium nitrite solution was slowly added to an acetic acid solution and an aqueous solution (0.8 ml) of urea (60 mg, 1.00 mmol) and potassium iodide (129 mg, 0.78 mmol) was added. The mixture was stirred for 3.5 hrs. Then sodium hyposulfite was added to the reaction solution to quench the reaction. The reaction mixture was extracted with ethyl acetate. The extract was washed with 1M aqueous sodium hydroxide solution and saturated brine, dried, concentrated and purified by thin-layer silica gel column chromatography to give an iodine-substituted compound (intermediate 8 of Synthetic Method 3 wherein X' is iodine atom and $R_1$ is phenyl group) as a mixture with a hydrogen-substituted compound (intermediate 8 wherein X' is a hydrogen atom and $R_1$ is phenyl group) (25.6 mg). (iodine compound:hydrogen compound=4:1)

Step 2

In the same manner as in Step 2 of Example 0.24, a compound of Example 27 was synthesized.
MS (ESI) m/z 354 (M+H)+, m/z 352 (M−H)−

Example 28

Step 1

5-amino-4-cyano-3-cyanomethyl-1-phenylpyrazole (225 mg, 1.01 mmol) and dimethyldisulfide (199 mg, 2.12 mmol) were dissolved in chloroform (5 ml) and cooled with ice water. Then, t-butyl nitrite (170 mg, 1.65 mmol) was slowly added dropwise. The mixture was allowed to return to room temperature and stirred for 2 hrs. The chloroform solution was washed, dried and concentrated according to conventional methods, and purified by silica gel column chromatography (ethyl acetate-hexane mixture) to give a methylsulfide compound (intermediate 10 of Synthetic Method 4 wherein $R_1$ is phenyl group and R' is methyl group) (72.5 mg, 28%).

Step 2

In the same manner as in Step 2 of Example 24, a compound of Example 28 was synthesized using the methylsulfide compound obtained in Step 1.
1H-NMR (300 MHz, DMSO-d6) δ 2.53 (3H, s), 3.95 (2H, s), 7.56 (5H, m), 11.12 (1H, s).

Example 29

Step 1

The methylsulfide compound (72.5 mg, 0.29 mmol) obtained in Step 1 of Example 28 was dissolved in 30% hydrogen peroxide solution (0.2 ml) and acetic acid (0.4 ml) and the mixture was stirred with heating at 70° C. After 4 hrs, cold water was added to allow precipitation of a solid, which was suction filtrated and dried. The obtained solid was purified by silica gel chromatography (ethyl acetate-hexane mixture) to give a methylsulfonyl compound (intermediate 12 of Synthetic Method 4 wherein $R_1$ is phenyl group and R' is methyl group)(36.6 mg, 45%).

Step 2

In the same manner as in Step 2 of Example 24, a compound of Example 29 was synthesized using the methylsulfonyl compound obtained in Step 1.
MS (ESI) m/z 304 (M−H)−

Example 30

In the same manner as in Example 3, a compound of Example 30 was synthesized using ethylhydrazine oxalate and 2-amino-1,1,3-tricyano-1-propene as starting materials.
MS (ESI) m/z 193 (M−H)−

Example 31

In the same manner as in Example 1, a compound of Example 31 was synthesized using 2-cyanoethylhydrazine and 2-amino-1,1,3-tricyano-1-propene as starting materials.
MS (ESI) m/z 237 (M−H)−

Example 32

In the same manner as in Example 28, a compound of Example 32 was synthesized using 5-amino-4-cyano-3-cyanomethyl-1-phenylpyrazole and diethyldisulfide as starting materials.
1H-NMR (300 MHz, DMSO-d6) δ 1.02 (3H, t, J=8 Hz), 3.08 (2H, q, J=8 Hz), 3.95 (2H, s), 7.55 (5H, m), 11.01 (1H, s).

Example 33

In the same manner as in Example 28, a compound of Example 33 was synthesized using 5-amino-4-cyano-3-cyanomethyl-1-phenylpyrazole and diphenyldisulfide as starting materials.
MS (ESI) m/z 334 (M−H)−

Example 34

In the same manner as in Example 28, a compound of Example 34 was synthesized using 5-amino-4-cyano-3-cyanomethyl-1-phenylpyrazole and dibenzyldisulfide as starting materials.
1H-NMR (300 MHz, DMSO-d6) δ 3.95 (2H, s), 4.33 (2H, s), 7.05 (3H, m), 7.22 (5H, m), 7.45 (2H, m), 11.10 (1H, s).

Example 35

In the same manner as in Example 28, a compound of Example 35 was synthesized using 5-amino-4-cyano-3-cyanomethyl-1-phenylpyrazole and p-tolyldisulfide as starting materials.
MS (ESI) m/z 348 (M−H)−

Example 36

To a solution (4 ml) of a compound of Example 31 (50.0 mg, 0.21 mmol) in methanol was added thionyl chloride (0.05 ml, 0.69 mmol) at 0° C. After 1 hr, the solvent was evaporated and water was added. The precipitate was removed by suction filtration. The filtrate was extracted with ethyl acetate, washed with saturated aqueous sodium hydrogencarbonate solution and saturated brine, dried, concentrated and purified by preparative thin-layer silica gel chromatography (ethyl acetate) to give a compound of Example 36 (1.3 mg, 2%).
MS (ESI) m/z 251 (M−H)−

Example 37

In the same manner as in Example 28, a compound of Example 37 was synthesized using 5-amino-4-cyano-3-cyanomethyl-1-phenylpyrazole and dimethyl 3,3'-dithiodipropionate as starting materials.
1H-NMR (300 MHz, DMSO-d6) δ 2.40 (2H, t, J=7 Hz), 3.24 (2H, t, J=7 Hz), 3.95 (2H, s), 7.52 (5H, m), 11.03 (1H, s).

Example 38

In the same manner as in Example 28, a compound of Example 38 was synthesized using 5-amino-4-cyano-3-cyanomethyl-1-phenylpyrazole and methoxycarbonylsulfenyl chloride as starting materials.

1H-NMR (300 MHz, DMSO-d6) δ 3.74 (3H, s), 4.05 (2H, s), 7.55 (5H, m), 11.13 (1H, s).

Example 39

A compound of Example 31 (46.7 mg, 0.20 mmol) was dissolved in 1,4-dioxane (2 ml), and pyridine (0.02 ml), Boc$_2$O (61.3 mg, 0.28 mmol) and ammonium hydrogencarbonate (22.8 mg, 0.29 mmol) were added. After 17 hrs, the precipitate was suction filtrated to give a compound of Example 39 (29.1 mg, 63%).

1H-NMR (300 MHz, DMSO-d6) δ 2.54 (2H, t, J=7 Hz), 3.65 (2H, s), 4.04 (2H, t, J=7 Hz), 6.33 (2H, s), 6.98 (1H, s), 7.45 (1H, s), 10.43 (1H, s).

Example 40 and Example 41

To a solution (1.5 ml) of a compound of Example 31 (46.5 mg, 0.20 mmol) in dimethylformamide were added benzylamine (0.1 ml, 0.92 mmol), WSC.HCl (58.9 mg, 0.31 ml), HOBt (0.6 ml, 0.30 mmol; 0.5 M DMF solution) and one drop of triethylamine, and the mixture was stirred for 13 hrs. After completion of the reaction, methylene chloride and 1N aqueous hydrochloric acid solution were added. The precipitate was suction filtrated and the solid was purified by silica gel chromatography (methylene chloride-methanol mixture) to give a compound of Example 40 (19.1 mg, 30%) and a compound of Example 41 (6.8 mg, 8%).

Compound of Example 40:
MS (ESI) m/z 327 (M+H)+, m/z 325 (M–H)–
Compound of Example 41:
MS (ESI) m/z 416 (M+H)+, m/z 414 (M–H)–

Example 42

In the same manner as in Example 29, compound of Example 42 (10%) was synthesized from a p-tolylsulfide compound (intermediate 10 of Synthetic Method 4 wherein R$_1$ is phenyl group and R' is p-tolyl)(1.95 g, 5.89 mmol), which is a synthetic intermediate of a compound of Example 35.
MS (ESI) m/z 380 (M–H)–

Example 43

A compound of Example 21 (121 mg, 0.5 mmol) and 4-methoxybenzaldehyde (68.0 mg, 0.5 mmol) were stirred overnight in ethanol (5 ml) in the presence of a catalytic amount of acetic acid with heating under reflux. The mixture was allowed to cool at room temperature. The precipitated crystals were collected by filtration, washed with ethyl acetate and dried to give a compound of Example 43 (119.3 mg, 0.32 mmol, 64%) as yellow crystals.
MS (ESI) m/z 359.0 (M–H)–

Example 44

In the same manner as in Example 43, a compound of Example 44 was synthesized using a compound of Example 21 and 4-chloro benzaldehyde as starting materials.
1H-NMR (300 MHz, DMSO-d6) δ 6.63 (2H, s), 7.49-7.65 (7H, m), 7.99 (1H, s), 8.43 (2H, d, J=8.7 Hz), 11.0 (1H, s).

Example 45

In the same manner as in Example 43, a compound of Example 45 was synthesized using a compound of Example 21 and 4-dimethylaminobenzaldehyde as starting materials.
MS (ESI) m/z 372.1 (M–H)–

Example 46

In the same manner as in Example 43, a compound of Example 46 was synthesized using a compound of Example 21 and 4-hydroxybenzaldehyde as starting materials.
MS (ESI) m/z 345.0 (M–H)–

Example 47

In the same manner as in Example 43, a compound of Example 47 was synthesized using a compound of Example 21 and 4-methylbenzaldehyde as starting materials.
MS (ESI) m/z 342.9 (M–H)–

Example 48

In the same manner as in Example 43, a compound of Example 48 was synthesized using a compound of Example 21 and 4-trifluoromethoxybenzaldehyde as starting materials.
MS (ESI) m/z 413.1 (M–H)–

Example 49

In the same-manner as in Example 43, a compound of Example 49 was synthesized using a compound of Example 21 and 2-methylbenzaldehyde as starting materials.
MS (ESI) m/z 342.9 (M–H)–

Example 50

In the same manner as in Example 43, a compound of Example 50 was synthesized using a compound of Example 21 and 3-methylbenzaldehyde as starting materials.
MS (ESI) m/z 343.1 (M–H)–

Example 51

In the same manner as in Example 43, a compound of Example 51 was synthesized using a compound of Example 21 and 3,4-dichlorobenzaldehyde as starting materials.
1H-NMR (300 MHz, DMSO-d6) δ 6.70 (2H, s), 7.43-7.48 (1H, m), 7.56-7.61 (2H, m), 7.66-7.98 (3H, m), 7.96 (1H, s), 8.08 (1H, d, J=8.7 Hz), 9.15 (1H, s), 11.0 (1H, s).

Example 52

In the same manner as in Example 43, a compound of Example 52 was synthesized using a compound of Example 21 and 4-isopropylbenzaldehyde as starting materials.
MS (ESI) m/z 370.9 (M–H)–

Example 53

In the same manner as in Example 43, a compound of Example 53 was synthesized using a compound of Example 21 and 4-acetamidobenzaldehyde as starting materials.
MS (ESI) m/z 385.9 (M–H)–

Example 54

In the same manner as in Example 43, a compound of Example 54 was synthesized using a compound of Example 21 and 4-phenylbenzaldehyde as starting materials.
MS (ESI) m/z 405.1 (M–H)–

Example 55

A compound of Example 53 (35.0 mg, 0.09 mmol) was stirred with heating in conc. hydrochloric acid (5 ml) at 70° C. for 2 hrs. Water (2 ml) was poured into the reaction mixture and the precipitated crystals were collected by filtration and dried to give a hydrochloride (3.4 mg, 0.01 mmol, 11%) of a compound of Example 55 as red crystals.
MS (ESI) m/z 346.2 (M+H)+, m/z 344.4 (M–H)–

Example 56

In the same manner as in Example 43, a compound of Example 56 was synthesized using a compound of Example 21 and 3,4-dihydroxybenzaldehyde as starting materials.
MS (ESI) m/z 360.9 (M–H)–

Example 57

In the same manner as in Example 43, a compound of Example 57 was synthesized using a compound of Example 21 and 3-hydroxybenzaldehyde as starting materials.
MS (ESI) m/z 345.2 (M–H)–

Example 58

In the same manner as in Example 43, a compound of Example 58 was synthesized using a compound of Example 21 and 4-methoxycarbonylbenzaldehyde as starting materials.
MS (ESI) m/z 387.2 (M–H)–

Example 59

In the same manner as in Example 43, a compound of Example 59 was synthesized using a compound of Example 21 and 3,5-dihydroxybenzaldehyde as starting materials.
MS (ESI) m/z 361.1 (M–H)–

Example 60

A compound of Example 58 (21.4 mg, 0.055 mmol) was dissolved in 1,4-dioxane (0.5 ml) and conc. hydrochloric acid (0.5 ml) was added. The mixture was stirred at 70° C. After 3 hrs, water was added. The precipitated crystals were collected by filtration and dried to give a compound of Example 60 (16.4 mg, 80%).
MS (ESI) m/z 373.0 (M–H)–

Example 61

To a solution of a compound of Example 131 (68.4 mg, 0.21 mmol) in dimethylformamide (1 ml) were added sodium methoxide (37.4 mg, 0.21 mmol; 30%) and dimethyl sulfate (33.4 mg, 0.26 mmol), which had been diluted in 0.5 ml of dimethylformamide. The mixture was stirred for 1 hr. Then the reaction mixture was diluted with ethyl acetate and water. The ethyl acetate layer was washed, dried and concentrated according to conventional methods, and then purified by silica gel column chromatography (ethyl acetate-hexane mixture) to give a compound of Example 61 (32.4 mg, 45%).
MS (ESI) m/z 343.1 (M–H)–

Example 62

In the same manner as in Example 43, a compound of Example 62 was synthesized using a compound of Example 21 and indole-3-carboxyaldehyde as starting materials.
MS (ESI) m/z 368.2 (M–H)–

Example 63

In the same manner as in Example 43, a compound of Example 63 was synthesized using a compound of Example 21 and 2-benzofurancarboxyaldehyde as starting materials.
1H-NMR (300 MHz, DMSO-d6) δ 6.71 (2H, s), 7.29 (1H, t, J=7.2 Hz), 7.45-7.56 (2H, m), 7.64-7.69 (3H, m), 7.75-7.94 (3H, m), 7.94 (1H, s), 9.03 (1H, s), 11.1 (1H, s).

Example 64

In the same manner as in Example 43, a compound of Example 64 was synthesized using a compound of Example 21 and 1-methyl-2-imidazolecarboxyaldehyde as starting materials.
MS (ESI) m/z 333.1 (M–H)–

Example 65

In the same manner as in Example 43, a compound of Example 65 was synthesized using a compound of Example 21 and 4-formylimidazole as starting materials.
MS (ESI) m/z 321.3 (M+H)+

Example 66

In the same manner as in Example 43, a compound of Example 66 was synthesized using a compound of Example 21 and 6-hydroxychromene-3-carboxyaldehyde as starting materials.
MS (ESI) m/z 401.4 (M+H)+

Example 67

In the same manner as in Example 43, a compound of Example 67 was synthesized using a compound of Example 21 and 4-bromobenzaldehyde as starting materials.
MS (ESI) m/z 409.2 (M–H)–

Example 68

In the same manner as in Example 43, a compound of Example 68 was synthesized using a compound of Example 21 and 4-fluorobenzaldehyde as starting materials.
MS (ESI) m/z 346.9 (M–H)–

Example 69

In the same manner as in Example 43, a compound of Example 69 was synthesized using a compound of Example 21 and 2-bromobenzaldehyde as starting materials.
MS (ESI) m/z 409.2 (M–H)–

Example 70

In the same manner as in Example 43, a compound of Example 70 was synthesized using a compound of Example 21 and 3-bromobenzaldehyde as starting materials.
MS (ESI) m/z 408.9 (M–H)–

Example 71

In the same manner as in Example 43, a compound of Example 71 was synthesized using a compound of Example 21 and 2-methoxybenzaldehyde as starting materials.
MS (ESI) m/z 361.4 (M+H)+

Example 72

In the same manner as in Example 43, a compound of Example 72 was synthesized using a compound of Example 21 and 3-methoxybenzaldehyde as starting materials.
MS (ESI) m/z 361.3 (M+H)+

Example 73

In the same manner as in Example 43, a compound of Example 73 was synthesized using a compound of Example 21 and 2,6-dimethoxybenzaldehyde as starting materials.
MS (ESI) m/z 391.4 (M+H)+

Example 74

In the same manner as in Example 43, a compound of Example 74 was synthesized using a compound of Example 21 and 2,4,6-trimethoxybenzaldehyde as starting materials.
MS (ESI) m/z 421.3 (M+H)+

Example 75

A compound of Example 21 (121.0 mg, 0.5 mmol) was suspended in DMF (4 ml) and sodium hydride (20 mg, 0.5 mmol, 60% oil susp.) was added. The mixture was stirred at room temperature for 3 min, and a solution (1 ml) of cyclohexylaldehyde (56.4 mg, 0.5 mmol) in DMF was slowly added dropwise. The mixture was stirred overnight at room temperature. Water was added to the reaction mixture and the mixture was extracted with a mixed solvent of ethyl acetate:hexane=1:3. The extract was washed, dried and concentrated according to conventional methods, and purified by silica gel column chromatography (ethyl acetate-hexane mixture) to give a compound of Example 75 (42.9 mg, 0.13 mmol, 26%) as yellow-white crystals.
MS (ESI) m/z 337.2 (M+H)+, m/z 335.9 (M–H)–

Example 76

A compound of Example 21 (60 mg, 0.25 mmol) was dissolved in DMF (5 ml) and sodium hydride (10 mg, 0.25 mmol, 60% oil susp.) was added. The mixture was stirred at room temperature for 5 min, and a solution (1 ml) of isobutylaldehyde (18 mg, 0.25 mmol) in DMF was slowly added dropwise. The mixture was stirred at room temperature for 10 min. Water was added to the reaction mixture and the mixture was extracted with a mixed solvent of ethyl acetate:hexane=1:3. The extract was washed, dried and concentrated according to conventional methods, and purified by silica gel column chromatography (ethyl acetate-hexane mixture) to give a compound of Example 76 (7.6 mg, 0.026 mmol, 10%) as white crystals.
MS (ESI) m/z 295.0 (M–H)–

Example 77

A compound of Example 21 (121 mg, 0.5 mmol) was suspended in THF (5 ml) and sodium hydride (20 mg, 0.5 mmol, 60% oil susp.) was added. The mixture was stirred at room temperature for 5 min, and a solution (1 ml) of n-butylaldehyde. (36 mg, 0.5 mmol) in THF was slowly added dropwise. The mixture was stirred at room temperature for 5 hrs. Water was added to the reaction mixture and the mixture was extracted with ethyl acetate. The extract was washed, dried and concentrated according to conventional methods, and purified by silica gel column chromatography (ethyl acetate-hexane mixture) to give a compound of Example 77 (32.7 mg, 0.11 mmol, 22%) as yellow-white crystals.
MS (ESI) m/z 294.9 (M–H)–

Example 78

In the same manner as in Example 77, a compound of Example 78 was synthesized using a compound of Example 21 and 3-(methylthio)-propionaldehyde as starting materials;
1H-NMR (300 MHz, DMSO-d6) δ 2.05 (3H, s), 2.73 (2H, t, J=7.2 Hz), 3.11-3.19 (2H, m), 6.54 (2H, s), 7.26 (1H, t, J=7.2 Hz), 7.45-7.47 (1H, m), 7.54-7.59 (4H, m), 10.7 (1H, s).

Example 79

A compound of Example 21 (121 mg, 0.5 mmol) was dissolved in DMF (6 ml) and sodium hydride (20 mg, 0.5 mmol, 60% oil susp.) was added. The mixture was stirred at room temperature for 2 min and a solution (1 ml) of 4-pyridylaldehyde (53.5 mg, 0.5 mmol) in DMF was slowly added dropwise. The mixture was stirred at room temperature for 10 min. Water was added to the reaction mixture and the mixture was extracted with a mixed solvent of ethyl acetate:hexane=1:1. After washing, drying and concentration according to conventional methods, crude crystals were washed with ethyl acetate and dried to give a compound of Example 79 (2.9 mg, 0.009 mmol, 2%) as orange crystals.
MS (ESI) m/z 332.3 (M+H)+

Example 80

In the same manner as in Example 79, a compound of Example 80 was synthesized using a compound of Example 21 and 3-pyridylaldehyde as starting materials.
MS (ESI) m/z 332.3 (M+H)+, m/z 329.9 (M–H)–

Example 81

In the same manner as in Example 79, a compound of Example 81 was synthesized using a compound of Example 21 and 2-pyridylaldehyde as starting materials.
MS (ESI) m/z 332.3 (M+H)+, m/z 330.1 (M–H)–

Example 82

A compound of Example 21 (121 mg, 0.5 mmol) was suspended in THF (6 ml) and sodium hydride (20 mg, 0.5 mmol, 60% oil susp.) was added. The mixture was stirred at room temperature for 5 min and a suspension (1 ml) of 2-thiophenecarboxyaldehyde (56.1 mg, 0.5 mmol) in THF was slowly added dropwise. The mixture was stirred overnight under an argon atmosphere with heating at 50° C. Water was added to the reaction mixture and the mixture was extracted with ethyl acetate. After washing, drying and concentration according to conventional methods, crude crystals were washed with hexane and dried to give a compound of Example 82 (88.2 mg, 0.26 mmol, 53%) as brown crystals.
MS (ESI) m/z 334.8 (M–H)–

Example 83

In the same manner as in Example 82, a compound of Example 83 was synthesized using a compound of Example 21 and 2-furylaldehyde as starting materials.
MS (ESI) m/z 319.0 (M+H)+

Example 84

In the same manner as in Example 82, a compound of Example 84 was synthesized using a compound of Example 21 and 2-pyrrolylaldehyde as starting materials.
MS (ESI) m/z 318.1 (M+H)+

Example 85

A compound of Example 21 (121 mg, 0.5 mmol) was suspended in THF (6 ml). Sodium hydride (20 mg, 0.5 mmol, 60% oil susp.) was added at room temperature and the mixture was stirred for 3 min. A suspension (2 ml) of n-heptylaldehyde (57.1 mg, 0.5 mmol) in THF was slowly added dropwise and the mixture was stirred at room temperature for 1 hr. Water was added to the reaction mixture and the mixture was extracted with ethyl acetate. The extract was washed, dried and concentrated according to conventional methods, and purified by silica gel column chromatography (ethyl acetate-hexane mixture) to give a compound of Example 85 (80.3 mg, 0.24 mmol, 48%) as yellow-white crystals.
MS (ESI) m/z 337.0 (M–H)–

Example 86

A compound of Example 21 (60 mg, 0.25 mmol) was dissolved in dimethoxymethyl acetal (4 ml), cooled to 0° C. and a 1.0 M solution (0.25 ml, 0.25 mmol) of titanium tetrachloride in dichloromethane was added dropwise. The mixture was stirred overnight at room temperature. The precipitated crystals were collected by filtration, washed with ethyl acetate and dried to give a compound of Example 86 (32.9 mg, 0.12 mmol, 49%) as orange white crystals.
MS (ESI) m/z 267 (M+H)+

Example 87

A compound of Example 21 (60 mg, 0.25 mmol) was dissolved in cyclohexanone (4 ml) and cooled to 0° C. A 1.0 M solution (0.25 ml, 0.25 mmol) of titanium tetrachloride in dichloromethane was added dropwise, and the mixture was stirred overnight at room temperature. The solvent was evaporated under reduced pressure, and crude crystals were separated and purified by silica gel column chromatography (ethyl acetate-hexane mixture) to give a compound of Example 87 (17.9 mg, 0.06 mmol, 11%) as an oily product.
MS (ESI) m/z 321.3 (M–H)–

Example 88

In the same manner as in Example 87, a compound of Example 88 was synthesized as a diastereomer mixture using a compound of Example 21 and ethyl methyl ketone as starting materials.
MS (ESI) m/z 295.0 (M–H)–

Example 89

In the same manner as in Example 87, a compound of Example 89 was synthesized using a compound of Example 21 and cyclopentanone as starting materials.
MS (ESI) m/z 307.2 (M–H)–

Example 90

In the same manner as in Example 87, a compound of Example 90 was synthesized using a compound of Example 21 and cycloheptanone as starting materials.
MS (ESI) m/z 335.1 (M–H)–

Example 91

In the same manner as in Example 87, a compound of Example 91 was synthesized using a compound of Example 21 and cyclobutanone as starting materials.
MS (ESI) m/z 293.2 (M–H)–

Example 92

In the same manner as in Example 87, a compound of Example 92 was synthesized using a compound of Example 21 and tetrahydro-4H-pyran-4-one as starting materials.
MS (ESI) m/z 323.3 (M–H)–

Example 93

In the same manner as in Example 3, a compound of Example 93 was synthesized using 1-hydrazinophthalazine hydrochloride and 2-amino-1,1,3-tricyano-1-propene as starting materials.
MS (ESI) m/z 293 (M–H)–

Example 94

A compound of Example 131 (130 mg, 0.39 mmol) was suspended in ethanol (25 ml) and palladium carbon (5% Pd, 50% wet, 11 mg) was added. The mixture was stirred overnight at room temperature under a hydrogen atmosphere. The reaction mixture was filtered through celite and the solvent was evaporated. Crude crystals were purified by silica gel column chromatography (ethyl acetate-hexane mixture) to give a compound of Example 94 (17.0 mg, 0.053 mmol, 13%) as yellow-white crystals.

Example 95

In the same manner as in Example 1, a compound of Example 95 was synthesized using p-bromophenylhydrazine and 2-amino-1,1,3-tricyano-1-propene as starting materials.
MS (ESI) m/z 321, 323 (M+H)+

Example 96

In the same manner as in Example 1, a compound of Example 3096 was synthesized using 2,4,6-trimethylphenylhydrazine hydrochloride and 2-amino-1,1,3-tricyano-1-propene as starting materials.
MS (ESI) m/z 285 (M+H)+, m/z 283 (M–H)–

Example 97

In the same manner as in Example 3, a compound of Example 97 was synthesized using 2,2,2-trifluoroethylhydrazine and 2-amino-1,1,3-tricyano-1-propene as starting materials.
MS (ESI) m/z 247 (M–H)–

Example 98

Step 1

To a solution (2 ml) of 5-amino-4-cyano-3-cyanomethyl-1-phenylpyrazole (100 mg, 0.45 mmol) in THF were added successively sodium hydride (54 mg, 1.35 mmol, 60% oil susp.) and 1,2-dibromoethane (126 mg, 0.67 mmol), and the mixture was stirred at 60° C. for 7 hrs. The reaction mixture was poured into water and the mixture was extracted with ethyl acetate. The extract was washed, dried and concentrated according to conventional methods, and purified by silica gel column chromatography (ethyl acetate-hexane mixture) to give a cyclopropane compound (intermediate 16 of Synthetic Method 6 wherein $R_1$ is phenyl group) (17 mg, 14.5%) as white crystals.
MS (ESI) m/z 248 (M–H)–

Step 2

The cyclopropane compound (16 mg) obtained in Step 1 was added to conc. hydrochloric acid (1 ml) and the mixture was stirred at 70° C. for 2 hrs. Water was added and the resulting precipitate was collected by filtration and purified by thin-layer silica gel chromatography (ethyl acetate-hexane mixture) to give a compound of Example 98 (2 mg, 11.6%) as yellow-white crystals.
MS (ESI) m/z 267 (M–H)–

Example 99

Step 1

To a solution (3 ml) of 5-amino-4-cyano-3-cyanomethyl-1-phenylpyrazole (200 mg, 0.90 mmol) and benzaldehyde (380 mg, 3.58 mmol) in toluene was added one drop of conc. sulfuric acid and the mixture was stirred overnight at 110° C. The reaction mixture was poured into water and the mixture was extracted with ethyl acetate. The extract was washed, dried and concentrated according to conventional methods, and purified by silica gel chromatography (ethyl acetate-hexane mixture) to give an imine compound (intermediate 5 of Synthetic Method 2 wherein $R_1$ is phenyl group and R is phenyl group)(279 mg, 100%) as yellow crystals
MS (ESI) m/z 310 (M–H)–

Step 2

To a solution (50 ml) of imine compound (243 mg, 0.78 mmol) obtained in Step 1 in ethanol was added sodium borohydride (60 mg, 1.58 mmol), and the mixture was stirred at room temperature for 1 hr. After adding water, ethanol was evaporated under reduced pressure and the resulting mixture was extracted with ethyl acetate, and washed, dried and concentrated according to conventional methods to give a reduced imine compound (intermediate 6 of Synthetic Method 2 wherein $R_1$ is phenyl group and R is phenyl group) (232 mg, 94.7%) as a yellow oil.
MS (ESI) m/z 312 (M–H)–

Step 3

The reduced imine compound (151 mg, 0.48 mmol) obtained in Step 2 was added to conc. hydrochloric acid (2 ml) and the mixture was stirred at 70° C. for 3 hrs. Water was added and the resulting precipitate was collected by filtration and dried in vacuo to give a compound of Example 99 (101 mg, 63.1%) as white crystals.
MS (ESI) m/z 331 (M–H)–

Example 100

In the same manner as in Steps 1-3 of Example 99, a compound of Example 100 was synthesized using 5-amino-4-cyano-3-cyanomethyl-1-phenylpyrazole and p-chlorobenzaldehyde as starting materials.
MS (ESI) m/z 367 (M+H)+, m/z 365 (M–H)–

Example 101

In the same manner as in Steps 1-3 of Example 99, a compound of Example 101 was synthesized using 5-amino-4-cyano-3-cyanomethyl-1-phenylpyrazole and o-chlorobenzaldehyde as starting materials.
MS (ESI) m/z 367 (M+H)+

Example 102

In the same manner as in Steps 1-3 of Example 99, a compound of Example 102 was synthesized using 5-amino-4-cyano-3-cyanomethyl-1-phenylpyrazole and p-fluorobenzaldehyde as starting materials.
MS (ESI) m/z 351 (M+H)+, m/z 349 (M–H)–

Example 103

In the same manner as in Steps 1-3 of Example 99, a compound of Example 103 was synthesized using 5-amino-4-cyano-3-cyanomethyl-1-phenylpyrazole and p-cyanobenzaldehyde as starting materials.
MS (ESI) m/z 358 (M+H)+, m/z 356 (M–H)–

Example 104

In the same manner as in Steps 1-3 of Example 99, a compound of Example 104 was synthesized using 5-amino-4-cyano-3-cyanomethyl-1-phenylpyrazole and m-chlorobenzaldehyde as starting materials.
MS (ESI) m/z 367 (M+H)+, m/z 365 (M–H)–

Example 105

In the same manner as in Steps 1-3 of Example 99, a compound of Example 105 was synthesized using 5-amino-4-cyano-3-cyanomethyl-1-phenylpyrazole and m-hydroxybenzaldehyde as starting materials.
MS (ESI) m/z 349 (M+H)+, m/z 347 (M–H)–

Example 106

In the same manner as in Steps 1-3 of Example 99, a compound of Example 106 was synthesized using 5-amino- 4-cyano-3-cyanomethyl-1-phenylpyrazole and propionaldehyde as starting materials.
MS (ESI) m/z 285 (M+H)+, m/z 283 (M–H)–

Example 107

In the same manner as in Steps 1-3 of Example 99, a compound of Example 107 was synthesized using 5-amino-4-cyano-3-cyanomethyl-1-phenylpyrazole and cyclohexanecarboxyaldehyde as starting materials.
MS (ESI) m/z 337 (M–H)–

Example 108

In the same manner as in Steps 1-3 of Example 99, a compound of Example 108 was synthesized using 5-amino-4-cyano-6-3-cyanomethyl-1-phenylpyrazole and n-heptaldehyde as starting materials.
MS (ESI) m/z 341 (M+H)+, m/z 339 (M–H)–

Example 109 and Example 110

In the same manner as in Steps 1-3 of Example 99, a compound of Example 109 was synthesized using 5-amino-4-cyano-3-cyanomethyl-1-phenylpyrazole and 4-methoxycarbonylbenzaldehyde as starting materials. In Step 3, moreover, a compound of Example 110 was also obtained as a byproduct.
Example 109 compound: MS (ESI) m/z 389 (M–H)–
Example 110 compound: MS (ESI) m/z 375 (M–H)–

Example 111

In the same manner as in Steps 1-3 of Example 99, a compound of Example 111 was synthesized using 5-amino-4-cyano-3-cyanomethyl-1-methylpyrazole and benzaldehyde as starting materials.
1H-NMR (300 MHz, DMSO-d6) δ 3.57 (3H, s), 3.62 (2H, s), 4.95 (2H, d, J=6.6 Hz), 6.88 (1H, t, J=6.6 Hz), 7.18-7.32 (5H, m), 10.40 (1H, s).

Example 112

In the same manner as in Steps 1-3 of Example 99, a compound of Example 112 was synthesized using 5-amino-4-cyano-3-cyanomethyl-1-methylpyrazole and 3-hydroxybenzaldehyde as starting materials.
1H-NMR (300 MHz, DMSO-d6) δ 3.14-3.22 (1H, m), 3.26-3.33 (1H, m), 4.07 (1H, t, J=4.5 Hz), 6.34 (2H, t), 6.53 (2H, d, J=9.0 Hz), 6.80 (2H, d, J=9.0 Hz), 7.40-7.58 (5H, m), 9.14 (1H, s), 10.44 (1H, s).

Example 113

In the same manner as in Steps 1-3 of Example 99, a compound of Example 113 was synthesized using 5-amino-4-cyano-3-cyanomethyl-1-methylpyrazole and 4-methoxycarbonylbenzaldehyde as starting materials.
MS (ESI) m/z 327 (M–H)–

Example 114

To a solution (10 ml) of a compound of Example 46 (108 mg, 0.312 mmol) in ethanol was added palladium carbon (10 mg) and the mixture was stirred at room temperature under a hydrogen atmosphere for 1 hr. The mixture was filtered, washed with ethyl acetate and concentrated under reduced pressure to give a compound of Example 114 (95 mg, 87.2%) as white crystals.
1H-NMR (300 MHz, DMSO-d6) δ 3.14-3.34 (2H, m), 4.07 (1H, t, J=4.5 Hz), 6.34 (2H, s), 6.53 (2H, d, J=9.0 Hz), 6.80 (2H, d, J=9.0 Hz), 7.40-7.58 (5H, m), 9.14 (1H, s), 10.46 (1H, s).

Example 115

To a solution (2 ml) of a compound of Example 21 (100 mg, 0.413 mmol) in DMF were added trifluoromethanesulfonic acid (1 ml) and then sodium nitrite (100 mg, 1.45 mmol) under ice-cooling, and the mixture was stirred at room temperature for 10 min. Water was added to the reaction mixture and the mixture was extracted with ethyl acetate. The extract was washed, dried and concentrated according to conventional methods to give yellow crystals. Thereto was added ethyl acetate-hexane (1:1, 3 ml) and the mixture was stirred and filtered to give a compound of Example 115 (20 mg, 30.8%) as brown crystals.
MS(FAB) m/z 257 (M+H)+

Example 116

To a solution (2 ml) of Example 131 (68 mg, 0.206 mmol) in DMF were added trifluoromethanesulfonic acid (1 ml) and then sodium nitrite (50 mg, 0.725 mmol) under ice-cooling, and the mixture was stirred at room temperature for 10 min. Water and ethyl acetate were added to the reaction mixture and the resulting precipitate was collected by filtration to give a compound of Example 116 (20 mg, 30.8%) as brown crystals.
MS (FAB) m/z 316 (M+H)+

Example 117

In the same manner as in Example 1, a compound of Example 117 was synthesized using 4-hydrazinobenzoic acid and 2-amino-1,1,3-tricyano-1-propene as starting materials.
MS (ESI) m/z 287 (M+H)+

Example 118

In the same manner as in Example 1, a compound of Example 118 was synthesized using 3-hydrazinobenzoic acid and 2-amino-1,1,3-tricyano-1-propene as starting materials.
MS (ESI) m/z 287 (M+H)+

Example 119

In the same manner as in Example 1, a compound of Example 119 was synthesized using 2-hydrazinobenzoic acid and 2-amino-1,1,3-tricyano-1-propene as starting materials.
MS (ESI) m/z 287 (M+H)+

Example 120

In the same manner as in Example 1, a compound of Example 120 was synthesized using 1-naphthylhydrazine and 2-amino-1,1,3-tricyano-1-propene as starting materials.
MS (ESI) m/z 293 (M+H)+

Example 121

In the same manner as in Example 1, a compound of Example 121 was synthesized using 2-hydrazinoquinoline and 2-amino-1,1,3-tricyano-1-propene as starting materials.
MS (ESI) m/z 294 (M+H)+

Example 122

In the same manner as in Example 1, a compound of Example 122 was synthesized using phenethylhydrazine and 2-amino-1,1,3-tricyano-1-propene as starting materials.
MS (ESI) m/z 271 (M+H)+

Example 123

In the same manner as in Example 3, a compound of Example 123 was synthesized using 3-propylphenylhydrazine hydrochloride and 2-amino-1,1,3-tricyano-1-propene as starting materials.
MS (ESI) m/z 285 (M+H)+

Example 124

In the same manner as in Example 1, a compound of Example 124 was synthesized using p-fluorophenylhydrazine and 2-amino-1,1,3-tricyano-1-propene as starting materials.
MS (ESI) m/z 261 (M+H)+

Example 125

In the same manner as in Example 1, a compound of Example 125 was synthesized using pentafluorophenylhydrazine and 2-amino-1,1,3-tricyano-1-propene as starting materials.
MS (ESI) m/z 333 (M+H)+

Example 126

A solution of a compound of Example 117 (140 mg), WSC (150 mg), HOBt (100 mg) and n-pentylamine (80 µg) in DMF was stirred overnight at room temperature and aqueous hydrochloric acid solution was added. The mixture was extracted with ethyl acetate, dried over magnesium sulfate and concentrated. Acetonitrile was added to the obtained residue and the resulting crystals were collected by filtration and further washed with acetonitrile to give a compound of Example 126 (90 mg) as yellow crystals.
MS (ESI) m/z 356 (M+H)+

Example 127

In the same manner as in Example 126, a compound of Example 127 was synthesized using a compound of Example 118 as a starting material.
MS (ESI) m/z 356 (M+H)+

Example 128

Triethylamine (80 µl) was added to a solution (5 ml) of a compound of Example 117 (140 mg) in acetone and ethyl chlorocarbonate (60 µl) was added in an ice bath. The mixture was stirred at 0° C. for 30 min. To this solution was added a solution of sodium azide (40 mg) dissolved in water (0.5 ml) and the mixture was stirred at 0° C. for 1.5 hrs. Water was added and the mixture was extracted with ethyl acetate, dried over sodium sulfate and concentrated. Toluene (10 ml) and benzyl alcohol (0.5 ml) were added to the obtained residue and the mixture was stirred overnight at 80° C. After concentration, ethanol was added and the resulting crystals were collected by filtration to give a compound of Example 128 (30 mg).
MS (ESI) m/z 392 (M+H)+

Example 129

In the same manner as in Example 128, a compound of Example 129 was obtained using a compound of Example 118 as a starting material and ethanol instead of benzyl alcohol.
MS (ESI) m/z 330 (M+H)+

Example 130

In the same manner as in Example 128, a compound of Example 130 was synthesized using a compound of Example 118 as a starting material.
MS (ESI) m/z 392 (M+H)+

Example 131

In the same manner as in Example 43, a compound (61 mg) of Example 131 was obtained using a compound (55 mg) of Example 21 and benzaldehyde (80 µl) as starting materials.
MS (ESI) m/z 331 (M+H)+

Example 132

In the same manner as in Example 43, a compound of Example 132 was synthesized using a compound of Example 2 and benzaldehyde as starting materials.
MS (ESI) m/z 268 (M+H)+

Example 133

In the same manner as in Example 43, a compound of Example 133 was synthesized using a compound of Example 21 and pentafluorobenzaldehyde as starting materials.
MS (ESI) m/z 421 (M+H)+

Example 134

In the same manner as in Example 43, a compound of Example 134 was synthesized using a compound of Example 95 and benzaldehyde as starting materials.
MS (ESI) m/z 409, 411 (M+H)+

Example 135

A compound of Example 21 (30 mg) and methanesulfonic acid (catalytic amount) were stirred overnight in acetone at 70° C. and the solid was collected by filtration to synthesize a compound of Example 135 (23 mg).
MS (ESI) m/z 283 (M+H)+

Example 136

A compound of Example 21 (60 mg) and ethyl pyruvate (100 mg) were stirred overnight in ethanol (3 ml) together with a catalytic amount of methanesulfonic acid at 70° C. and the resulting solid was collected by filtration to synthesize a compound of Example 136.
MS (ESI) m/z 341 (M+H)+

Example 137

A compound of Example 21 (60 mg) and nitrosobenzene (100 mg) were stirred overnight in ethanol/acetic acid (1:1)(5 ml) at room temperature, and the resulting solid was collected by filtration to synthesize a compound of Example 137 (66 mg).
MS (ESI) m/z 348 (M+H)+

Example 138

In the same manner as in Example 137, a compound of Example 138 was synthesized using a compound of Example 21 and 4-dimethylaminonitrosobenzene as starting materials.
MS (ESI) m/z 391 (M+H)+

Example 139

A compound of Example 137 (500 mg) was added to ethanol (20 ml), and conc. hydrochloric acid (3 ml) was further added. The mixture was stirred overnight at 50° C., cooled to 0° C. and the resulting solid was collected by filtration and washed with ethanol to give a compound of Example 139 (240 mg).
MS (ESI) m/z 257 (M+H)+

Example 140

A compound of Example 139 (50 mg), p-toluidine (100 mg) and a catalytic amount of acetic acid were stirred overnight in ethanol (3 ml) at 80° C., and the resulting solid was collected by filtration to give a compound of Example 140 (46 mg).
1H-NMR (300 MHz, DMSO-d6) δ 2.28 (3H, s), 6.64-7.65 (11H, m), 11.23 (1H, s).

Example 141

In the same manner as in Example 140, a compound of Example 141 was synthesized using a compound of Example 139 and phenylhydrazine as starting materials.
MS (ESI) m/z 347 (M+H)+

Example 142

In the same manner as in Example 140, a compound of Example 142 was synthesized using a compound of Example 139 and hydroxylamine sulfate as starting materials.
1H-NMR (300 MHz, DMSO-d6) δ 6.60 (2H, br s), 7.44-7.64 (5H, m), 10.99 (1H, s), 13.57 (1H, s).

Example 143

In the same manner as in Example 140, a compound of Example 143 was synthesized using a compound of Example 139 and o-methylhydroxylamine as starting materials.
1H-NMR (300 MHz, DMSO-d6) δ 4.18 (3H, s), 6.62 (2H, s), 7.49-7.63 (5H, m), 11.08 (1H, s).

Example 144

In the same manner as in Example 140, a compound of Example 144 was synthesized using a compound of Example 139 and semicarbazide hydrochloride as starting materials.
1H-NMR (300 MHz, DMSO-d6) δ 6.82 (2H, s), 7.03 (2H, br s), 7.50-7.64 (5H, m), 11.03 (1H, s), 11.13 (1H, s).

Example 145

In the same manner as in Example 140, a compound of Example 145 was synthesized using a compound of Example 139 and acetylhydrazine as starting materials.
1H-NMR (300 MHz, DMSO-d6) δ 2.32 (3H, s), 6.88 (2H, s), 7.52-7.69 (5H, m), 11.11 (1H, br s), 11.90 (1H, br s).

Example 146

A compound of Example 21 (30 mg) and acetyl chloride (100 μl) were stirred overnight in acetic acid (3 ml) at 70° C. and the solid was collected by filtration to give a compound of Example 146 (26 mg).
MS (ESI) m/z 284 (M+H)+

Example 147

A compound of Example 21 was stirred in trimethyl o-acetate (3 ml) overnight together with a catalytic amount of acetic acid at 70° C. and the solid was collected by filtration to give a compound of Example 147 (15 mg).
MS (ESI) m/z 284 (M+H)+

Example 148

A compound of Example 131 (70 mg), NaHSO$_3$ (100 mg) and Na$_2$S$_2$O$_5$ (100 mg) were stirred in water/methanol (1:1) (3 ml) at 70° C. for 1 hr, and water was added. The solid was collected by filtration to give a compound of Example 148.
MS (ESI) m/z 413 (M+H)+

Example 149

A compound of Example 136 (200 mg) and palladium carbon (10% Pd, 50% wet, 50 mg) were stirred overnight in ethanol (50 ml) at room temperature under a hydrogen atmosphere. The solid was collected by filtration and washed with ethyl acetate. The washing was concentrated to give a compound of Example 149 (diastereomer mixture).
MS (ESI) m/z 343 (M+H)+

Example 150

A compound of Example 139 (50 mg) and palladium carbon (20 mg) were stirred overnight in ethanol (10 ml) at room temperature under a hydrogen atmosphere. The solid was collected by filtration and washed with ethyl acetate and ethanol. The solution was concentrated to give a compound of Example 150 as a yellow solid (14 mg).
MS (ESI) m/z 259 (M+H)+

Example 151

A compound of Example 7 (50 mg) was added to dichloromethane (10 ml) and 1.0 M solution (1.2 ml) of BBr$_3$ in dichloromethane was added. The mixture was stirred overnight at room temperature. Water was added and dichloromethane was evaporated. The resulting solid was collected by filtration and washed with water and ethanol to give a compound of Example 151.
MS (ESI) m/z 259 (M+H)+

Example 152

In the same manner as in Example 151, a compound of Example 152 was synthesized using a compound of Example 16 as a starting material.
MS (ESI) m/z 259 (M+H)+

Example 153

In the same manner as in Example 151, a compound of Example 153 was synthesized using a compound of Example 17 as a starting material.
MS (ESI) m/z 259 (M+H)+

Example 154

To a solution (5 ml) of ethyl (5-oxo-1-phenyl-4,5-dihydro-1H-pyrazol-3-yl)acetate (30 mg) in THF were added potassium carbonate (50 mg) and benzyl isocyanate (100 µl) and the mixture was stirred overnight at room temperature. The solid was collected by filtration and washed with THF. The washing was concentrated and the residue was stirred overnight at 70° C. in conc. hydrochloric acid (2 ml). The resulting mixture was diluted with water and the resulting solid was collected by filtration and washed with water to give a compound of Example 154 (11 mg).
MS (ESI) m/z 334 (M+H)+

Example 155

In the same manner as in Example 154, a compound of Example 155 was synthesized using ethyl (5-oxo-1-phenyl-4,5-dihydro-1H-pyrazol-3-yl)acetate and ethyl isocyanate as starting materials.
MS (ESI) m/z 272 (M+H)+

Example 156

In the same manner as in Example 154, a compound of Example 156 was synthesized using ethyl (5-oxo-1-phenyl-4,5-dihydro-1H-pyrazol-3-yl)acetate and methyl isothiocyanate as starting materials.
MS (ESI) m/z 274 (M+H)+

Example 157

In the same manner as in Example 154, a compound of Example 157 was synthesized using ethyl (5-oxo-1-phenyl-4,5-dihydro-1H-pyrazol-3-yl)acetate and benzyl isothiocyanate as starting materials.
MS (ESI) m/z 350 (M+H)+

Example 158 t-Butyl carbazate (1.32 g), 3-pentanone (1.06 ml) and acetic acid (0.3 ml) are stirred overnight in ethanol (30 ml) at 80° C. The solution is concentrated and dissolved in acetic acid (20 ml) and the mixture is stirred in the presence of 10% palladium carbon catalyst (0.5 g) under a hydrogen atmosphere for 50 hrs. The catalyst is filtered off and the mixture is washed with ethyl acetate. The solution is concentrated and dissolved in 4 Mol hydrochloric acid-ethyl acetate solution (10 ml). After stirring at room temperature for 5 hrs, the solution is concentrated to dryness to give 3-pentylhydrazine hydrochloride. A compound of Example 158 is synthesized from the obtained hydrazine hydrochloride according to a method similar to the method of Example 3.
MS (ESI) m/z 237 (M+H)+

Example 159

In the same manner as in Example 158, a compound of Example 159 was synthesized using tetrahydro-4H-pyran-4-one as a starting material.
MS (ESI) m/z 251 (M+H)+

Example 160

In the same manner as in Example 158, a compound of Example 160 was synthesized using cyclohexanecarboxyaldehyde as a starting material.
MS (ESI) m/z 263 (M+H)+

Example 161

In the same manner as in Example 158, a compound of Example 161 was synthesized using cyclopentanone as a starting material.
MS (ESI) m/z 235 (M+H)+

Example 162

In the same manner as in Example 158, a compound of Example 162 was synthesized using 4-heptanone as a starting material.
MS (ESI) m/z 265 (M+H)+

Example 163

In the same manner as in Example 158, a compound of Example 163 was synthesized using 4,4-dimethyl-2-cyclohexen-1-one as a starting material.
MS (ESI) m/z 277 (M+H)+

Example 164

In the same manner as in Example 158, a compound of Example 164 was synthesized using hexanal as a starting material.
MS (ESI) m/z 251 (M+H)+

Example 165

In the same manner as in Example 158, a compound of Example 165 was synthesized using 1-methyl-4-piperidone as a starting material.
MS (ESI) m/z 264 (M+H)+

Example 166

In the same manner as in Example 158, a compound of Example 166 was synthesized using 1-t-butoxycarbonyl-4-piperidone as a starting material.
MS (ESI) m/z 250 (M+H)+

Example 167

In the same manner as in Example 158, a compound of Example 167 was synthesized using 2-ethylbutylaldehyde as a starting material.
MS (ESI) m/z 251 (M+H)+

Example 168

Step 1 t-Butyl carbazate (2.6 g), 2,2-dimethoxypropane (3 ml) and a catalytic amount of acetic acid are stirred overnight in ethanol (20 ml), and the solution is concentrated to give an isopropylidene-protected compound (3.4 g) as a solid.

Step 2

The intermediate (0.86 g) obtained in Step 1, 2-bromoethyl ethyl ether (0.77 g) and sodium hydride (250 mg) are stirred overnight in acetonitrile (30 ml) at 80° C. Water is added and the mixture is extracted with ethyl acetate. After drying over sodium sulfate, the solvent is evaporated. The obtained residue is stirred overnight in 4 Mol hydrochloric acid-ethyl acetate solution (10 ml) at room temperature, and the solvent is evaporated. The obtained residue is dissolved in ethanol (20 ml) and conc. hydrochloric acid (5 ml) is added. The mixture is stirred overnight at room temperature, concentrated to dryness and washed with ethyl acetate to give 2-ethoxyethylhydrazine hydrochloride (0.4 g). A compound of Example 168 was synthesized according to a method similar to the method of Example 3 from the obtained hydrazine hydrochloride.
MS (ESI) m/z 239 (M+H)+

Example 169

The intermediate (1.76 g) obtained in Step 1 of Example 168, 4-methylbenzylbromide (1.85 g) and sodium hydride (300 mg) are stirred overnight in acetonitrile (30 ml) at 80° C. Water is added and the mixture is extracted with ethyl acetate. After drying over sodium sulfate, the solvent is evaporated. The obtained residue is stirred overnight in 4 Mol hydrochloric acid-ethyl acetate solution (10 ml) at room temperature, and the solvent is evaporated. The obtained residue is dissolved in ethanol (20 ml) and conc. hydrochloric acid (5 ml) is added. The mixture is stirred overnight at room temperature, concentrated to dryness and washed with ethyl acetate to give 4-methylbenzylhydrazine hydrochloride (1.9 g). A compound of Example 169 was synthesized according to a method similar to the method of Example 3 from the obtained hydrazine hydrochloride.
MS (ESI) m/z 272 (M+H)+

Example 170

In the same manner as in Example 158, a compound of Example 170 was synthesized using salicyl aldehyde as a starting material.
MS (ESI) m/z 273 (M+H)+

Example 171

In the same manner as in Example 169, a compound of Example 171 was synthesized using 2,6-dichlorobenzylbromide as a starting material.
MS (ESI) m/z 325, 327, 329 (M+H)+

Example 172

In the same manner as in Example 169, a compound of Example 172 was synthesized using 1-chloromethylnaphthalene as a starting material.
MS (ESI) m/z 307 (M+H)+

Example 173

In the same manner as in Example 169, a compound of Example 173 was synthesized using 2-chloromethylnaphthalene as a starting material.
MS (ESI) m/z 307 (M+H)+

Example 174

In the same manner as in Example 169, a compound of Example 174 was synthesized using methyl 4-bromomethylbenzoate as a starting material.
MS (ESI) m/z 301 (M+H)+

Example 175

In the same manner as in Example 169, a compound of Example 175 was synthesized using 4-picolyl chloride hydrochloride as a starting material.
MS (ESI) m/z 258 (M+H)+

Example 176

In the same manner as in Example 169, a compound of Example 176 was synthesized using 3-picolyl chloride hydrochloride as a starting material.
MS (ESI) m/z 258 (M+H)+

Example 177

In the same manner as in Example 169, a compound of Example 177 was synthesized using 2-picolyl chloride hydrochloride as a starting material.
MS (ESI) m/z 258 (M+H)+

Example 178

In the same manner as in Example 169, a compound of Example 178 was synthesized using 3-nitrobenzyl chloride as a starting material.
MS (ESI) m/z 302 (M+H)+

Example 179

In the same manner as in Example 169, a compound of Example 179 was synthesized using 2-fluorobenzyl chloride as a starting material.
MS (ESI) m/z 275 (M+H)+

Example 180

In the same manner as in Example 169, a compound of Example 180 was synthesized using 2-iodobenzyl chloride as a starting material.
MS (ESI) m/z 383 (M+H)+

Example 181

In the same manner as in Example 169, a compound of Example 181 was synthesized using 2-phenylbenzylbromide as a starting material.
MS (ESI) m/z 333 (M+H)+

Example 182

In the same manner as in Example 169, a compound of Example 182 was synthesized using 3-methoxybenzyl chloride as a starting material.
MS (ESI) m/z 287 (M+H)+

Example 183

A solution (2 ml) of the bromo compound (80 mg) obtained in Step 1 of Example 26, 2-aminoethanol (200 mg) and diisopropylethylamine (180 mg) in DMSO was heated at 100° C. for 20 hrs. 1M Hydrochloric acid (10 ml) was added and the mixture was extracted with ethyl acetate. The extract solution was washed with water and saturated brine, dried over sodium sulfate and the solvent was evaporated. The obtained residue was purified by silica gel column chromatography (ethyl acetate-hexane mixture) to give the object dinitrile intermediate (21 mg). The obtained intermediate was heated at 80° C. in conc. hydrochloric acid (2 ml) for 2 hrs, diluted with water and extracted with ethyl acetate. The extract solution was dried over sodium sulfate and concentrated to give a compound of Example 183 (18 mg).
MS (ESI) m/z 287 (M+H)+

Example 184

In the same manner as in Example 183, a compound of Example 184 was synthesized using dimethylamine as a starting material.
MS (ESI) m/z 271 (M+H)+

Example 185

In the same manner as in Example 183, a compound of Example 185 was synthesized using morpholine as a starting material.
MS (ESI) m/z 312 (M+H)+

Example 186

In the same manner as in Example 183, a compound of Example 186 was synthesized using pyrrolidine as a starting material.
MS (ESI) m/z 297 (M+H)+

Example 187

In the same manner as in Example 183, a compound of Example 187 was synthesized using cyclohexylamine as a starting material.
MS (ESI) m/z 325 (M+H)+

Example 188

In the same manner as in Example 183, a compound of Example 188 was synthesized using 4-hydroxypiperidine as a starting material.
MS (ESI) m/z 327 (M+H)+

Example 189

The bromo compound (50 mg) obtained in Step 1 of Example 26, tetrakistriphenyl-phosphine palladium (20 mg) and phenylboronic acid (26 mg) were dissolved in a mixture (3:1)(2 ml) of toluene and ethanol and 2 M sodium carbonate solution (0.4 ml) was added. The mixture was heated at 80° C. for 24 hrs. Water was added and the mixture was extracted with ethyl acetate. The solvent was evaporated and the obtained residue was purified by silica gel column chromatography (ethyl acetate-hexane mixture) to give the object dinitrile intermediate (40 mg). The obtained intermediate was heated at 80° C. in conc. hydrochloric acid (2 ml) for 2 hrs, and diluted with water and extracted with ethyl acetate. The extract solution was dried over sodium sulfate and concentrated. The obtained residue was purified by silica gel column chromatography (ethyl acetate-hexane mixture) to give a compound of Example 189 (5 mg).
MS (ESI) m/z 304 (M+H)+

Example 190

In the same manner as in Example 189, a compound of Example 190 was synthesized using 4-pyridylboronic acid as a starting material.
MS (ESI) m/z 305 (M+H)+

Example 191

In the same manner as in Example 189, a compound of Example 191 was synthesized using 2-thiopheneboronic acid as a starting material.
MS (ESI) m/z 310 (M+H)+

Example 192

In the same manner as in Example 189, a compound of Example 192 was synthesized using 3-thiopheneboronic acid as a starting material.
MS (ESI) m/z 310 (M+H)+

Example 193

In the same manner as in Example 189, a compound of Example 193 was synthesized using 3-methoxyphenylboronic acid as a starting material.
MS (ESI) m/z 334 (M+H)+

Example 194

The corresponding hydrazine was obtained from 5-chloro-o-anisidine according to a method described in Organic Synthesis I, p. 442. A methoxy derivative was synthesized from the obtained hydrazine according to a method described in Example 3, and a compound of Example 194, which is a hydroxy compound, was synthesized according to the method of Example 151.
MS (ESI) m/z 293, 295 (M+H)+

Example 195

In the same manner as in Example 194, a compound of Example 195 was synthesized using 2,3-dimethoxyaniline as a starting material.
MS (ESI) m/z 275 (M+H)+

Example 196

In the same manner as in Example 194, a compound of Example 196 was synthesized using 3-fluoro-o-anisidine as a starting material.
MS (ESI) m/z 277 (M+H)+

Example 197

In the same manner as in Example 194, a compound of Example 197 was synthesized using 3-amino-4-methoxybenzoic acid as a starting material.
MS (ESI) m/z 303 (M+H)+

Example 198

In the same manner as in Example 194, a compound of Example 198 was synthesized using 4-amino-3-methoxybenzoic acid as a starting material.
MS (ESI) m/z 303 (M+H)+

TABLE 1
| Ex. | structural formula |
|---|---|
| 1 | 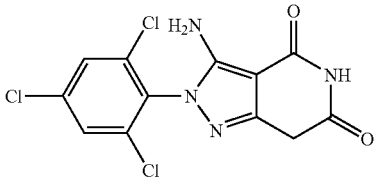 |
| 2 | 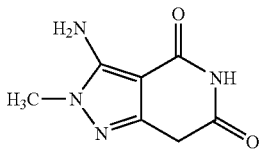 |
| 3 | 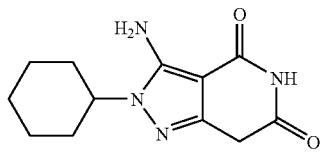 |
| 4 | 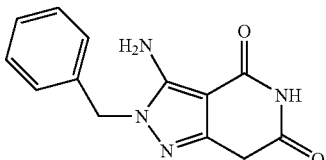 |
| 5 | 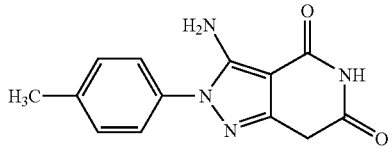 |
| 6 | 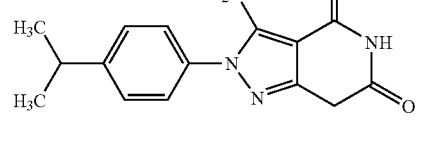 |
| 7 | 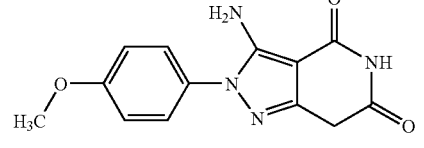 |
| 8 | 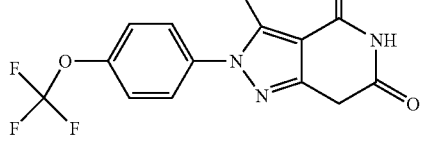 |
| 9 | 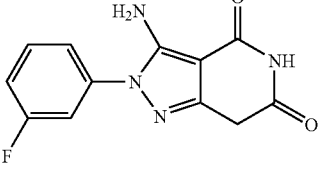 |
| 10 | 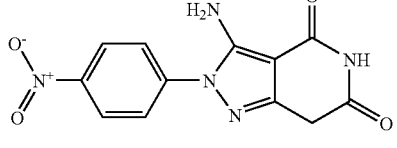 |
| 11 | 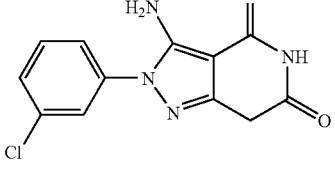 |
| 12 | 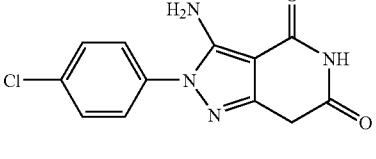 |
| 13 | 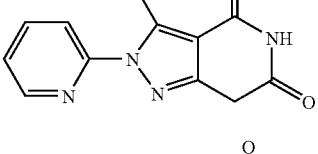 |
| 14 | 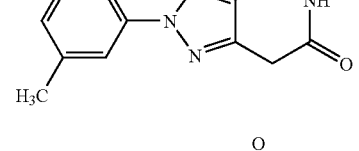 |
| 15 | 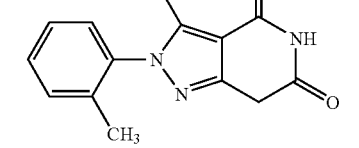 |
| 16 | 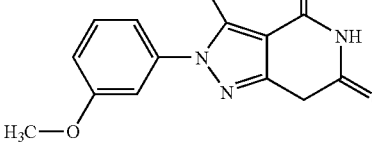 |

TABLE 2

| Ex. | structural formula |
|---|---|
| 17 | 3-amino-2-(2-methoxyphenyl) pyrazolo-pyridine-4,6-dione |
| 18 | 3-amino-2-(2-chlorophenyl) pyrazolo-pyridine-4,6-dione |
| 19 | 3-amino-2-(2,6-dichlorophenyl) pyrazolo-pyridine-4,6-dione |
| 20 | 3-amino-2-(3,4-dichlorophenyl) pyrazolo-pyridine-4,6-dione |
| 21 | 3-amino-2-phenyl pyrazolo-pyridine-4,6-dione |
| 22 | 3-amino-5-methyl-7,7-dimethyl-2-phenyl pyrazolo-pyridine-4,6-dione |
| 23 | 3-amino-7,7-dimethyl-2-phenyl pyrazolo-pyridine-4,6-dione |
| 24 | 3-chloro-2-phenyl pyrazolo-pyridine-4,6-dione |

TABLE 2-continued

| Ex. | structural formula |
|---|---|
| 25 | 2-phenyl pyrazolo-pyridine-4,6-dione |
| 26 | 3-bromo-2-phenyl pyrazolo-pyridine-4,6-dione |
| 27 | 3-iodo-2-phenyl pyrazolo-pyridine-4,6-dione |
| 28 | 3-methylthio-2-phenyl pyrazolo-pyridine-4,6-dione |
| 29 | 3-methylsulfonyl-2-phenyl pyrazolo-pyridine-4,6-dione |
| 30 | 3-amino-2-ethyl pyrazolo-pyridine-4,6-dione |

TABLE 3

| Ex. | structural formula |
|---|---|
| 31 | 3-amino-2-(2-carboxyethyl) pyrazolo-pyridine-4,6-dione |
| 32 | 3-ethylthio-2-phenyl pyrazolo-pyridine-4,6-dione |

TABLE 3-continued

| Ex. | structural formula |
|---|---|
| 33 | |
| 34 | |
| 35 | |
| 36 | |
| 37 | |
| 38 | |

TABLE 3-continued

| Ex. | structural formula |
|---|---|
| 39 | |
| 40 | |
| 41 | |
| 42 | |

TABLE 4

| Ex. | structural formula |
|---|---|
| 43 | |

TABLE 4-continued

| Ex. | structural formula |
|---|---|
| 44 | (3-amino-2-phenyl-7-(4-chlorobenzylidene)-2H-pyrazolo[4,3-c]pyridine-4,6(5H,7H)-dione) |
| 45 | (3-amino-2-phenyl-7-(4-(dimethylamino)benzylidene)-2H-pyrazolo[4,3-c]pyridine-4,6(5H,7H)-dione) |
| 46 | (3-amino-2-phenyl-7-(4-hydroxybenzylidene)-2H-pyrazolo[4,3-c]pyridine-4,6(5H,7H)-dione) |
| 47 | (3-amino-2-phenyl-7-(4-methylbenzylidene)-2H-pyrazolo[4,3-c]pyridine-4,6(5H,7H)-dione) |
| 48 | (3-amino-2-phenyl-7-(4-(trifluoromethoxy)benzylidene)-2H-pyrazolo[4,3-c]pyridine-4,6(5H,7H)-dione) |

TABLE 4-continued

| Ex. | structural formula |
|---|---|
| 49 | (3-amino-2-phenyl-7-(2-methylbenzylidene)-2H-pyrazolo[4,3-c]pyridine-4,6(5H,7H)-dione) |
| 50 | (3-amino-2-phenyl-7-(3-methylbenzylidene)-2H-pyrazolo[4,3-c]pyridine-4,6(5H,7H)-dione) |
| 51 | (3-amino-2-phenyl-7-(3,4-dichlorobenzylidene)-2H-pyrazolo[4,3-c]pyridine-4,6(5H,7H)-dione) |
| 52 | (3-amino-2-phenyl-7-(4-isopropylbenzylidene)-2H-pyrazolo[4,3-c]pyridine-4,6(5H,7H)-dione) |
| 53 | (3-amino-2-phenyl-7-(4-acetamidobenzylidene)-2H-pyrazolo[4,3-c]pyridine-4,6(5H,7H)-dione) |

TABLE 4-continued

| Ex. | structural formula |
|---|---|
| 54 | (3-amino-2-phenyl-7-([1,1'-biphenyl]-4-ylmethylene)-2H-pyrazolo[4,3-c]pyridine-4,6(5H,7H)-dione) |

TABLE 5

| Ex. | structural formula |
|---|---|
| 55 | (3-amino-7-(4-aminobenzylidene)-2-phenyl-2H-pyrazolo[4,3-c]pyridine-4,6(5H,7H)-dione · HCl) |
| 56 | (3-amino-7-(3,4-dihydroxybenzylidene)-2-phenyl-2H-pyrazolo[4,3-c]pyridine-4,6(5H,7H)-dione) |
| 57 | (3-amino-7-(3-hydroxybenzylidene)-2-phenyl-2H-pyrazolo[4,3-c]pyridine-4,6(5H,7H)-dione) |

TABLE 5-continued

| Ex. | structural formula |
|---|---|
| 58 | (3-amino-7-(4-(methoxycarbonyl)benzylidene)-2-phenyl-2H-pyrazolo[4,3-c]pyridine-4,6(5H,7H)-dione) |
| 59 | (3-amino-7-(3,5-dihydroxybenzylidene)-2-phenyl-2H-pyrazolo[4,3-c]pyridine-4,6(5H,7H)-dione) |
| 60 | (3-amino-7-(4-carboxybenzylidene)-2-phenyl-2H-pyrazolo[4,3-c]pyridine-4,6(5H,7H)-dione) |
| 61 | (3-amino-5-methyl-2-phenyl-7-benzylidene-2H-pyrazolo[4,3-c]pyridine-4,6(5H,7H)-dione) |
| 62 | (3-amino-7-((1H-indol-3-yl)methylene)-2-phenyl-2H-pyrazolo[4,3-c]pyridine-4,6(5H,7H)-dione) |

TABLE 5-continued

| Ex. | structural formula |
|---|---|
| 63 | (3-amino-2-phenyl-2H-pyrazolo[4,3-c]pyridine-4,6-dione with benzofuran-5-ylmethylene at 7-position) |
| 64 | (3-amino-2-phenyl-2H-pyrazolo[4,3-c]pyridine-4,6-dione with (1-methyl-1H-imidazol-2-yl)methylene at 7-position) |

TABLE 6

| Ex. | structural formula |
|---|---|
| 65 | (3-amino-2-phenyl-2H-pyrazolo[4,3-c]pyridine-4,6-dione with (1H-imidazol-4-yl)methylene at 7-position) |
| 66 | (3-amino-2-phenyl-2H-pyrazolo[4,3-c]pyridine-4,6-dione with (6-hydroxy-2H-chromen-3-yl)methylene at 7-position) |
| 67 | (3-amino-2-phenyl-2H-pyrazolo[4,3-c]pyridine-4,6-dione with (4-bromophenyl)methylene at 7-position) |

TABLE 6-continued

| Ex. | structural formula |
|---|---|
| 68 | (3-amino-2-phenyl-2H-pyrazolo[4,3-c]pyridine-4,6-dione with (4-fluorophenyl)methylene at 7-position) |
| 69 | (3-amino-2-phenyl-2H-pyrazolo[4,3-c]pyridine-4,6-dione with (2-bromophenyl)methylene at 7-position) |
| 70 | (3-amino-2-phenyl-2H-pyrazolo[4,3-c]pyridine-4,6-dione with (3-bromophenyl)methylene at 7-position) |
| 71 | (3-amino-2-phenyl-2H-pyrazolo[4,3-c]pyridine-4,6-dione with (2-methoxyphenyl)methylene at 7-position) |
| 72 | (3-amino-2-phenyl-2H-pyrazolo[4,3-c]pyridine-4,6-dione with (3-methoxyphenyl)methylene at 7-position) |

TABLE 6-continued

| Ex. | structural formula |
|---|---|
| 73 | 3-amino-2-phenyl-7-(2,6-dimethoxybenzylidene)-2H-pyrazolo[4,3-c]pyridine-4,6(5H,7H)-dione |
| 74 | 3-amino-2-phenyl-7-(2,4,6-trimethoxybenzylidene)-2H-pyrazolo[4,3-c]pyridine-4,6(5H,7H)-dione |

TABLE 7

| Ex. | structural formula |
|---|---|
| 75 | 3-amino-2-phenyl-7-(cyclohexylmethylene)-2H-pyrazolo[4,3-c]pyridine-4,6(5H,7H)-dione |
| 76 | 3-amino-2-phenyl-7-(2-methylpropylidene)-2H-pyrazolo[4,3-c]pyridine-4,6(5H,7H)-dione |
| 77 | 3-amino-2-phenyl-7-butylidene-2H-pyrazolo[4,3-c]pyridine-4,6(5H,7H)-dione |

TABLE 7-continued

| Ex. | structural formula |
|---|---|
| 78 | 3-amino-2-phenyl-7-(3-(methylthio)propylidene)-2H-pyrazolo[4,3-c]pyridine-4,6(5H,7H)-dione |
| 79 | 3-amino-2-phenyl-7-(pyridin-4-ylmethylene)-2H-pyrazolo[4,3-c]pyridine-4,6(5H,7H)-dione |
| 80 | 3-amino-2-phenyl-7-(pyridin-3-ylmethylene)-2H-pyrazolo[4,3-c]pyridine-4,6(5H,7H)-dione |
| 81 | 3-amino-2-phenyl-7-(pyridin-2-ylmethylene)-2H-pyrazolo[4,3-c]pyridine-4,6(5H,7H)-dione |
| 82 | 3-amino-2-phenyl-7-(thiophen-2-ylmethylene)-2H-pyrazolo[4,3-c]pyridine-4,6(5H,7H)-dione |
| 83 | 3-amino-2-phenyl-7-(furan-2-ylmethylene)-2H-pyrazolo[4,3-c]pyridine-4,6(5H,7H)-dione |

TABLE 7-continued

| Ex. | structural formula |
|---|---|
| 84 | (structure) |

TABLE 8

| Ex. | structural formula |
|---|---|
| 85 | (structure) |
| 86 | (structure) |
| 87 | (structure) |
| 88 | (structure) |

TABLE 8-continued

| Ex. | structural formula |
|---|---|
| 89 | (structure) |
| 90 | (structure) |
| 91 | (structure) |
| 92 | (structure) |
| 93 | (structure) |
| 94 | (structure) |

TABLE 9

| Ex. | structural formula |
|---|---|
| 95 | (4-bromophenyl) pyrazolo-pyridinedione with 3-NH₂ |
| 96 | (2,4,6-trimethylphenyl) pyrazolo-pyridinedione with 3-NH₂ |
| 97 | (2,2,2-trifluoroethyl) pyrazolo-pyridinedione with 3-NH₂ |
| 98 | 2-phenyl pyrazolo-pyridinedione with 3-NH₂ and spiro-cyclopropane |
| 99 | 3-(benzylamino)-2-phenyl pyrazolo-pyridinedione |
| 100 | 3-((4-chlorobenzyl)amino)-2-phenyl pyrazolo-pyridinedione |
| 101 | 3-((2-chlorobenzyl)amino)-2-phenyl pyrazolo-pyridinedione |

TABLE 9-continued

| Ex. | structural formula |
|---|---|
| 102 | 3-((4-fluorobenzyl)amino)-2-phenyl pyrazolo-pyridinedione |
| 103 | 3-((3-cyanobenzyl)amino)-2-phenyl pyrazolo-pyridinedione |
| 104 | 3-((3-chlorobenzyl)amino)-2-phenyl pyrazolo-pyridinedione |

TABLE 10

| Ex. | structural formula |
|---|---|
| 105 | 3-((3-hydroxybenzyl)amino)-2-phenyl pyrazolo-pyridinedione |
| 106 | 3-(propylamino)-2-phenyl pyrazolo-pyridinedione |

TABLE 10-continued

| Ex. | structural formula |
|---|---|
| 107 | |
| 108 | |
| 109 | |
| 110 | |
| 111 | |

TABLE 10-continued

| Ex. | structural formula |
|---|---|
| 112 | |
| 113 | |
| 114 | |

TABLE 11

| Ex. | structural formula |
|---|---|
| 115 | |
| 116 | |

TABLE 11-continued
| Ex. | structural formula |
|---|---|
| 117 |  |
| 118 | 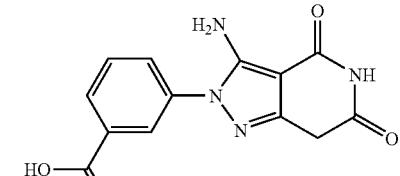 |
| 119 | 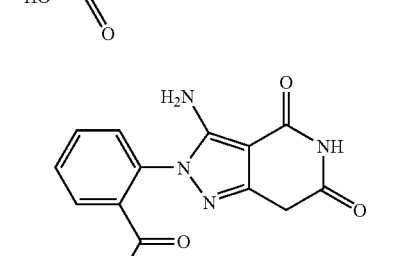 |
| 120 | 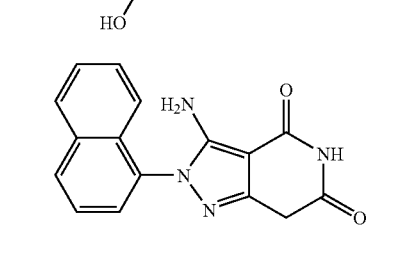 |
| 121 | 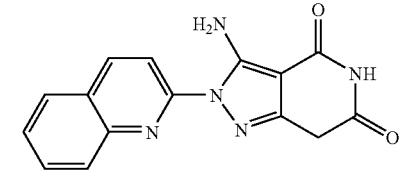 |
| 122 | 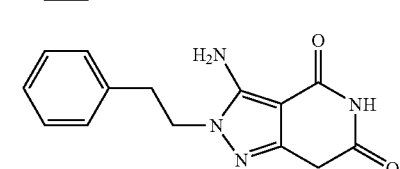 |
| 123 | 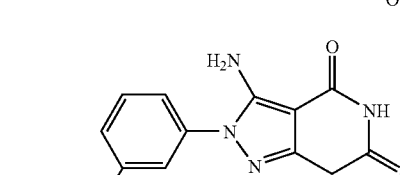 |
| 124 | 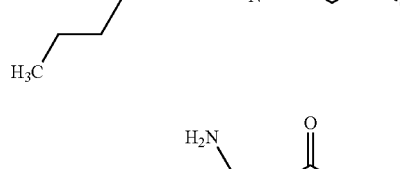 |
TABLE 11-continued
| Ex. | structural formula |
|---|---|
| 125 |  |
| 126 | 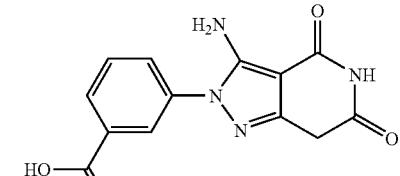 |
TABLE 12
| Ex. | structural formula |
|---|---|
| 127 | 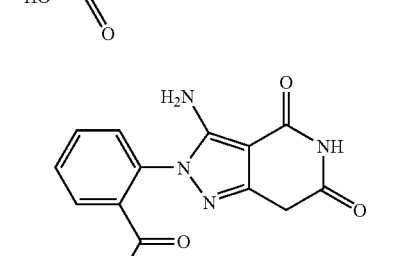 |
| 128 | 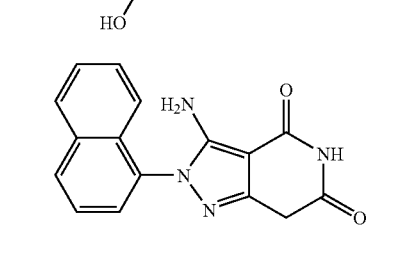 |
| 129 | 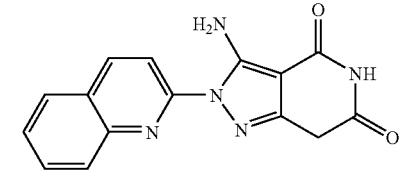 |
| 130 | 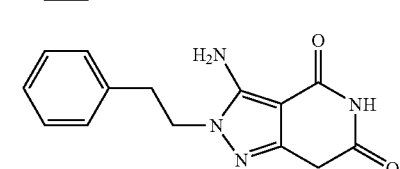 |

TABLE 12-continued
| Ex. | structural formula |
|---|---|
| 131 | |
| 132 | |
| 133 | |
| 134 | |
| 135 | |
TABLE 12-continued
| Ex. | structural formula |
|---|---|
| 136 | |
TABLE 13
| Ex. | structural formula |
|---|---|
| 137 | 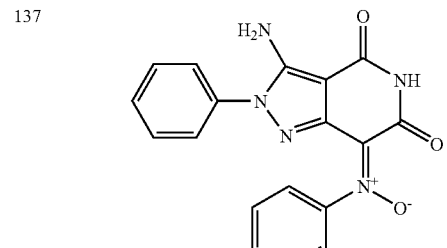 |
| 138 | 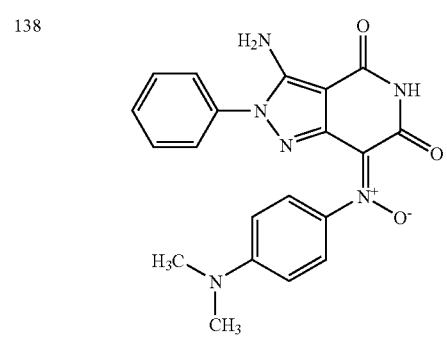 |
| 139 | 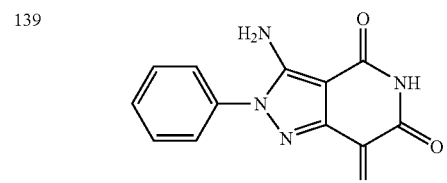 |
| 140 | 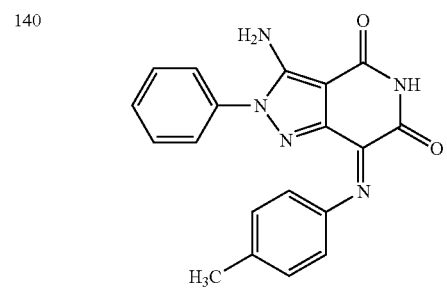 |

TABLE 13-continued

| Ex. | structural formula |
|---|---|
| 141 | (3-amino-2-phenyl-7-(2-phenylhydrazinylidene)-2H-pyrazolo[3,4-c]pyridine-4,6(5H,7H)-dione) |
| 142 | (3-amino-7-(hydroxyimino)-2-phenyl-2H-pyrazolo[3,4-c]pyridine-4,6(5H,7H)-dione) |
| 143 | (3-amino-7-(methoxyimino)-2-phenyl-2H-pyrazolo[3,4-c]pyridine-4,6(5H,7H)-dione) |
| 144 | (3-amino-7-(2-carbamoylhydrazinylidene)-2-phenyl-2H-pyrazolo[3,4-c]pyridine-4,6(5H,7H)-dione) |
| 145 | (3-amino-7-(2-acetylhydrazinylidene)-2-phenyl-2H-pyrazolo[3,4-c]pyridine-4,6(5H,7H)-dione) |

TABLE 13-continued

| Ex. | structural formula |
|---|---|
| 146 | (3-acetamido-2-phenyl-2H-pyrazolo[3,4-c]pyridine-4,6(5H,7H)-dione) |

TABLE 14

| Ex. | structural formula |
|---|---|
| 147 | (3-(methoxymethyleneamino)-2-phenyl-2H-pyrazolo[3,4-c]pyridine-4,6(5H,7H)-dione) |
| 148 | (3-amino-2-phenyl-7-(phenyl(sulfo)methyl)-2H-pyrazolo[3,4-c]pyridine-4,6(5H,7H)-dione sulfonic acid derivative) |
| 149 | (3-amino-7-(1-ethoxy-1-oxopropan-2-yl)-2-phenyl-2H-pyrazolo[3,4-c]pyridine-4,6(5H,7H)-dione) |
| 150 | (3-amino-7-hydroxy-2-phenyl-2H-pyrazolo[3,4-c]pyridine-4,6(5H,7H)-dione) |
| 151 | (3-amino-2-(4-hydroxyphenyl)-2H-pyrazolo[3,4-c]pyridine-4,6(5H,7H)-dione) |

TABLE 14-continued
| Ex. | structural formula |
|---|---|
| 152 | 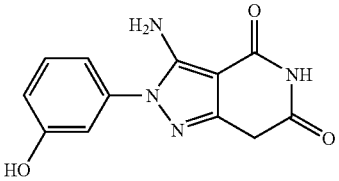 |
| 153 | 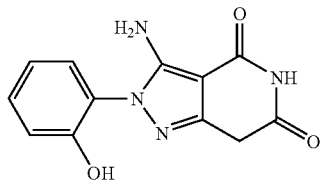 |
| 154 | 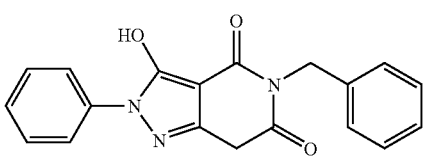 |
| 155 | 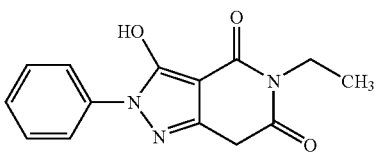 |
| 156 | 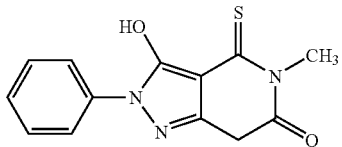 |
TABLE 15
| Ex. | structural formula |
|---|---|
| 157 | 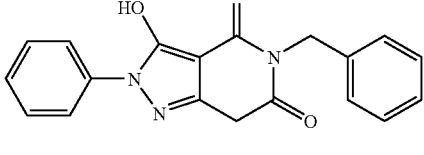 |
| 158 | 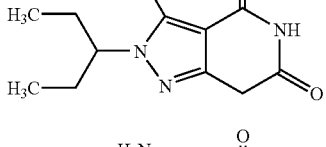 |
| 159 | 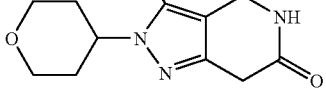 |
TABLE 15-continued
| Ex. | structural formula |
|---|---|
| 160 | 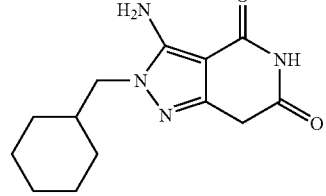 |
| 161 | 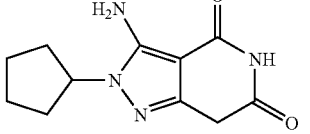 |
| 162 | 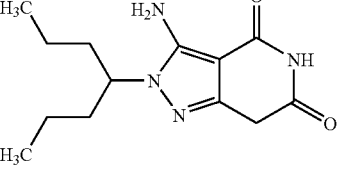 |
| 163 | 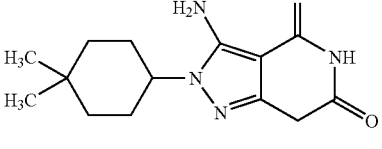 |
| 164 | 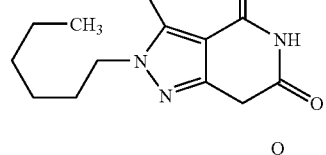 |
| 165 | 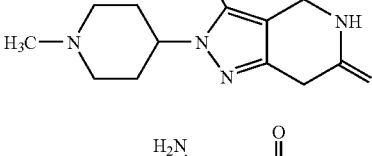 |
| 166 | 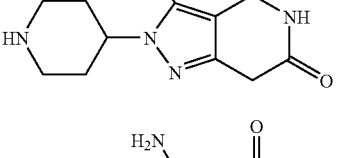 |
| 167 | 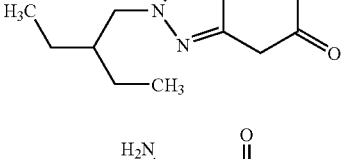 |
| 168 | 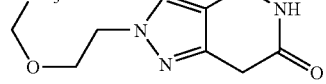 |

TABLE 15-continued
| Ex. | structural formula |
|---|---|
| 169 | 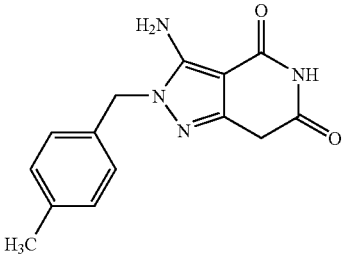 |
| 170 | 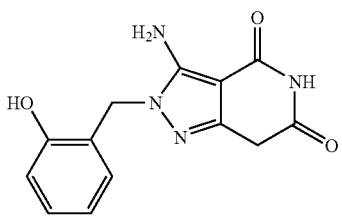 |
TABLE 16
| Ex. | structural formula |
|---|---|
| 171 | 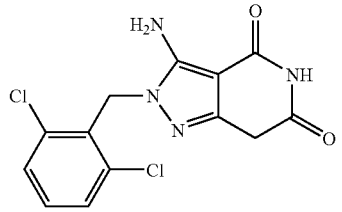 |
| 172 | 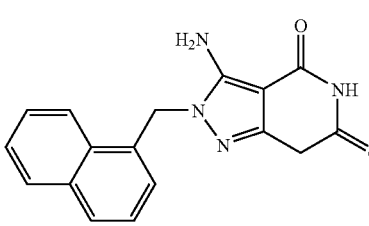 |
| 173 | 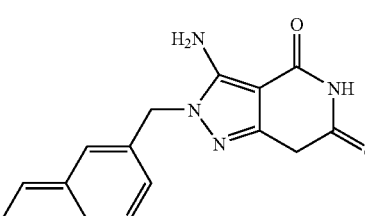 |
| 174 | 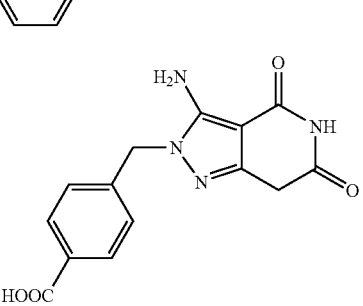 |
TABLE 16-continued
| Ex. | structural formula |
|---|---|
| 175 | 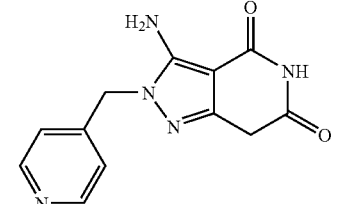 |
| 176 | 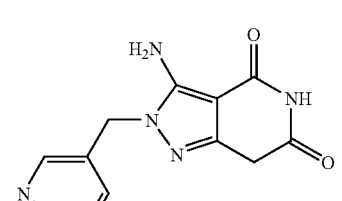 |
| 177 | 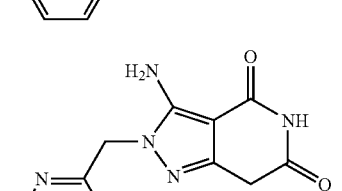 |
| 178 | 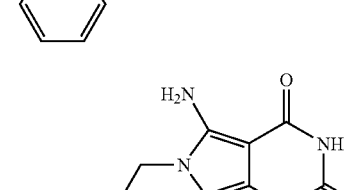 |
| 179 | 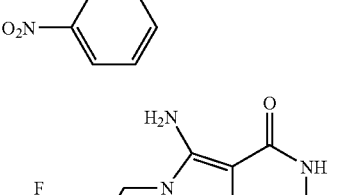 |
| 180 | 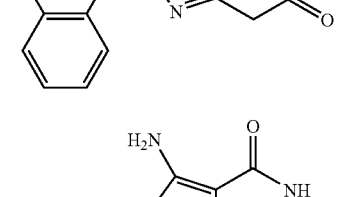 |
| 181 | 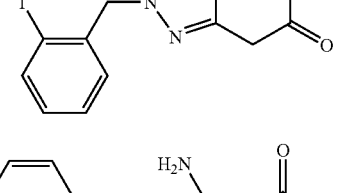 |

TABLE 16-continued

| Ex. | structural formula |
| --- | --- |
| 182 | (3-amino-2-(3-methoxybenzyl)-2,5,6,7-tetrahydro-4H-pyrazolo[4,3-c]pyridine-4,6-dione) |
| 183 | (3-((2-hydroxyethyl)amino)-2-phenyl-2,5,6,7-tetrahydro-4H-pyrazolo[4,3-c]pyridine-4,6-dione) |
| 184 | (3-(dimethylamino)-2-phenyl-2,5,6,7-tetrahydro-4H-pyrazolo[4,3-c]pyridine-4,6-dione) |

TABLE 17

| Ex. | structural formula |
| --- | --- |
| 185 | (3-morpholino-2-phenyl-2,5,6,7-tetrahydro-4H-pyrazolo[4,3-c]pyridine-4,6-dione) |
| 186 | (2-phenyl-3-(pyrrolidin-1-yl)-2,5,6,7-tetrahydro-4H-pyrazolo[4,3-c]pyridine-4,6-dione) |
| 187 | (3-(cyclohexylamino)-2-phenyl-2,5,6,7-tetrahydro-4H-pyrazolo[4,3-c]pyridine-4,6-dione) |

TABLE 17-continued

| Ex. | structural formula |
| --- | --- |
| 188 | (3-(4-hydroxypiperidin-1-yl)-2-phenyl-2,5,6,7-tetrahydro-4H-pyrazolo[4,3-c]pyridine-4,6-dione) |
| 189 | (2,3-diphenyl-2,5,6,7-tetrahydro-4H-pyrazolo[4,3-c]pyridine-4,6-dione) |
| 190 | (2-phenyl-3-(pyridin-4-yl)-2,5,6,7-tetrahydro-4H-pyrazolo[4,3-c]pyridine-4,6-dione) |
| 191 | (2-phenyl-3-(thiophen-2-yl)-2,5,6,7-tetrahydro-4H-pyrazolo[4,3-c]pyridine-4,6-dione) |
| 192 | (2-phenyl-3-(thiophen-3-yl)-2,5,6,7-tetrahydro-4H-pyrazolo[4,3-c]pyridine-4,6-dione) |
| 193 | (3-(3-methoxyphenyl)-2-phenyl-2,5,6,7-tetrahydro-4H-pyrazolo[4,3-c]pyridine-4,6-dione) |
| 194 | (3-amino-2-(5-chloro-2-hydroxyphenyl)-2,5,6,7-tetrahydro-4H-pyrazolo[4,3-c]pyridine-4,6-dione) |

TABLE 17-continued

| Ex. | structural formula |
|---|---|
| 195 | (structure: pyrazolo-pyridinone with 2,3-dihydroxyphenyl, H₂N) |
| 196 | (structure: pyrazolo-pyridinone with 3-fluoro-2-hydroxyphenyl, H₂N) |

TABLE 18

| Ex. | structural formula |
|---|---|
| 197 | (structure: pyrazolo-pyridinone with 5-carboxy-2-hydroxyphenyl, H₂N) |
| 198 | (structure: pyrazolo-pyridinone with 4-carboxy-2-hydroxyphenyl, H₂N) |

EXPERIMENTAL EXAMPLES

Experimental Example 1

Test for TNF-α Production or Inhibition of TNF-α Production from Mouse Peritoneal Macrophage Peritoneal cells were recovered from the peritoneal cavity of ICR mice (male, 5-7 weeks of age, Charles River) and sown in a 96-well half plate (Costar 3696) at a density of $1 \times 10^5$ cells per well. As the medium, RPMI-1640 containing 10% fetal calf serum was used and, using this medium, each reagent was prepared. Mouse GM-CSF (Peprotech) and mouse IFN-γ (Peprotech) were respectively added at a final concentration of 10 ng/ml, lipopolysaccharide (*E. coli* 0111: B4 LPS, DIFCO, lot 99078) was added at a final concentration of 5 ng/ml, and the compound of the present invention was added at 8 steps of dilution series by 3-fold dilution from the final concentration (300 μM), and cultured for 16 hrs. The concentration of TNF-α secreted into the culture supernatant was determined using a mouse TNF-α ELISA quantitative determination kit (Pharmingen, #2673KI) and the absorbance at 450 nm was measured using a V-max kinetic microplate reader (Molecular Devices). The concentration of the compound necessary for 50% suppression of TNF-α amount produced by lipopolysaccharide stimulation was taken as $IC_{50}$ (μM).

The results are shown in Table 19.

TABLE 19

| Example | $IC_{50}$ (μM) Mo-TNF |
|---|---|
| 5 | 23.9 |
| 9 | 18.0 |
| 10 | 22.9 |
| 11 | 15.2 |
| 12 | 11.8 |
| 13 | 5.0 |
| 14 | 27.3 |
| 16 | 20.1 |
| 19 | 32.8 |
| 21 | 3.5 |
| 25 | 28.0 |
| 26 | 15.1 |
| 27 | 28.3 |
| 33 | 79.1 |
| 36 | 80.5 |
| 46 | 23.7 |
| 49 | 32.7 |
| 52 | 8.6 |
| 53 | 7.9 |
| 55 | 6.1 |
| 56 | 3.3 |
| 57 | 7.8 |
| 60 | 3.7 |
| 64 | 3.5 |
| 66 | 3.5 |
| 71 | 4.5 |
| 72 | 80.5 |
| 73 | 5.6 |
| 74 | 4.4 |
| 77 | 14.7 |
| 78 | 10.6 |
| 82 | 78.5 |
| 83 | 93.2 |
| 86 | 9.7 |
| 88 | 9.9 |
| 92 | 31.9 |
| 98 | 18.4 |
| 112 | 82.2 |
| 124 | 9.4 |
| 125 | 10.8 |
| 129 | 8.4 |
| 133 | 0.3 |
| 135 | 8.3 |
| 136 | 4.3 |
| 143 | 26.2 |
| 149 | 99.7 |
| 153 | 9.0 |
| 158 | 5.8 |
| 159 | 26.9 |
| 160 | 60.3 |
| 161 | 10.9 |
| 162 | 13.0 |
| 163 | 2.6 |
| 164 | 2.1 |
| 167 | 26.8 |
| 170 | 13.2 |
| 172 | 83.1 |
| 176 | 3.5 |
| 180 | 8.7 |
| 186 | 14.7 |
| 187 | 16.6 |
| 190 | 77.3 |

Experimental Example 2

Suppressive Test of Lipopolysaccharide Induced TNF-α Production in Blood (In Vivo, Mouse)

Figure 1:
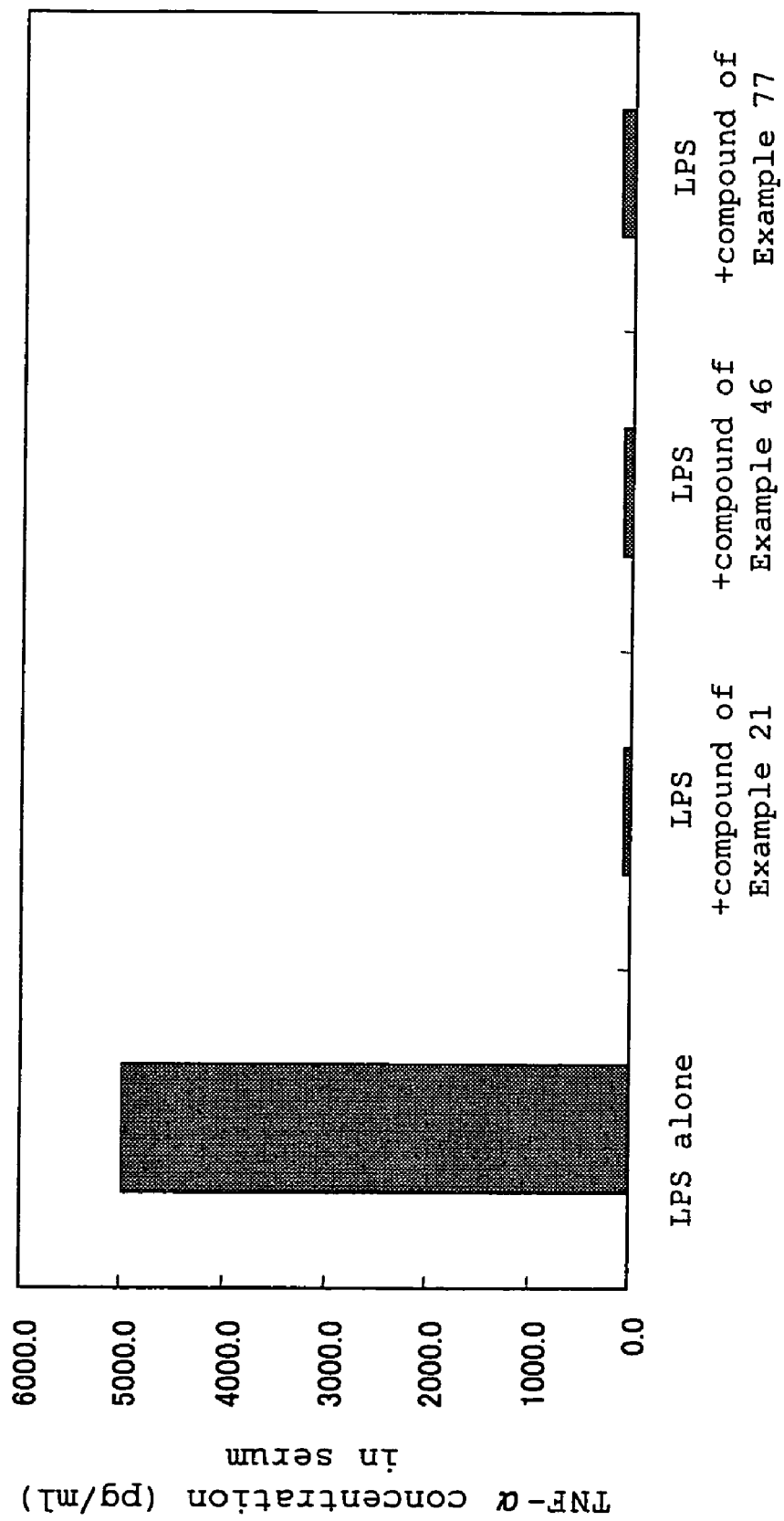
FIG. 1 is a graph showing the results of an inhibition test of lipopolysaccharide-induced TNF-α production in blood in mouse.

Each of the test compounds (Example compounds 21, 46 and 77) was suspended in PBS(−) containing 10% DMSO and 5% Tween 80, and intraperitoneally administered (30 mg/kg) to C57BL/6 mice (female, 8-12 weeks of age, Charles River, 3 mice per test compound). After 15 min, lipopolysaccharide (E. coli 0111: B4 LPS, DIFCO, lot 99078) dissolved in physiological saline was intravenously administered at a dose of 50 μg per mouse. Blood was taken from the heart under diethyl ether anesthesia, and the serum was separated by centrifugation. The TNF-α amount in serum was determined using a mouse TNF-α ELISA quantitative determination kit (Pharmingen, #2673KI) and the absorbance at 450 nm was measured using a V-mak kinetic microplate reader (Molecular Devices). The cytokine concentration was determined using a quantitative determination software SoftmaxPRO (Molecular Devices) by comparing with the calibration curve obtained using recombinant mouse TNF-α contained in the kit as a standard product. Furthermore, an average value of TNF-α in blood of 3 mice per each test compound was determined. The results are shown in FIG. 1.

Experimental Example 3

Efficacy Test Using Rat Adjuvant Arthritis

According to a conventional method, 50 μl of a light mineral oil (SIGMA) containing 3 mg/ml of killed *M. tuberculosis* (DIFCO, lot 165308) was subcutaneously injected into the sole of left hind limb of LEWIS rat (female, 7-week-old, Charles River Japan) to induce the onset of arthritis. The test compound was suspended in 0.5% aqueous carboxymethyl cellulose (CMC) solution and forcibly administered orally to the rats (4 per group). Each of the test compounds (Example compounds 3 and 153) was administered twice a day at a drug dose of 120 mg/kg body weight for 3 days from 24 hrs after the onset induction (acute inflammation stage evaluation), and 3 days from 13 days later (secondary inflammation stage evaluation). The volume of the hind limb was measured with time for changes in swelling due to arthritis. The results are shown in FIG. 2.

INDUSTRIAL APPLICABILITY

The compound group represented by the formula (I) of the present invention has a superior TNF-α production suppressing action, and further, a superior TNF-α production suppressing action in vivo, as well as superior efficacy against chronic inflammatory disease state. Accordingly, it is useful for the prophylaxis or treatment of various diseases caused by abnormal production of TNF-α.

This application is based on a patent application No. 130438/2001 filed in Japan, the contents of which are hereby incorporated by reference.

What is claimed is:
1. A heterocyclic compound represented by formula (I')

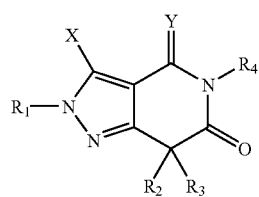

(I')

wherein $R_1$ is an alkyl group optionally having substituent(s), a cycloalkyl group optionally having substituent(s), a cycloalkylalkyl group optionally having substituent(s), an aralkyl group optionally having substituent(s), an aryl group optionally having substituent(s), a heteroaryl group optionally having substituent(s), a heteroarylalkyl group optionally having substituent(s), a cycloalkyl group containing hetero atom(s) in its ring optionally having substituent(s) or a cycloalkylalkyl group containing hetero atom(s) in its ring, $R_2$ and $R_3$ are the same or different and each is a hydrogen atom, a hydroxyl group, an alkyl group optionally having substituent(s) or an aralkyl group optionally having substituent(s), or may be linked to form a cycloalkyl group, a cycloalkyl group containing hetero atom(s) in its ring,

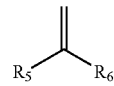

wherein $R_5$ and $R_6$ are the same or different and each is a hydrogen atom, an alkoxy group, an alkoxycarbonyl group, an alkyl group optionally having substituent(s), an aralkyl group optionally having substituent(s), an aryl group optionally having substituent(s) or a heteroaryl group optionally having substituent(s), or may be linked to form a cycloalkyl group or a cycloalkyl group containing hetero atom(s) in its ring,

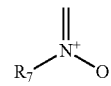

wherein $R_7$ is an aryl group optionally having substituent(s), =N—$R_8$ wherein $R_8$ is a hydroxyl group, an alkoxy group, an aryl group optionally having substituent(s) or a heteroaryl group optionally having substituent(s), =N—NH—$R_9$ wherein $R_9$ is an aryl group optionally having substituent(s), a heteroaryl group optionally having substituent(s), an acyl group or a carbamoyl group, or =O, $R_4$ is a hydrogen atom, an alkyl group optionally having substituent(s) or an aralkyl group optionally having substituent(s), X is a hydrogen atom, a halogen atom, a hydroxyl group, an alkyl group optionally having substituent(s), an aralkyl group optionally having substituent(s), an alkoxy group optionally having substituent(s), an aryl group optionally having substituent(s), a heteroaryl group optionally having substituent(s), an amino group optionally having substituent(s) selected from the group consisting of alkyl group, aralkyl group optionally having substituent(s), acyl group, cycloalkyl group, cycloalkylalkyl group, alkoxycarbonyl group, and aralkyloxycarbonyl group, 1-piperidyl group, 1-piperazyl group, morpholin-4-yl group, an alkylthio group optionally having substituent(s), an aralkylthio group optionally having substituent(s), an arylthio group optionally having substituent(s), a heteroarylthio group optionally having substituent(s), an alkylsulfonyl group optionally having substituent(s), an aralkylsulfonyl group optionally having substituent(s), an arylsulfonyl group optionally having substituent(s), a heteroarylsulfonyl group optionally having substituent(s), or an alkoxycarbonylthio group, and Y is an oxygen atom or a sulfur atom, provided that, when Y is an oxygen atom, $R_1$ is a phenyl group or a 2-carboxyethyl group or a methyl group, and X is an amino group, then all of $R_2$, $R_3$ and $R_4$ are not hydrogen atoms at the same time;

when Y is an oxygen atom, $R_1$ is a phenyl group, X is an amino group and $R_4$ is a hydrogen atom, then both $R_2$ and $R_3$ are not methyl groups at the same time;

when Y is an oxygen atom, $R_1$ is a phenyl group, X is an amino group, $R_4$ is a hydrogen atom and one of $R_5$ and $R_6$ is a hydrogen atom, then the other of $R_5$ and $R_6$ is not a phenyl group or a 3-pyridyl group;

when Y is an oxygen atom, $R_1$ is a phenyl group, X is a phenyl group and $R_4$ is a hydrogen atom, then both $R_2$ and $R_3$ are not hydrogen atoms at the same time or are not linked to form =N—NH—$R_9$' (wherein $R_9$' is a phenyl group);

when Y is an oxygen atom, $R_1$ is a phenyl group, X is a phenyl group, $R_4$ is a hydrogen atom and one of $R_5$ and $R_6$ is a hydrogen atom, then the other of $R_5$ and $R_6$ is not a phenyl group or a 4-chlorophenyl group; and when Y is an oxygen atom, $R_1$ is a 2-carboxyethyl group, X is an amino group, $R_4$ is a hydrogen atom and one of $R_5$ and $R_6$ is a hydrogen atom, then the other of $R_5$ and $R_6$ is not a phenyl group, or a pharmaceutically acceptable salt thereof.

2. The heterocyclic compound of claim 1, wherein $R_1$ is an alkyl group optionally having substituent(s), a cycloalkyl group optionally having substituent(s), a cycloalkylalkyl group optionally having substituent(s), an aralkyl group optionally having substituent(s), an aryl group optionally having substituent(s) or a heteroaryl group optionally having substituent(s)

or a pharmaceutically acceptable salt thereof.

3. The heterocyclic compound of claim 1, wherein $R_4$ is a hydrogen atom,

X is a halogen atom, an amino group optionally having substituent(s) selected from the group consisting of alkyl group, aralkyl group optionally having substituent(s), acyl group, cycloalkyl group, cycloalkylalkyl group, alkoxycarbonyl group, and aralkyloxycarbonyl group, 1-piperidyl group, 1-piperazyl group, morpholin-4-yl group, an alkylthio group optionally having substituent(s), an aralkylthio group optionally having substituent(s), an arylthio group optionally having substituent(s) or a heteroarylthio group optionally having substituent(s), and Y is an oxygen atom, or a pharmaceutically acceptable salt thereof.

4. The heterocyclic compound of claim 3, wherein $R_1$ is an aryl group optionally having substituent(s) or a heteroaryl group optionally having substituent(s), $R_2$ and $R_3$ may, in combination, form

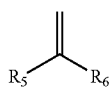

wherein $R_5$ and $R_6$ are the same or different and each is a hydrogen atom, an alkoxy group, an alkoxycarbonyl group, an alkyl group optionally having substituent(s), a cycloalkyl group optionally having substituent(s), an aralkyl group optionally having substituent(s), an aryl group optionally having substituent(s) or a heteroaryl group optionally having substituent(s), or may be linked to form a cycloalkyl group or a cycloalkyl group containing hetero atom(s) in its ring, and X is a halogen atom or an amino group optionally having substituent(s) selected from the group consisting of alkyl group, aralkyl group optionally having substituent(s), acyl group, cycloalkyl group, cycloalkylalkyl group, alkoxycarbonyl group, and aralkyloxycarbonyl group, 1-piperidyl group, 1-piperazyl group, morpholin-4-yl group, or a pharmaceutically acceptable salt thereof.

5. The heterocyclic compound of claim 4, wherein $R_1$ is a phenyl group optionally having substituent(s), and X is an amino group, or a pharmaceutically acceptable salt thereof.

6. The heterocyclic compound of claim 1, wherein $R_2$ and $R_3$ are hydrogen atoms, $R_4$ is a hydrogen atom, X is a halogen atom or an amino group optionally having substituent(s) selected from the group consisting of alkyl group, aralkyl group optionally having substituent(s), acyl group, cycloalkyl group, cycloalkylalkyl group, alkoxycarbonyl group, and aralkyloxycarbonyl group, 1-piperidyl group, 1-piperazyl group, morpholin-4-yl group, and Y is an oxygen atom, or a pharmaceutically acceptable salt thereof.

7. The heterocyclic compound of claim 6, wherein X is an amino group, or a pharmaceutically acceptable salt thereof.

8. The heterocyclic compound of claim 1, wherein $R_1$ is an alkyl group optionally having substituent(s), a cycloalkyl group optionally having substituent(s), a cycloalkylalkyl group, an aralkyl group optionally having substituent(s), an aryl group optionally having substituent(s), a heteroaryl group, a heteroarylalkyl group or a cycloalkyl group containing hetero atom(s) in its ring optionally having substituent(s), $R_2$ and $R_3$ are the same or different and each is a hydrogen atom, a hydroxyl group, an alkyl group optionally having substituent(s) or an aralkyl group optionally having substituent(s), or may, in combination, form a cycloalkyl group,

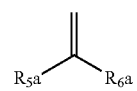

wherein $R_5a$ and $R_6a$ are the same or different and each is a hydrogen atom, an alkoxycarbonyl group, an alkyl group optionally having substituent(s), a cycloalkyl group, an aryl group optionally having substituent(s) or a heteroaryl group optionally having substituent(s), or may be linked to form a cycloalkyl group or a cycloalkyl group containing hetero atom(s) in its ring,

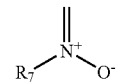

wherein $R_7$ is an aryl group optionally having substituent(s), =N—$R_8a$ wherein $R_8a$ is a hydroxyl group, an alkoxy group or an aryl group optionally having substituent(s)), =N—NH—$R_9a$ wherein $R_9a$ is an aryl group optionally having substituent(s), an acyl group or a carbamoyl group, or =O, R$_4$ is a hydrogen atom, an alkyl group or an aralkyl group, and X is a hydrogen atom, a halogen atom, a hydroxyl group, an aryl group optionally having substituent(s), a heteroaryl group optionally having substituent(s), an amino group optionally having substituent(s) selected from the group consisting of alkyl group, aralkyl group optionally having substituent(s), acyl group, cycloalkyl group, cycloalkylalkyl group, alkoxycarbonyl group, and aralkyloxycarbonyl group, 1-piperidyl group, 1-piperazyl group, morpholin-4-yl group, an alkylthio group optionally having substituent(s), aralkylthio group, an arylthio group optionally having substituent(s), an alkylsulfonyl group, an arylsulfonyl group optionally having substituent(s), or an alkoxycarbonylthio group, or a pharmaceutically acceptable salt thereof.

9. A heterocyclic compound selected from the group consisting of

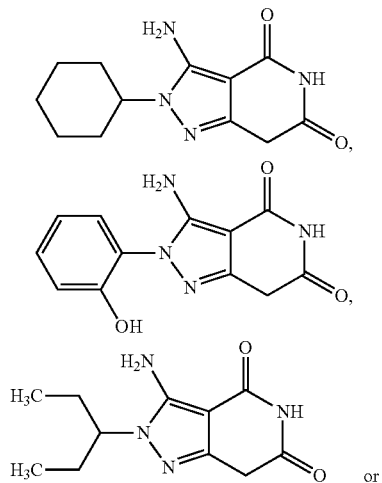

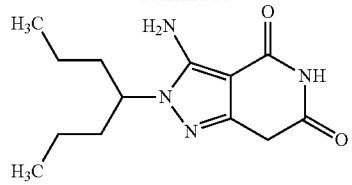

and pharmaceutically acceptable salts thereof.

10. A pharmaceutical composition, which comprises a heterocyclic compound according to claim 1 or a pharmaceutically acceptable salt thereof, and
a pharmaceutically acceptable carrier.

11. The pharmaceutical composition of claim 10, wherein said pharmaceutically acceptable carrier is at least one member selected from the group consisting of an excipient, a diluent, an extender, a disintegrant, a stabilizer, a preservative, a buffer, an emulsifier, a flavoring agent, a coloring agent, a sweetening agent, a thickener, a corrigent, a solubilizer, and mixtures thereof.

12. The pharmaceutical composition of claim 10, which is in a form selected from the group consisting of a tablet, a pill, a powder, a granule, a suppository, a liquid, a capsule, a troche, and an aerosol.

13. A pharmaceutical composition, which comprises a heterocyclic compound according to claim 9 or a pharmaceutically acceptable salt thereof, and
a pharmaceutically acceptable carrier.

14. The pharmaceutical composition of claim 13, wherein said pharmaceutically acceptable carrier is at least one member selected from the group consisting of an excipient, a diluent, an extender, a disintegrant, a stabilizer, a preservative, a buffer, an emulsifier, a flavoring agent, a coloring agent, a sweetening agent, a thickener, a corrigent, a solubilizer, and mixtures thereof.

15. The pharmaceutical composition of claim 13, which is in a form selected from the group consisting of a tablet, a pill, a powder, a granule, a suppository, a liquid, a capsule, a troche, and an aerosol.

* * * * *

UNITED STATES PATENT AND TRADEMARK OFFICE
CERTIFICATE OF CORRECTION

PATENT NO. : 7,902,179 B2
APPLICATION NO. : 10/475097
DATED : March 8, 2011
INVENTOR(S) : Yasuhiro Tanaka et al.

It is certified that error appears in the above-identified patent and that said Letters Patent is hereby corrected as shown below:

Column 92, claim 1, line 23 after the "," insert

--a cycloalkyl group optionally having substituent(s),--

Signed and Sealed this
Second Day of August, 2011

David J. Kappos
*Director of the United States Patent and Trademark Office*